United States Patent [19]

Klaveness et al.

[11] Patent Number: 5,676,925
[45] Date of Patent: *Oct. 14, 1997

[54] CONTRAST AGENTS COMPRISING GAS-CONTAINING OR GAS-GENERATING POLYMER MICROPARTICLES OR MICROBALLOONS

[75] Inventors: Jo Klaveness, Oslo; Pål Rongved, Hellvik; Jan Solberg, Eiksmarka; Per Strande, Oslo; Unni Nordby Wiggen, Rasta; Keith Redford, Hagan, all of Norway

[73] Assignee: Nycomed Imaging AS, Oslo, Norway

[*] Notice: The term of this patent shall not extend beyond the expiration date of Pat. No. 5,529,766.

[21] Appl. No.: 478,034

[22] Filed: Jun. 7, 1995

Related U.S. Application Data

[60] Division of Ser. No. 301,002, Sep. 6, 1994, which is a continuation-in-part of Ser. No. 284,464, filed as PCT/GB93/00470, Mar. 5, 1993.

[30] Foreign Application Priority Data

Mar. 6, 1992 [GB] United Kingdom ............ 9204918
Mar. 6, 1992 [GB] United Kingdom ............ 9204920

[51] Int. Cl.[6] .................. C08G 63/00; A61K 9/14
[52] U.S. Cl. .................. 424/9.3; 424/9.5; 424/9.51; 424/9.52; 528/271; 528/370; 436/173
[58] Field of Search ............ 424/9.3, 9.5, 9.51, 424/9.52; 528/271, 370; 436/173

[56] References Cited

U.S. PATENT DOCUMENTS

| | | | |
|---|---|---|---|
| 5,198,208 | 3/1993 | Berg et al. | 424/1.1 |
| 5,322,681 | 6/1994 | Klaveness | 424/9 |
| 5,354,549 | 10/1994 | Klaveness et al. | 424/5 |
| 5,370,861 | 12/1994 | Klaveness et al. | 424/5 |
| 5,416,223 | 5/1995 | Klaveness et al. | 549/65 |
| 5,496,534 | 3/1996 | Klaveness et al. | 424/9.32 |
| 5,529,766 | 6/1996 | Klaveness et al. | 424/9.52 |
| 5,531,978 | 7/1996 | Berg et al. | 424/1.11 |
| 5,534,250 | 7/1996 | Klaveness et al. | 424/8.37 |
| 5,536,490 | 7/1996 | Klaveness et al. | 424/9.52 |

FOREIGN PATENT DOCUMENTS

| | | |
|---|---|---|
| 0 458 745 | 11/1991 | European Pat. Off. |
| WO-A-92 04392 | 3/1992 | WIPO |
| WO-A-92 17212 | 10/1992 | WIPO |
| WO-A-92 17213 | 10/1992 | WIPO |
| WO-A-92 21382 | 12/1992 | WIPO |

*Primary Examiner*—Jeffrey C. Mullis
*Attorney, Agent, or Firm*—Bacon & Thomas

[57] ABSTRACT

Contrast agents comprising gas-containing or gas-generating polymer microparticles and/or microballoons, in which the polymer is a biodegradable polymer containing units of formula

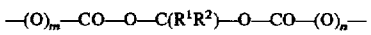

$$-(O)_m-CO-O-C(R^1R^2)-O-CO-(O)_n-$$

(wherein $R^1$ and $R^2$ each represent hydrogen or a carbon-attached monovalent organic group or together form a carbon-attached divalent organic group, and m and n are each independently zero or one) may be used in diagnostic applications such as ultrasound and MR imaging.

50 Claims, 6 Drawing Sheets

CONTRAST AGENTS COMPRISING GAS-CONTAINING OR GAS-GENERATING POLYMER MICROPARTICLES OR MICROBALLOONS

This application is a divisional of application Ser. No. 08/301,002, filed Sep. 6, 1994; which is a continuation-in-part of application Ser. No. 08/284,464, filed on Aug. 15, 1994 as the national phase of International Application No. PCT/GB93/00470, dated Mar. 5, 1993.

This invention relates to novel contrast agents, more particularly to new gas-containing or gas-generating contrast agents of use in diagnostic imaging.

It is well known that ultrasonic imaging comprises a potentially valuable diagnostic tool, for example in studies of the vascular system, particularly in cardiography, and of tissue microvasculature. A variety of contrast agents has been proposed to enhance the acoustic images so obtained, including suspensions of solid particles, emulsified liquid droplets, gas bubbles and encapsulated gases or liquids. It is generally accepted that low density contrast agents which are easily compressible are particularly efficient in terms of the acoustic backscatter they generate, and considerable interest has therefore been shown in the preparation of gas-containing and gas-generating systems.

Initial studies involving free gas bubbles generated in vivo by intracardiac injection of physiologically acceptable substances have demonstrated the potential efficiency of such bubbles as contrast agents in echocardiography; such techniques are severely limited in practice, however, by the short lifetime of the free bubbles. Interest has accordingly been shown in methods of stabilising gas bubbles for echocardiography and other ultrasonic studies, for example using emulsifiers, oils, thickeners or sugars, or by entraining or encapsulating the gas or a precursor therefor in a variety of polymer systems, e.g. as porous gas-containing polymer microparticles or as gas "microballoons" encapsulated by polymer coatings.

Thus, for example, WO 80/02365 discloses the use of gelatin encapsulated gas microbubbles for enhancing ultrasonic images. Such microbubbles do not, however, exhibit adequate stability at the dimensions preferred for use in echocardiography (1–10 μm) in view of the extreme thinness of the encapsulating coating.

U.S. Pat. No. 4,774,958 discloses the use of microbubble dispersions stabilised by encapsulation in denatured protein, e.g. human serum albumin. Such systems permit the production of microbubble systems having a size of e.g. 2–5 μm but still do not permit efficient visualisation of the left heart and myocardium. The use of such protein-derived agents may also create problems with regard to potential allergenic reactions.

EP-A-0327490 discloses, inter alia, ultrasonic contrast agents comprising a microparticulate synthetic biodegradable polymer containing a gas or volatile fluid (i.e. having a boiling point below 60° C.) in free or bonded form. Representative synthetic biodegradable polymers include polyesters of hydroxy carbonic acids, polyalkyl cyanoacrylates, polyamino acids, polyamides, polyacrylated saccharides and polyorthoesters.

Similar biodegradable microparticulate polymers, based on polymerised aldehydes, are described in EP-A-0441468, while systems based on microparticulate poly (amino acid)—poly (cyclic imide) derivatives are described in EP-A-0458079.

EP-A-0458745 discloses air or gas-filled microballoons in which the encapsulating material is a deformable and resilient interfacially deposited polymer which is preferably biodegradable, examples including polysaccharides, polyamino acids, polylactides, polyglycolides, lactide/lactone copolymers, polypeptides, proteins, polyorthoesters, polydioxanone, poly-β-aminoketones, polyphosphazenes, polyanhydrides and poly (alkyl cyanoacrylates). The microballoons are normally prepared by emulsion techniques leading to deposition of the polymer around droplets of a volatile liquid which is subsequently evaporated.

In WO 91/12823 there are described ultrasound contrast agents comprising gas- or vapour-filled polymer microcapsules; preferred polymers include insolubilised proteins such as denatured albumin. The microcapsules may be prepared by forming a protein shell around a solid or liquid core (e.g. by methods using simple or complex coacervation, double emulsion or minimisation of solubility at isoelectric point), hardening the shell (e.g. by chemical or heat treatment), and removing the core (e.g. by sublimation or evaporation). The use of double emulsion techniques will provide microcapsules having a honeycomb structure with multiple gas- or vapour-filled chambers.

Gas-containing contrast media are also known to be effective in magnetic resonance (MR) imaging, e.g. as susceptibility contrast agents which will act to reduce MR signal intensity. Oxygen-containing contrast media also represent potentially useful paramagnetic MR contrast agents.

Furthermore, in the field of X-ray imaging it has been observed that gases such as carbon dioxide may be used as negative oral contrast agents.

It is generally acknowledged that polymer-based contrast agents should desirably be biodegradable in order to facilitate their ultimate elimination from or absorption by the test subject. Little attention has been given, however, to the specific design of polymers to maximise this objective, reliance generally being made on the inherent, albeit slow, biodegradability of polymers such as polyesters, polyanhydrides, polycarbonates, polyamides and polyurethanes which principally results from the susceptibility of ester, amide or urethane groups therein to enzymic hydrolysis.

One exception occurs in EP-A-0458745, which suggests the use as ultrasound contrast agents of, inter alia, a specific category of esterified polypeptide derivatives reported to exhibit controlled biodegradability. These polymers, which are described in EP-A-0130935 as delayed release carriers for drugs, comprise compounds of formula

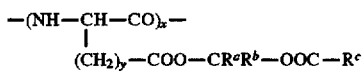

(in which $R^a$ and $R^b$ are alkyl groups or hydrogen atoms and $R^c$ is an optionally substituted aliphatic or aromatic group or $R^b$ is a hydrogen atom or an alkyl group and $R^a$ and $R^c$ together form a divalent group such as a dimethylene, vinylene or phenylene group, y is 1 or 2, and x is such that the molecular weight of the polymer is at least 5000) and copolymers thereof with other poly (amino acids). The first step in the biodegradation of such polymers is said to be cleavage of the side chain methylene diester groups to yield polymers containing units of formula

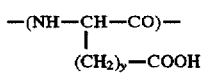

It is stated that such polymers will then be further degraded by peptidases to their component amino acid(s), which may be absorbed by the host to which the polymer/drug combination was administered, an inherently slow process. Furthermore, the peptide structures may be capable of causing allergenic reactions.

There is thus a continuing need for polymer-based contrast agents which combine the properties of good storage stability, stability in vivo upon administration, preferably for at least several passages of circulation in the case of intracardiac injections, and rapid biodegradation thereafter.

The present invention is based on our findings that these objectives may be fulfilled by contrast agents based on polymers containing methylene diester groups of the formula (I)

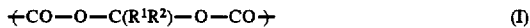  (I)

(where $R^1$ and $R^2$ each represent a hydrogen atom or a carbon-attached monovalent organic group or $R^1$ and $R^2$ together form a carbon-attached divalent organic group). Such units are particularly rapidly degraded by common esterase enzymes but are stable in the absence of enzymes. They may be attached not only to carbon-attached organic groups as in simple carboxylate esters but also to —O— atoms as in carbonate esters.

Polymers of this type and a variety of methods for their preparation are described and claimed in our copending International Patent Application No. WO 92/04392, the contents of which are incorporated herein by reference. The units of formula (I) in such polymers may, for example, be present in the polymer backbone, either as repeating units or as linking units between polymer sections, or may be present in crosslinking groups between polymer chains.

A further class of polymers of this type and methods for their preparation are described and claimed in a copending application of even date and comprise non-crosslinked polymers of low or zero water-solubility having a non-polypeptide polymer backbone carrying side chains, at least a proportion of the said side chains containing lipophilic moieties bonded to the polymer backbone by way of methylene diester units of formula (I), whereby the said lipophilic moieties are biodegradatively cleavable to yield a water-soluble polymer.

Thus according to one aspect of the present invention there are provided contrast agents comprising gas-containing or gas-generating polymer microparticles and/or microballoons, characterised in that the polymer is a biodegradable polymer containing units of formula (II)

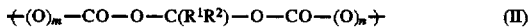  (II)

(wherein $R^1$ and $R^2$ are defined above and m and n, which may be the same or different, are each zero or 1).

Polymers having units of formula (II) in which one or both of n and m are 1, i.e. containing carbonate ester groups, have not previously been proposed other than in WO 92/04392 referred to above, and may be particularly readily biodegradable in some cases.

Polymers having a polypeptide backbone may give unwanted allergenic reactions and in general non-polypeptide polymers are preferred.

Polymers useful used in accordance with the invention may contain units of the formula (III)

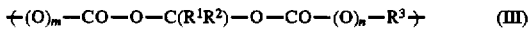  (III)

where $R^1$, $R^2$, m and n have the above meanings and $R^3$ is a divalent organic grouping, e.g. a carbon-attached divalent organic grouping.

Such polymers may comprise a plurality of units of formula (III) having different meanings for m, n, $R^1$, $R^2$ and $R^3$, for example as in block or graft copolymers. The diester linkages may occur at intervals throughout the polymer, e.g. as crosslinking groups or between copolymer sections, in which case $R^3$ will represent a polymeric grouping. Alternatively the linkages may be present throughout substantially the whole of the polymer, in which case $R^3$ will preferably be a low molecular weight grouping.

Particularly interesting units (III) are those in which m is 0 and n is 0 or 1, i.e. dicarboxylate units of the formula (IV)

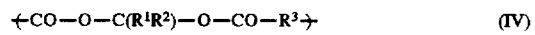  (IV)

or carboxylate-carbonate units of the formula (V)

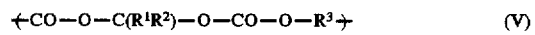  (V)

$R^1$ and $R^2$ may, for example, each by hydrogen or a carbon-attached hydrocarbyl or heterocyclic group, for example having 1–20 carbon atoms, e.g. an aliphatic group such as an alkyl or alkenyl group (preferably having up to 10 carbon atoms), a cycloalkyl group (preferably having up to 10 carbon atoms), an araliphatic group such as an aralkyl group (preferably having up to 20 carbon atoms), an aryl group (preferably having up to 20 carbon atoms) or a heterocyclic group having up to 20 carbon atoms and one or more heteroatoms selected from O, S and N. Such a hydrocarbyl or heterocyclic grouping may carry one or more functional groups such as halogen atoms or groups of the formulae —$NR^4R^5$, —$CONR^4R^5$, —$OR^6$, —$SR^6$ and —$COOR^7$, where $R^4$ and $R^5$, which may be the same or different, are hydrogen atoms, acyl groups, or hydrocarbyl groups as defined for $R^1$ and $R^2$; $R^6$ is a hydrogen atom or an acyl group or a group as defined for $R^1$ or $R^2$ and $R^7$ is a hydrogen atom or a group as defined for $R^1$ or $R^2$. Where $R^1$ and $R^2$ represent a divalent grouping this may, for example, be an alkylidene, alkenylidene, alkylene or alkenylene group (preferably having up to 10 carbon atoms), which may carry one or more functional groups as defined above.

As indicated above, the diester groupings of formula (I) may be separated by a wide range of groupings. Where it is desired that the polymer should break down into relatively short sections to aid biodegradation, the group $R^3$ which separates the diester units of formula (II) may, for example, be an alkylene or alkenylene group (e.g. containing up to 20, more preferably up to 10 carbon atoms), a cycloalkylene group (preferably having up to 10 carbon atoms), an aralkylene group (preferably having up to 20 carbon atoms and which may be bonded via the aryl and/or alkyl moieties—such aralkyl groups include, for example, two aryl groups joined by an alkylene chain) or a heterocyclic group having one or more hetero-atoms selected from O, S and N (preferably having up to 20 carbon atoms). The group $R^3$ may carry functional groups, e.g. as set out above for $R^1$ and $R^2$ and/or substituents such as oxo groups; the carbon chains of $R^3$ groups may be interrupted and/or terminated by heteroatoms such as O, N or S, e.g. in conjunction with oxo substituents to form linkages such as ester, thioester or amide groups. In order to enhance hydrophilicity of the polymers $R^3$ may for example comprise one or more sets of oxyethylene or polyoxyethylene units and/or hydroxyl-substituted carbon chains (e.g. as in hydroxyalkyl groups or sugar groups). Such sets of units may, for example, be linked through oxycarbonyl groups, e.g. by short chain diacid groups such as oxalyl, malonyl, succinyl, glutaryl or adipoyl.

One useful class of $R^3$ groups comprises two hydroxyalkyl groups, e.g. each containing up to 20 carbon atoms, linked by a short chain diacid group, for example derived from an aliphatic diacid containing up to 10 carbon atoms. Such groups may be represented by the formula

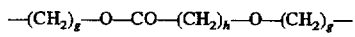

where g represents an integer of up to 20, e.g. in the range 9–19, and h represents an integer in the range 1–8. In polymers containing units of formula (III) where m and n are both zero, such groups will ultimately biodegrade to yield ω-hydroxyalkanoic acids such as 10-hydroxydecanoic, 12-hydroxydodecanoic and 16-hydroxyhexadecanoic acids which may be further metabolised in vivo through normal fatty acid metabolic pathways.

Where the group $R^3$ comprises a polymeric grouping, this may, for example, be a polyamide, poly(hydroxy acid), polyester, polycarbonate, polysaccharide, polyoxyethylene, polyoxyethylene-polyoxypropylene block copolymer, polyvinyl alcohol or polyvinyl ether/alcohol grouping.

The wide range of possible groups $R^1$, $R^2$ and $R^3$ enables the hydrophobicity or hydrophilicity of the polymer to be adjusted to any required use. Thus, the polymers may advantageously be designed to be water-insoluble but yield water-soluble degradation products upon enzymic hydrolysis.

Aliphatic groups present as, for example, $R^1$ and $R^2$ may be straight or branched, saturated or unsaturated and include, for example, alkyl and alkenyl groups, e.g. methyl, ethyl, propyl, isopropyl, butyl, decyl or allyl groups. Araliphatic groups include (monocarbocyclic aryl)-alkyl groups, for example benzyl groups. Aryl groups include mono- or bi-cyclic aryl groups, for example phenyl, tolyl or naphthyl groups. Heterocyclic groups include 5- or 6- membered heterocyclic groups preferably having one heteroatom, for example furyl, thienyl or pyridyl groups. Halogen atom substituents may, for example, be chlorine, bromine or iodine.

Biodegradation of polymers containing units of formula (III) will in general take place by enzymic hydrolytic cleavage of the bonds linking the group —O—C($R^1R^2$)—O— to the adjacent carbonyl groups, generally yielding an aldehyde or ketone of the formula $R^1$—CO—$R^2$. The intervening sections will form different products according to whether m or n is zero or 1. Where m or n is zero, hydrolyric cleavage will generally yield a carboxyl group; where m or n is 1, a hypothetical carbonic acid group —$R^3$—O—COOH is formed which generally eliminates carbon dioxide to form a grouping —$R^3$—OH. This can be of use where liberation of carbon dioxide is physiologically or functionally desirable. The use of polymers containing units of formula (III) wherein $R^1$ represent methyl and $R^2$ represents a hydrogen atom may be of advantage since the —O—C($R^1R^2$)—O— moiety of such polymers will biodegrade to yield acetaldehyde, an endogenous substance that will be oxidised in vivo to acetic acid, as in the metabolism of ethanol.

As indicated above, the units of formula (III) may be different within the same polymer, i.e. the polymers may be copolymers such as block or graft copolymers. The polymers may be copolymers formed with non-biodegradable monomers; the non-biodegradable sections remaining after enzymic or other cleavage are preferably of acceptable size to ensure their water-solubility or water-dispersibility and thus permit ready dispersal or removal; it is possible to consider such non-biodegradable sections as part of the groupings $R^3$ in formula (III) which, in effect, link together the biodegradable groupings of formula (II).

The polymers may be linear, branched or crosslinked. Branched and crosslinked polymers will in general make use of functional groups or double bonds in the corresponding $R^1$, $R^2$ or $R^3$ groups of their monomers. The resulting crosslinked or branched polymers will thus contain some units of formula (III) wherein $R^1$, $R^2$ and/or $R^3$ are substituted with the crosslinking or branched chains.

In general, where the carbon atoms linking the groups $R^3$ to the groupings of formula (II) are chiral, the chirality is preferably that found in natural products since the degrading enzymes will generally act more efficiently on such structures.

It has been generally observed that in crosslinked biodegradable polymers the crosslinking sections are often degraded first, thus exposing the rest of the network to enzymic hydrolysis. It is particularly useful, therefore, to have groups of formula (II) in the crosslinking chains of a polymer. One possibility is thus to convert a water-soluble long chain natural or synthetic non-biodegradable or slowly biodegradable substance, e.g. a polysaccharide or oligosaccharide, or a short chain polyacrylamide, into a water-insoluble form by crosslinking using crosslinking units containing groupings of formula (II). This may minimise the cost of the final product by reducing the amount of the relatively expensive biodegradable units of formula (II).

Block copolymers may, for example, have the structure

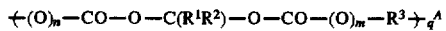

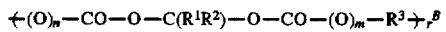

where the respective values of $R^1$, $R^2$, $R^3$, m and n are such that the repeating units in blocks A and B are different and q and r are integers, e.g. 10–20. One or more further blocks may be attached to those shown above.

Polymers containing units of formula (III) which are useful in accordance with the present invention may, for example, be prepared as described in the aforementioned Application No. WO 92/04392.

Another class of polymers useful in accordance with the invention contain units of formula (VI)

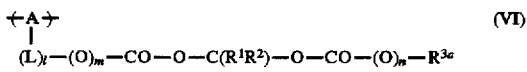
(VI)

where A represents a repeating unit of a non-polypeptide polymer backbone chain; L represents a linking group; l is zero or 1; m, n, $R^1$ and $R^2$ are as hereinbefore defined; and $R^{3a}$ represents a lipophilic organic group, e.g. an organic group as hereinbefore defined for $R^1$ and $R^2$. The group A and the group L (where present) should be such that the polymeric degradation products resulting from biodegradative cleavage of the methylene diester grouping, which typically contains units of formula (VII)

(VII)

(where A, L and l are as hereinbefore defined) when m in formula (VI) is zero and units of formula (VIII)

(VIII)

(where A, L and l are as hereinbefore defined) when m in formula (VI) is 1, are water-soluble.

Factors influencing the water solubility of these polymeric degradation products include the nature of the repeating units A and any comonomer units which may be present, the length of any linking group L, and the overall chain length of the polymer.

Repeating units A and any comonomer units are preferably comparatively short, for example containing up to 10, e.g. 1–6 carbon atoms and may optionally be interrupted by one or more heteroatoms selected from oxygen, nitrogen and sulphur and/or substituted by one or more substituents comprising such heteroatoms (e.g. as in oxo, hydroxy and amino groups). Where hydrophilic groups are included in the repeating units A and/or any comonomer units, the size of these units need not be limited and possible units thus include polyoxyethylene (e.g. as in polyoxyethylene esters of methacrylic acid).

Any linking groups L are preferably of short length and include, for example, $C_{1-3}$ alkylene groups such as methylene, ethylene or propylene optionally linked to the polymer backbone by and/or (where appropriate) interrupted by, for example, oxy, carbonyl, oxycarbonyl, imino or iminocarbonyl groups. Where polar groupings such as oxygen atoms or imino groups are present the linking groups may be longer without unduly inhibiting water solubility. Suitable polymeric degradation products thus include, for example, polyvinyl alcohol, polyacrylic acid, polymethacrylic acid, polyhydroxyalkyl acrylates and methacrylates such as poly(2-hydroxyethyl acrylate), polysaccharides such as starch and dextran, polyesters, polyethers such as polyoxyethylenes and polyoxypropylenes, polyacrylamides and polymethacrylamides such as poly(N-hydroxyalkyl) acrylamides and methacrylamides (e.g. poly N-(2-hydroxypropyl)methacrylamide), polyamides, polyurethanes and epoxy polymers.

In general the polymeric degradation products of biodegradable polymers containing units of formula (VI), by virtue of their water solubility, need not themselves be biodegradable; they may thus, for example, be polyvinylic or polyacrylic. The invention therefore includes the use of polymers containing units of formula (VI) in which A is a repeating unit of a polyolefin, for example ethylene or propylene. It will be appreciated that polymers of this type may be prepared by free radical polymerisation techniques with comparative ease and economy, in contrast with, for example, the more complex polypeptide synthesis techniques needed to prepare polymers such as those described in EP-A-0130935.

The nature and size of $R^1$, $R^2$ and $R^{3a}$ in units of formula (VI) will influence both the level to which polymers containing such units are rendered lipophilic and thus insolubilised with respect to water and the rate at which the side chain is biodegradably cleaved. Thus large and/or bulky groups will tend to reduce the rate of biodegradation through steric hindrance, while increasing the lipophilicity of the polymer. In one useful category of side chain $R^1$ and $R^2$ are each selected from hydrogen atoms and $C_{1-4}$ alkyl groups such as methyl, and $R^{3a}$ represents a lower alkyl group, containing at least 3 carbon atoms as in propyl and butyl groups; such side chains combine substantial degrees of lipophilicity and biodegradability.

It will be appreciated that e.g. linear polymers containing units of formula (VI) may exhibit enhanced processability parameters (e.g. solubility in organic solvents and melt processability) compared to crosslinked polymers, e.g. containing crosslinking groups incorporating units of formula (II). In this respect they may also be contrasted with the polymers described in EP-A-0130935, which have the potential disadvantage that the high level of hydrogen bonding exhibited by polypeptides will tend to cause them to have relatively high melting points, such that they may not be melt processable without undue degradation occuring.

Polymers containing units of formula (VI) may be prepared in any convenient way, for example by either (A) reaction of a preformed water-soluble polymer with a reagent serving to introduce the desired lipophilic methylene diester side chain, or (B) polymerisation of a functional monomer which carries the desired lipophilic methylene diester side chain.

Process (A) may be effected by, for example, reaction of a polymer having pendant alcoholic hydroxyl groups (e.g. polyvinyl alcohol, a polyhydroxyalkyl acrytate or methacrylate or a polysaccharide) with a compound of formula (IX)

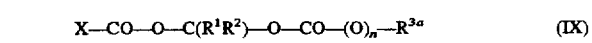

X—CO—O—C($R^1R^2$)—O—CO—(O)$_n$—$R^{3a}$    (IX)

(where $R^1$, $R^2$, $R^{3a}$ and n are as hereinbefore defined and X represents a leaving group such as a halogen atom, e.g. fluorine, chlorine, bromine or iodine). Reagents of formula (IX) may, for example, be prepared as described by Folkmann and Lund, *Synthesis* 1990, 1159. Such reactions, which will yield polymers containing units of formula (VI) in which m is 1, are conveniently effected in solution, for example in a solvent such as tetrahydrofuran, in the presence of a weakly nucleophilic base such as pyridine. A catalytic amount of a tertiary amine such as 4-dimethylaminopyridine may also be employed. The number of polymer hydroxyl groups which are reacted to form the desired lipophilic methylene diester groups may be controlled by appropriate choice of factors such as reagent quantities and reaction time and temperatures to affect the final hydrophilic-lipophilic balance of the lipophilised polymer. The product may be purified by standard techniques such as solvent extraction and/or dissolution/reprecipitation and/or flash chromatography.

Alternatively, process (A) may be effected by reaction of a polymer having pendant carboxyl groups (e.g. polyacrylic acid, polymethacrylic acid or a water-soluble peptide) with a compound of formula (X)

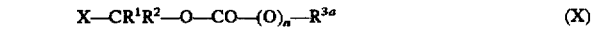

X—C$R^1R^2$—O—CO—(O)$_n$—$R^{3a}$    (X)

(where $R^1,R^2,R^{3a}$, X and n are as hereinbefore defined). Such reactions, which will yield polymers containing units of formula (VI) in which m is zero, are conveniently effected in solution, for example in a solvent such as N,N-dimethylformamide, in the presence of a strong base, for example an alkali metal alkoxide such as potassium t-butoxide. A catalytic amount of a crown ether such as 18-crown-6 may also be employed. Again the hydrophilic-lipophilic balance of the polymer product can be controlled by appropriate selection of reaction parameters to determine the number of carboxyl groups which are reacted, and the product may be purified by conventional techniques.

Reagents of formula (X) may be prepared by, for example, reaction of an aldehyde or ketone of formula $R^1$—CO—$R^2$ with an acid halide or haloformate ester of formula $R^{3a}$—(O)$_n$—CO—X, e.g. in the presence of a catalyst such as zinc chloride or pyridine.

Process (A) may also be effected by, for example, reaction of a polymer carrying functional groups such as epoxy groups with a reagent containing the desired lipophilic methylene diester grouping and having a terminal grouping reactive with such functional groups; terminal groups reactive with epoxy groups include amino, hydroxyl and carboxy groups. Similarly, the latter groups may be present in the initial polymer and the reagent may carry a terminal epoxy group.

Where the products are for intravenous use it is generally preferred that polymer starting materials employed in process (A) have a molecular weight of not more than about 40,000. Where the products are for other applications the molecular weight need not be critical.

Process (B) may be effected using any monomers which can be polymerised or copolymerised to form non-crosslinked polymers and which possess one or more substituents which do not participate in the polymerisation and which may be derivatised prior to polymerisation to introduce the desired lipophilic methylene diester grouping. Free radical, condensation and ionic polymerisation techniques may be employed.

Free radical polymerisation may, for example, be effected using carboxy group-containing monomers such as acrylic acid or methacrylic acid derivatised by reaction with a compound of formula (X) or by using hydroxyl group-containing monomers such as 2-hydroxyethyl acrylate or N-(2-hydroxypropyl)methacrylamide derivatised by reaction with a compound of formula (IX). Alternatively hydroxyl group-containing monomers may be reacted with a compound of formula (XI)

$$X-CO-O-C(R^1R^2)-X \quad (XI)$$

(where $R^1$, $R^2$ and X are as hereinbefore defined) and the resulting product reacted with an appropriate salt of a carboxylic acid $R^{3a}$-COOH.

Free radical polymerisation may also be effected using vinyl carbonate esters of formula (XII)

$$CH_2=CH-O-CO-O-C(R^1R^2)-O-CO-(O)_n-R^{3a} \quad (XII)$$

(where n, $R^1$, $R^2$ and $R^{3a}$ are as defined above). Such monomers, for example having n=0, may be prepared by reaction of vinyl chloroformate with an aldehyde or ketone $R^1R^2C=0$ in the presence of a catalytic amount of, for example, pyridine or a Lewis acid, to give an optionally substituted chloromethyl vinyl carbonate of formula (XIII)

$$CH_2=CH-O-CO-O-C(R^1R^2)-Cl \quad (XIII)$$

(where $R^1$ and $R^2$ are as defined above), followed by reaction with e.g. an appropriate salt of a carboxylic acid $R^{3a}$-COOH, preferably in the presence of a catalytic amount of a suitable crown ether. It will be appreciated that compounds (XII) may formally be regarded as "vinyl alcohol" derivatised by a compound of formula (IX). Polymers derived therefrom should accordingly be enzymatically biodegradable to polyvinyl alcohol.

Conventional bulk, solution, emulsion and suspension polymerisation techniques may be employed. The molecular weight of the polymer product, which for intravenous use preferably should not exceed about 40,000, may be controlled by the use of chain transfer agents such as mercaptans, from which the growing polymer chain can abstract a proton leading to chain termination and formation of a sulphur radical which will initiate a new polymer chain; the molecular weight of the polymer will thus be governed by the type and concentration of the transfer agent.

Appropriate vinyl monomers, e.g. having a carbonyl group adjacent to the vinyl group, as in acrylic or methacrylic esters, for example prepared as described above, may also be subjected to ionic polymerisation techniques, both anionic and cationic; such techniques are particularly suited to the production of well-defined molecular weight polymer, especially comparatively low molecular weight materials.

Condensation polymerisation may be effected using a wide range of appropriately functionalised monomers, examples of which may be represented by formulae (XIV) and (XV)

(XIV)

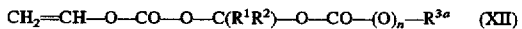
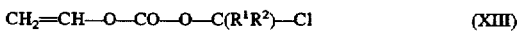

(XV)

(where $R^1$, $R^2$, $R^{3a}$, m and n are as hereinbefore defined, Y is a reactive grouping such as carboxy, hydroxyl or an epoxy group such as 2,3-epoxypropyloxy, and a, b and c may each be zero or a small integer such as 1,2 or 3). In formula (XV) the groups $R^1$, $R^2$ and $R^3$ and m and n may be the same or different in the two side chains. Such monomers may be employed in conventional condensation reactions with, as appropriate, reagents such as dicarboxylic acids, dialcohols, diamines, di(acid chlorides), diisocyanates and bisepoxy compounds to yield polymers such as polyesters, polyamides, polyurethanes and epoxy polymers. The molecular weight of the polymer product may be controlled by selection of appropriate reaction times, temperatures etc and/or by use of monofunctional chain terminators.

Where appropriate, the polymers may be prepared using emulsion polymerisation techniques; this may be of particular value where, for example, it is desired to prepare the polymers in the form of monodisperse particles. Methods of emulsion polymerisation to produce particles, especially monodisperse particles, are described in EP-A-0003905, EP-A-0091453, EP-A-0010986 and EP-A-0106873.

Polymers used in contrast agents according to the invention may advantageously be of relatively low molecular weight, e.g. not exceeding 40,000, since this may aid both biodegradation and dispersal of the degradation products. Accordingly the term "polymer" as used herein in relation to the invention should be understood to include low molecular weight materials such as oligomers.

It will be appreciated that since the polymers are to be used for medical purposes they must form non-toxic, physiologically acceptable degradation products; the groups $R^1$, $R^2$, $R^3$ and $R^{3a}$ in units of formulae (III) and (VI) should therefore be selected with this requirement and the need for the degradation products to be readily dispersible in mind. Carbon dioxide liberated by cleavage of carbonate ester groupings will normally be physiologically acceptable.

The contrast agents of the invention may be used in a variety of diagnostic imaging techniques, including ultrasound, MR and X-ray imaging. Their use in diagnostic ultrasonic imaging and in MR imaging, e.g. as susceptibility contrast agents, constitute preferred features of the invention.

Any biocompatible gas may be employed in the contrast agents of the invention, for example air, nitrogen, oxygen, hydrogen, nitrous oxide, carbon dioxide, helium, argon, sulphur hexafluoride and low molecular weight optionally fluorinated hydrocarbons such as methane, acetylene or carbon tetrafluoride, and perfluoroalkanes such as perfluorobutane or perfluoropentane. The gas may be free within the microbubble or may be trapped or entrained within a containing substance. The term "gas" as used herein includes any substances in gaseous form at 37° C.

Gas precursors include carbonates and bicarbonates, e.g. sodium or ammonium bicarbonate and aminomalonate esters.

For ultrasonic applications such as echocardiography, in order to permit free passage through the pulmonary system and to achieve resonance with the preferred imaging frequency of about 0.1–15 MHz, it may be convenient to employ microbubbles having an average size of 0.1–10 μm, e.g. 1–7 μm. Substantially larger bubbles, e.g. with average sizes of up to 500 μm, may however be useful in other applications, for example gastrointestinal imaging or investigations of the uterus or Fallopian tubes.

If desired the microbubbles may incorporate particulate stabilisers, for example amphiphiles and inorganic materials such as silica or iron oxide which are only partially wetted by the solvent system employed, e.g. having a particle size of 1–500 nm. Colloidal silica having a particle size of 5–50 nm may advantageously be employed for this purpose.

The contrast agents of the invention may incorporate additives such as emulsifying agents and/or coating agents, for example to modify their stability, dispersibility, aggregation tendencies, biological properties etc., or to modify the flexibility and/or polarity of the membrane. Representative additives include fatty acids (e.g. straight chain saturated or unsaturated fatty acids, for example containing 10–20 carbon atoms) and carbohydrate and triglyceride esters thereof; proteins such as gelatin or, more preferably, human serum albumin; phospholipids, e.g. lecithin; polysaccharides such as starch, modified (e.g. lipophilised) starch or gum arabic; and surface active polymers such as polyvinyl alcohols, polyethylene glycols and block copolymers (including extended polymers), for example poly(oxyethylene)-poly(oxypropylene)-poly(oxyethylene) block copolymers such as Pluronics.

Where block copolymer (including extended polymer) surfactants are employed, these may contain biodegradable linkages of formula (II) as hereinbefore defined.

The presence in such block copolymers of units of formula (II) in which $R^1$ and $R^2$ are selected from hydrogen atoms and methyl groups, e.g. in which $R^1$ represents a hydrogen atom and $R^2$ represents a methyl group may be advantageous; it may also be advantageous to select units in which m and n are zero.

The block copolymer surfactant may comprise two or more blocks of differing lyophilicity, for example in linear di-block, tri-block or multi-block arrays, e.g. of the type A-B, A-B-A, B-A-B or A-B-A-B-A where A and B are polymer blocks of differing lyophilicity, preferably being hydrophilic and hydrophobic blocks respectively. Branched structures, e.g. of the type

and macrocyclic structures, e.g. of the type

may also be employed.

Hydrophilic blocks in such block copolymer surfactants may, for example, be derived from polymers such as polysaccharides, polyalcohols (e.g. polyvinyl alcohol), polyvinylpyrrolidones, polyethylene glycols and poly (amino acids). Polymers such as polyorthoesters, polyacetals, polyanhydrides, polyglycolic acids, poly(meth) acrylic acids and derivatives such as esters thereof, substituted as necessary by hydrophilic groups, may also be useful. The hydrophilic blocks may advantageously consist essentially of polyethylene glycol units.

Hydrophobic blocks in such block copolymer surfactants may, for example, be derived from oil-soluble condensation, ionic and free-radical generated polymers, for example poly(meth)acrylate esters, polyorthoesters, vinylic and styrenic polymers, polyacetals, polyanhydrides, polyglycolic acids and ethers and esters thereof, and polylactic acid/polyglycolic acid copolymers; such polymers may, for example, incorporate or be substituted with hydrophobic groups such as alkyl, aralkyl or aryl groups to increase their hydrophobicity. The hydrophobic blocks may advantageously comprise a polyester chain containing one or more long chain aliphatic groups (e.g. $C_{10-20}$ polymethylene groups) linked by and/or incorporating units of formula (II). Such hydrophilic blocks may be oligomeric or quasipolymeric, as in extended polymers, and as such may include monomeric groups, which may for example exhibit polymer characteristics (e.g. as a result of the presence of long chain units) while not stricly possessing a definable repeating unit.

A preferred class of block copolymer surfactants thus comprises copolymers containing polyethylene glycol units as the hydrophilic blocks and units of formula

(where g is as hereinbefore defined and $R^a$ and $R^b$ each represent valence bonds or linking groups such as carbonyl groups or diacid residues of formula —O—CO—$(CH_2)_n$—CO—O where h is as hereinbefore defined) in the hydrophobic part, as an extending moiety or as a moiety in an oligomeric or polymeric block.

The contrast agents of the invention may be prepared in a number of ways, generally by emulsion techniques which are known in the polymer art. Thus, for example, microencapsulation techniques for the preparation of microcapsules having a wall or membrane of polymeric material are described in literature such as "Microencapsulation and Related Drug Processes" by P. D. Deasy, Marcel Dekker Inc., New York (1984).

One useful method corresponds to the interfacial deposition technique described in the above-mentioned EP-A-0458745 and comprises dissolving or suspending the polymeric wall-forming material in a water-immiscible organic solvent (for example an aliphatic or cycloaliphatic hydrocarbon or perfluorocarbon, e.g. containing up to 10 carbon atoms, or an appropriate ether, ester or other lipophilic solvent), emulsifying (e.g. by high shear mixing) the resulting solution or suspension in an aqueous phase (preferably containing a surfactant to stabilise the resulting oil in water emulsion), and subsequently removing the organic phase (e.g. by evaporation or lyophilisation, preferably under an atmosphere of the gas which is desired to be incorporated) whereby the polymer forms a membrane at the interface between the aqueous and organic phases.

Representative solvents include heptane, toluene, xylene, camphene (e.g. (–)-camphene), limonene and naphthalene. Solvents such as camphene are of advantage in that they are biotolerated so that it is not necessary to remove all solvent residues from the contrast agent prior to administration; such high-melting solvents will also rapidly solidify when the emulsion is frozen prior to lyophilisation and may thus enhance the structural integrity of the microparticulate contrast agent thereby obtained.

The size of the microparticles/microballoons so formed can be controlled by adjusting the stirring speed during emulsification, faster stirring tending to yield smaller particles, and is also affected by the nature of any surfactant used.

Emulsifying and/or coating agents, e.g. as hereinbefore described, may conveniently be dispersed or dissolved in the aqueous phase of the emulsion, for example in amounts of 1–10% w/v relative to the aqueous phase.

The porosity of the membrane, and therefore its permeability to solvents, solutes and gases, may also be controlled, being dependent on the difference in boiling point between the volatile organic phase and the surrounding aqueous phase; thus the porosity of the membrane increases with increasing difference between the said boiling points.

Alternatively the polymer may be dissolved in an appropriate organic solvent (e.g. methylene dichloride, dimethyl sulphoxide, tetrahydrofuran or dimethylformamide) and then dispersed (e.g. using a high speed stirrer) in an aqueous phase (preferably containing a polymeric material such as polyvinyl alcohol or a poloxamer) so as to precipitate particulate polymeric material which may be collected and lyophilised to yield porous microparticulate polymer in accordance with the invention. Such techniques are described in the above-mentioned EP-A-0458079. Variants for the preparation of microparticles include injecting the organic polymer solution, preferably together with a physiologically acceptable stabiliser such as hydroxypropyl cellulose, into liquid nitrogen. Alternatively the polymer may be dissolved in an appropriate organic solvent (e.g. methylene chloride or tetrahydrofuran), followed by spray drying of the solution, or of an oil in water or water in oil emulsion of the organic polymer solution with an aqueous phase.

Microparticles in accordance with the invention may also be prepared using coacervation or double emulsion techniques, e.g. as described in the above-mentioned WO 91/12823. Thus, for example, an aqueous phase containing a water-soluble polymer (hereafter referred to as the "prepolymer") may be emulsified with a volatile organic solvent (e.g. an aliphatic or cycloaliphatic hydrocarbon or perfluorocarbon containing up to 10 carbon atoms) to form an oil in water emulsion. Addition of a coacervating agent (e.g. a dehydrating agent such as isopropanol or a salt such as sodium sulphate) induces concentration of the "prepolymer" around the oil droplets, whereupon a surfactant is desirably added to inhibit agglomeration of the microparticles, which are formed by crosslinking the prepolymer to introduce biodegradable units of formula (II), thereby generating water-insoluble porous polymer microparticles which may be dried by lyophilisation. Appropriate crosslinking techniques and reagents for crosslinking water-soluble "prepolymers" such as polyacrylamides are described in detail in our aforementioned International Application No. WO 92/04392.

The contrast agents of the invention may be stored and transported in dry form, in which condition they will normally be stable indefinitely, being mixed with an appropriate liquid carrier (e.g. sterile water for injection, physiological saline or phosphate buffer) prior to administration. In this way the concentration of the injected or otherwise administered contrast agent may be varied at will, depending on the precise nature of the application. They may also be stored in suspension in such carriers, especially, in the case of microballoons, when the porosity of the encapsulating polymer membrane is comparatively low, being substantially completely stable in aqueous media in the absence of esterase enzymes.

Polymers comprising repeating units of formula (III) wherein $R^1$ represents methyl, $R^2$ represents hydrogen, $R^3$ is —$(CH_2)_g$—O—CO—$(CH_2)_h$—CO—O—$(CH_2)_g$—(where g and h are as hereinbefore defined) and m and n are zero are themselves novel products and constitute a further feature of the invention. As well as being useful starting materials for preparing contrast agents according to the invention, such polymers may be of use as or in, for example, surgical implants such as sutures, soft tissue prostheses, sponges, films (e.g. artificial skin), wound dressings (e.g. hydrogel sheets), flexible sheet materials and articles such as containers formed therefrom, delayed release formulations for drugs and agricultural chemicals, particulate imaging agents or plasticisers.

The novel polymers may be prepared by any convenient method, for example by reaction of a reactive derivative such as a dihalide of a diacid of formula $HOOC.(CH_2)_h.COOH$ (where h is as hereinbefore defined) with a diol of formula $HO.(CH_2)_g.CO.O.CH(CH_3).O.CO.(CH_2)_g.OH$ (where g is as hereinbefore defined), e.g. in an appropriate organic solvent. The diol may itself be prepared by reacting an ethylidene halide such as the iodide with two moles of ω-hydroxyacid $HO.(CH_2)_g.COOH$ e.g. in the presence of a base.

Figure 1:
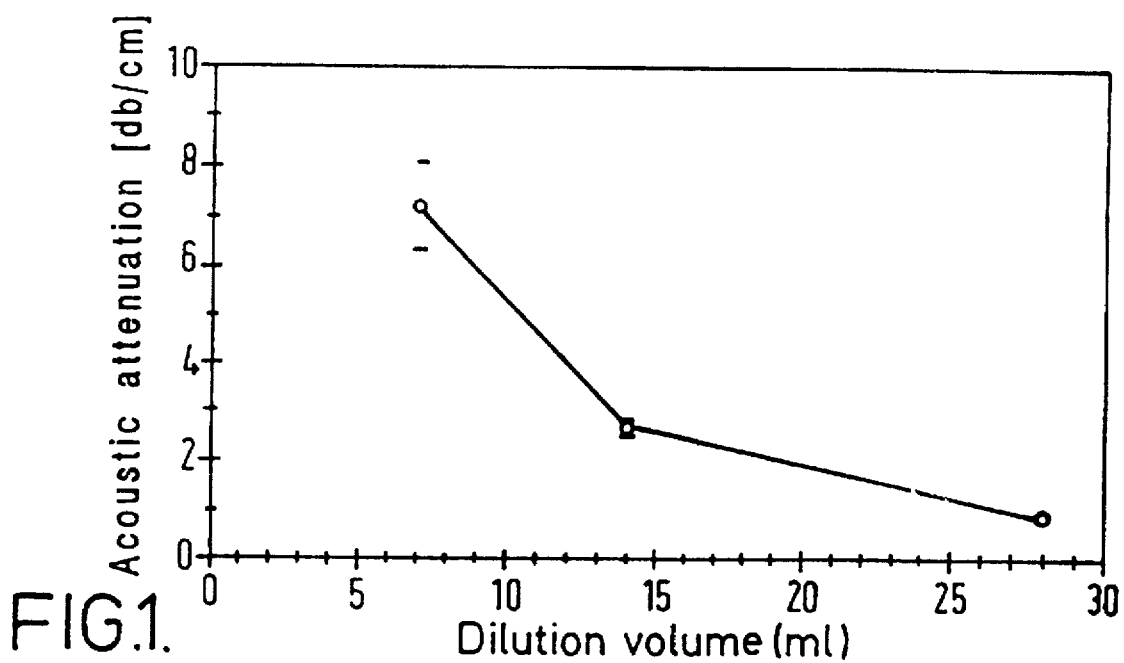
FIG. 1 is a graph showing the effects of concentration on the acoustic effect of polymer particles prepared in accordance with Example 3(a)
Figure 2:
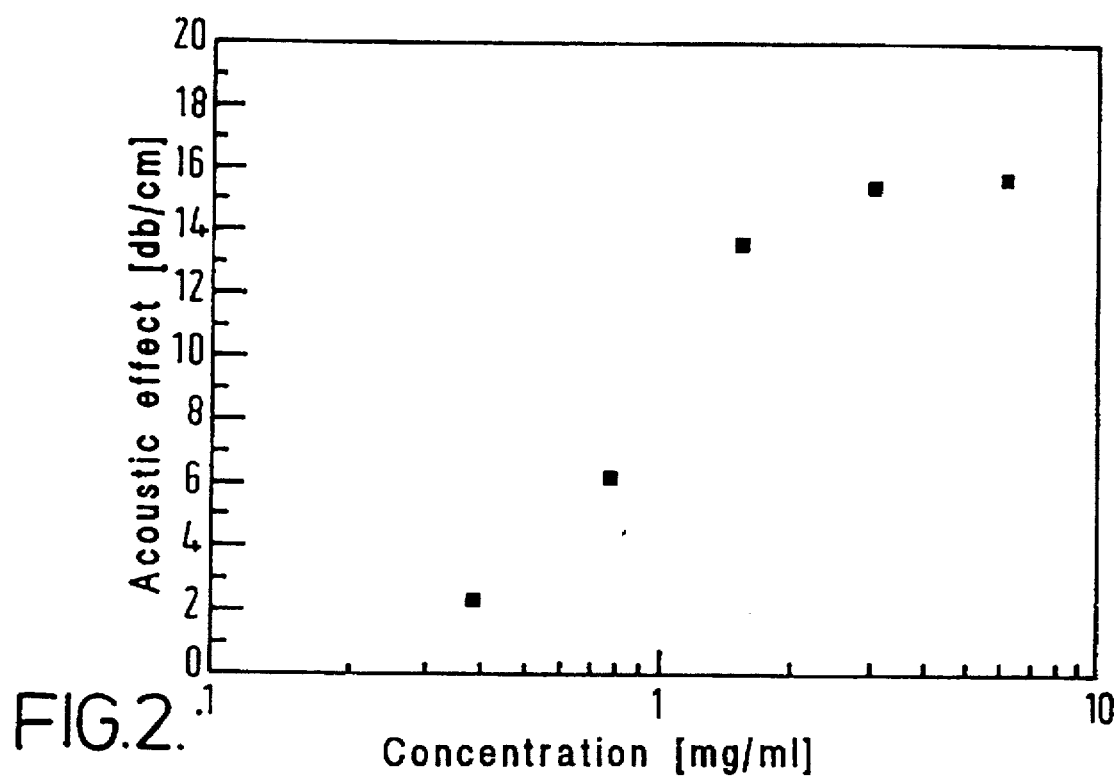
FIG. 2 is a graph showing the effects of concentration on the acoustic effect of polymer particles prepared in accordance with Example 3(b)
Figure 3:
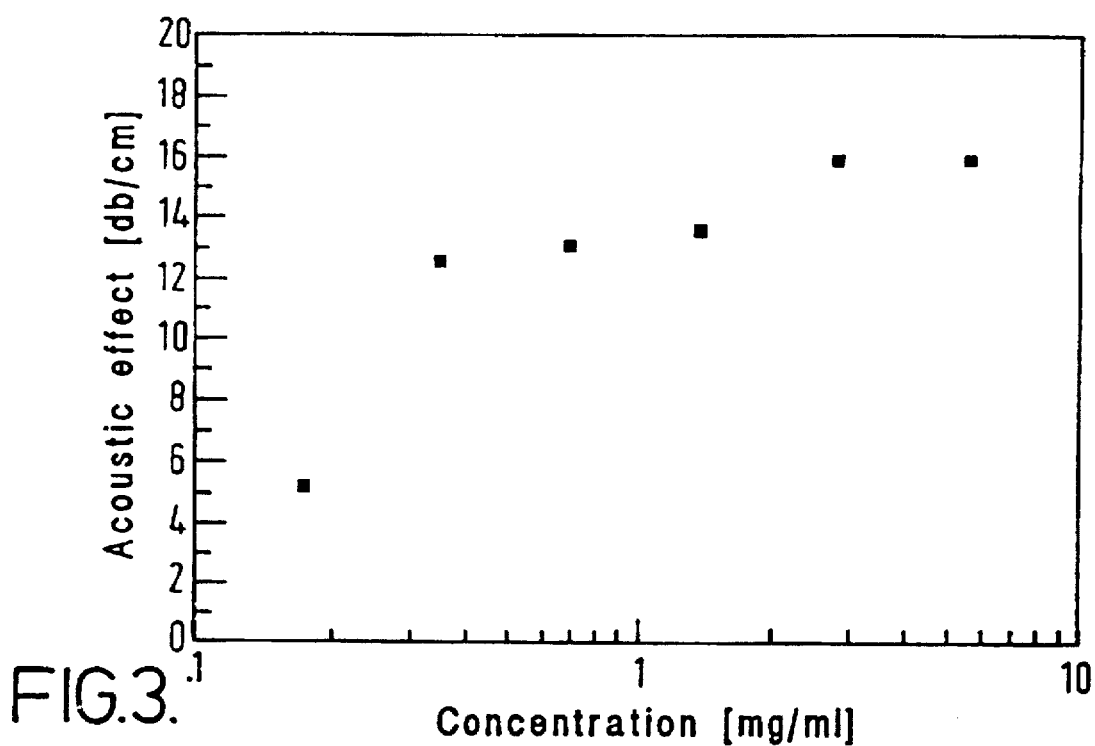
FIG. 3 is a graph showing the effects of concentration on the acoustic effect of polymer particles prepared in accordance with Example 3(c)
Figure 4:
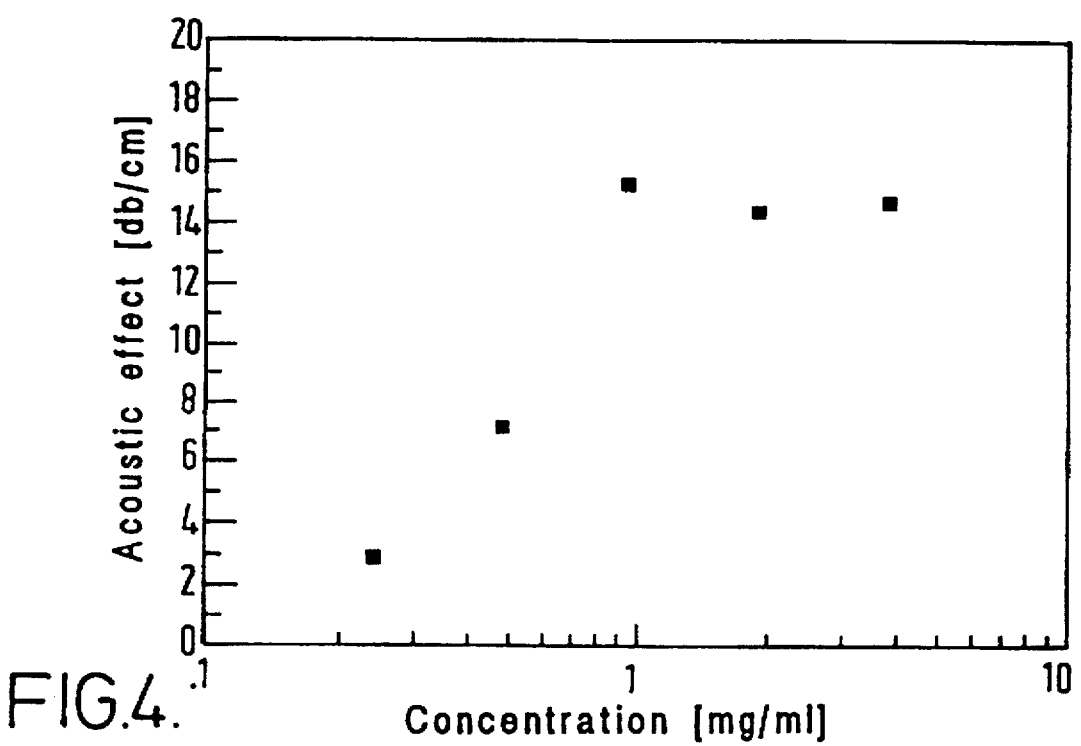
FIG. 4 is a graph showing the effects of concentration on the acoustic effect of polymer parricides prepared in accordance with Example 3(d)
Figure 5:
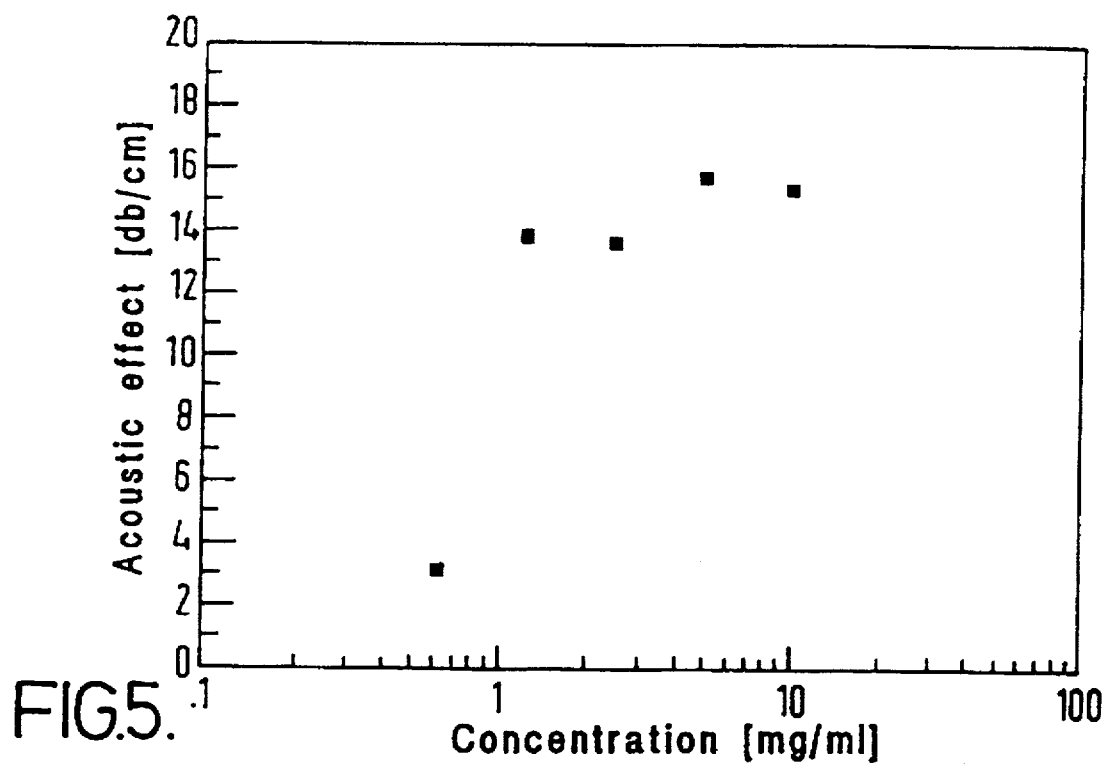
FIG. 5 is a graph showing the effects of concentration on the acoustic effect of polymer particles prepared in accordance with Example 3(e)
Figure 6:
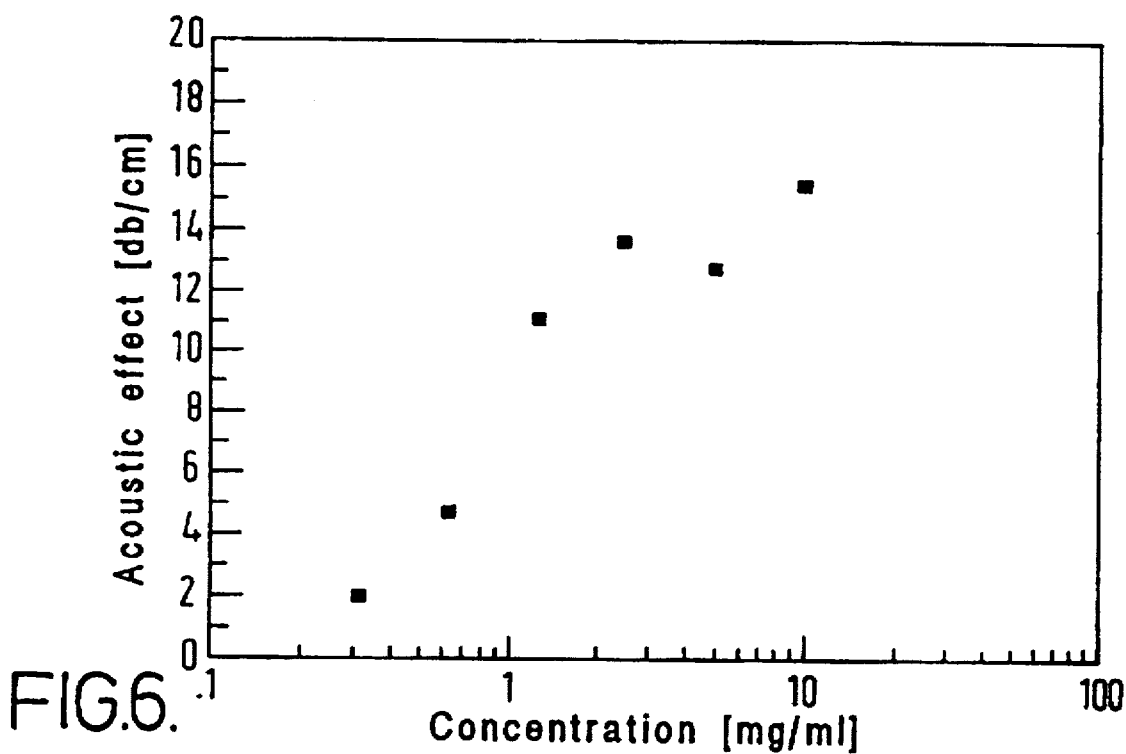
FIG. 6 is a graph showing the effects of concentration on the acoustic effect of polymer particles prepared in accordance with Example 3(f)
Figure 7:
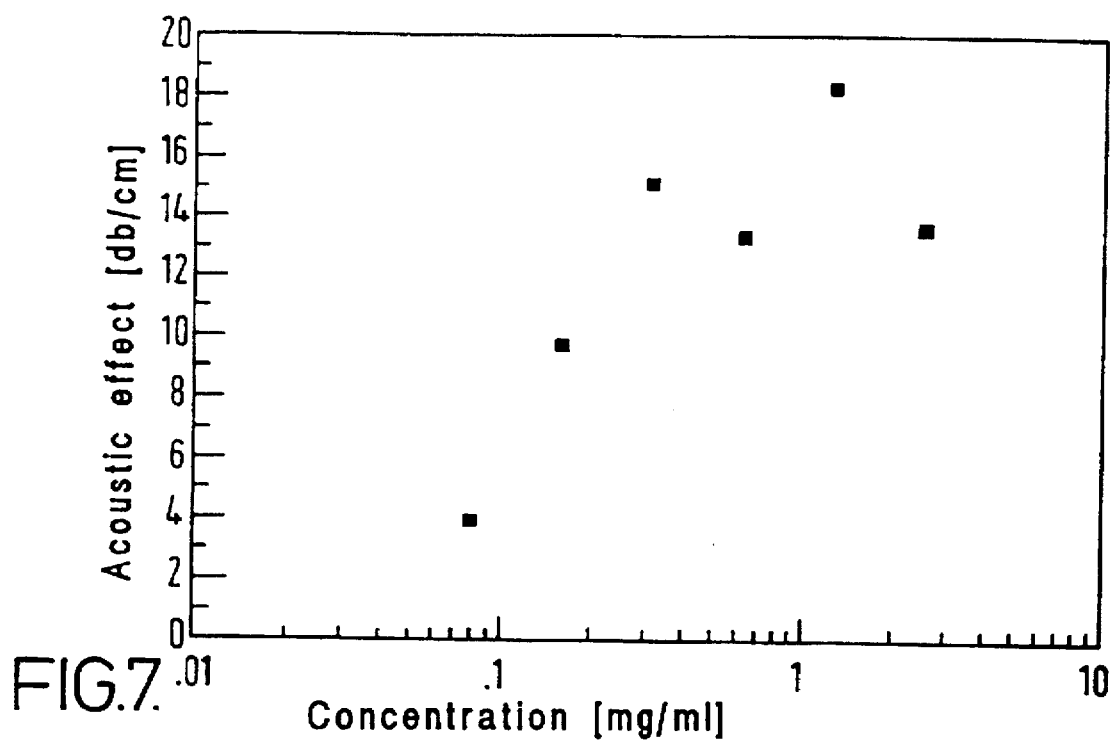
FIG. 7 is a graph showing the effects of concentration on the acoustic effect of polymer particles prepared in accordance with Example 3(g)
Figure 8:
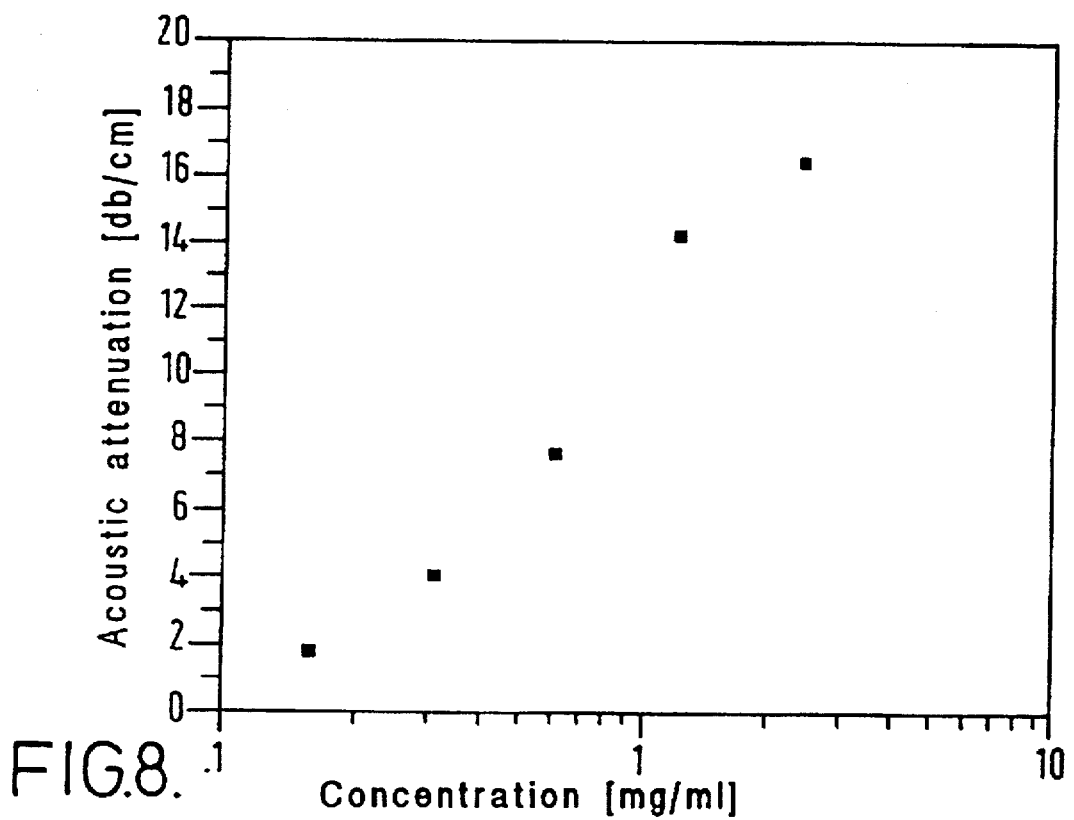
FIGS. 8 is a graph showing the effects of concentration on the acoustic effect of polymer particles prepared in accordance with Example 3(h)
Figure 9:
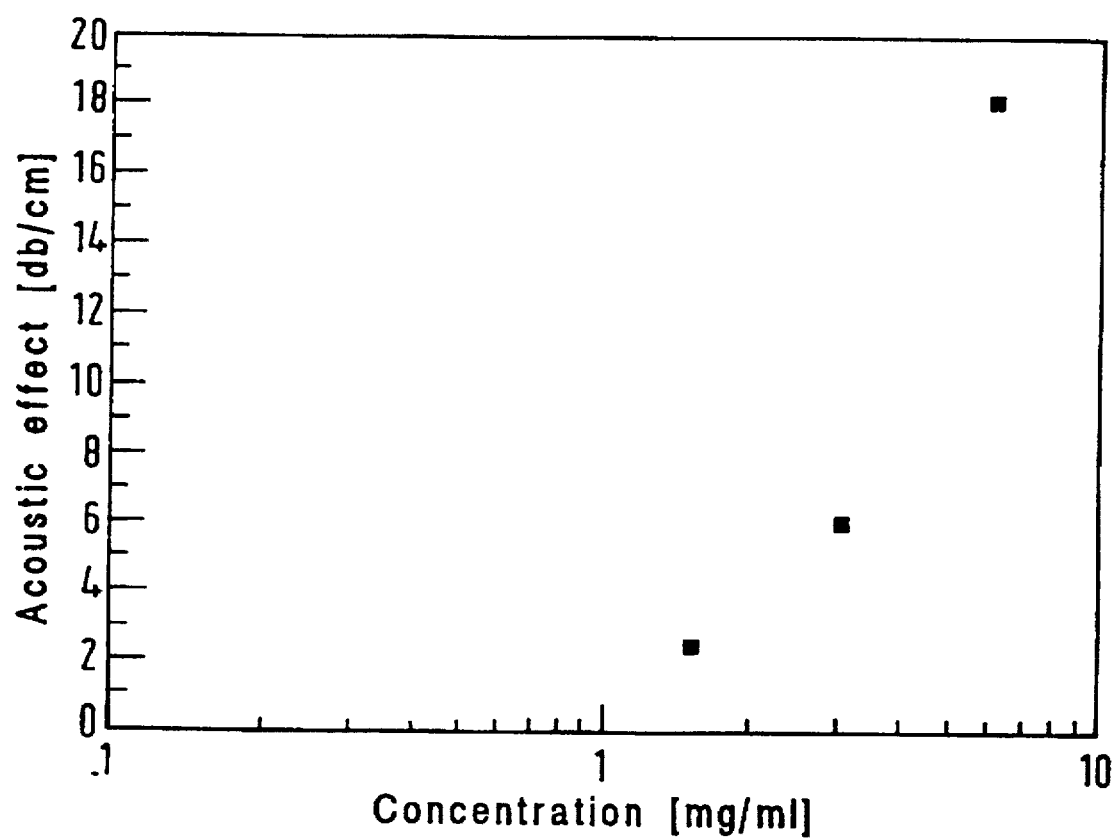
FIG. 9 is a graph showing the effects of concentration on the acoustic effect of polymer particles prepared in accordance with Example 3(i)

The following non-limitative Examples serve to illustrate the invention.

GENERAL

Methacrylic acid was distilled under high vacuum to remove the stabiliser.

2,2'Azobisisobutyronitrile (AIBN) thermal initiator was purified by recrystallisation from methanol.

All reactions were carried out under $N_2$.

Size Exclusion Chromatography (SEC):
Pump: Knauer HPLC pump 64
Detector: Knauer Differential refractometer
Columns: Polymer Laboratories PL gels columns in series Pore sizes $10^4$ Å, 500 Å, and 100Å, particle size 5 µm, length 30, 30 and 60 cm respectively.
Solvent: THF
Calibration: Polystyrene standards (Polymer Laboratories)
Flow rate marker: Toluene
Software: Polymer Laboratories GPC/SEC software version 5.10
Mw: weight average molecule weight
Mn: number average molecule weight
Mw/Mn: polydispersity
Mp: molecular weight at maximum detector height
List of abbreviations
Tg: glass transition temperature
TBA-OH: tetrabutylammonium hydroxide
TBA: tetrabutylammonium
AIBN: 2,2'-azobisisobutyronitrile
$SO_2Cl_2$: sulfuryl chloride
EtSCl: ethanesulfenyl chloride
DBU: 1,8-diazabicyclo[5.4.0]undec-7-ene(1,5-5)
$MgSO_4$: magnesium sulphate
THF: tetrahydrofuran
DMF: N,N-dimethylformamide
HSA: human serum albumin

EXAMPLE 1

Preparation of intermediates a) Methylene dimethacrylate

A solution of potassium hydroxide (1.00M, 40.00 ml) was added to methacrylic acid (3.44 g, 40.00 mmol) at 0° C. and the solution freeze dried for 16 hours. Dry dimethylformamide (230 ml) was added and the suspension heated to 60° C. under a dry nitrogen atmosphere. Diiodomethane (1.61 ml, 20.00 mmol) was added in two portions during 10 min. and the reaction mixture left for 4 days at 60° C. The solvent was removed under reduced pressure (0.05 mmHg), before diethyl ether (140 ml), saturated aqueous sodium hydrogen carbonate (50 ml) and water (50 ml) were added. The aqueous layer was extracted with diethyl ether (6×60 ml) and the combined ether-extracts washed with water (4×50 ml), dried ($MgSO_4$), and evaporated to give 2.63 g (72%) of the title compound.

$^1$H NMR (60 MHz, $CDCl_3$): δ1.97 (2×$CH_3$, m), 5.63 (2×H-C=, m), 5.88 ($CH_2$, s), 6.18 (2×H-C=, m). IR (film, $cm^{-1}$): 2987 (w), 2962 (w), 2930 (w), 1732 (str), 1638 (w), 1454 (w), 1315 (w), 1295 (w), 1158 (w), 1100 (str), 1012 (m), 989 (m).

b) Methylene bis(16-hydroxyhexadecanoate)

(i) 16-Triphenylmethoxyhexadecanoic acid

A solution of 16-hydroxyhexadecanoic acid (1.36 g, 5.00 mmol), triphenylmethyl chloride (1.53 g, 5.50 mmol), triethylamine (1.25 ml) and 4-dimethylaminopyridine (10.03 g, 0.25 mmol) was stirred overnight in dry dimethylformamide at ambient temperature under nitrogen. After 16 hours stirring, the brown cloudy solution was poured into icewater and extracted with dichloromethane (5×50 ml). The organic phases were washed with saturated ammonium chloride solution (2×100 ml), water (2×100 ml) and dried over $MgSO_4$. The solvent was removed under reduced pressure and the product purified by flash chromatography on a silica column with dichloromethane/methanol (20:1) as eluent to yield the title compound as a yellow oil (0.41 g).

$^{13}$C NMR (75 MHz, $CDCl_3$): δ24.9, 25.7, 26.3, 29.2, 29.5, 29.6, 29.7, 30 32.8, 34.1, 62.9, 63.7, 86.2, 144.5, 177.2.

MS (CI): 515 (M+H)

(ii) 16-Triphenylmethoxyhexadecanoic acid cesium salt

Aqueous cesium carbonate (1M, 0.16 ml) was added dropwise to a solution of 16-triphenylmethoxyhexadecanoic acid (0.16 g, 0.31 mmol) from Example 1b(i) above in tetrahydrofuran (10 ml) until the pH reached approximately 8, whereupon the solvent was removed under reduced pressure and the residue dried under vacuum for 2 hours. The oily semicrystalline residue was dispersed in dry dimethylformamide (10 ml) and evaporated to dryness in vacuo.

(iii) Methylene bis(16-triphenylmethoxyhexadecanoate)

Diiodomethane (0.04 g, 0.16 mmol) was added to a suspension of 16-triphenylmethoxyhexadecanoic acid cesium salt (0.31 mmol) from Example 1b(ii) above in dry dimethylformamide (10 ml). The reaction mixture was heated at 60° C. for 2 days under nitrogen. The solvent was removed in vacuo, and the product purified by flash chromatography on a 2×5 cm silica column with chloroform as eluent to yield the title compound as a brown oil (0.10 g).

$^{13}$C NMR (75 MHz, $CDCl_3$): δ24.6, 26.3, 29.0, 29.2, 29.4, 29.5, 29.6, 29.7, 30.0, 34.0, 63.7, 79.0, 86.2, 126.7, 127.2, 127.6, 127.9, 128.7, 144.5, 172.5.

(iv) Methylene bis(16-hydroxyhexadecanoate)

Methylene bis(16-triphenylmethoxyhexadecanoate) (0.07 g, 0.07 mmol) from Example 1b(iii) above was dissolved in glacial acetic acid (8 ml) and heated at 55° C. The reaction was monitored by TLC. After 10 hours the reaction mixture was poured onto ice, and the crude product was filtered, washed with aqueous sodium bicarbonate and water, and dried under reduced pressure. The product was purified by flash chromatography on a silica column with chloroform/methanol (20:1) as eluent to yield the title compound as a white solid.

$^1$H NMR (300 MHz, $CDCl_3$): δ1.2–1.4 (m, 44H), 1.5–1.6 (m, 8H) 2.35 (t, 4H), 3.64 (t, 4H), 5.75 (s, 2H).

c) Methylene bis(12-hydroxydodecanoate)

DBU (2.0 mmol) was added to a solution of 12-hydroxydodecanoic acid (2.0 mmol) in DMF (2 ml). The solution was stirred for 5 min before $CH_2I_2$ (1.0 mmol) was added, and the solution was stirred for 12 hours at 60° C. DMF was then removed under reduced pressure, and the residual material dissolved in $CHCl_3$ (50 ml), washed (10% $K_2CO_3$; 3×20 ml), dried ($MgSO_4$) and evaporated. The crude product was purified by flash chromatography on silica gel using $CHCl_3$/MeOH 95:5 for elution; yield 75%.

$^1$H NMR ($CDCl_3$): δ1.20–1.40 (m, 28H), 1.50–1.68 (m, 10H), 2.35 (t, J 7.5 Hz, 4H), 3.63 (t, J 6.6 Hz, 4H), 5.74 (s, 2H).

$^{13}$C NMR ($CDCl_3$): δ24.62, 25.75, 28.98, 29.19, 29.40, 29.42, 29.48, 29.56, 32.80, 33.99, 63.01, 79.06, 172.53. MS (EI): 445 (M+1, 100)

d) Methylene bis(10-hydroxydecanoate)

DBU (4.24 g, 0.027 mol) was added to 10-hydroxydecanoic acid (5.0 g, 0.027 mol) in DMF (100 ml). After 5 min. with stirring, diiodomethane (4.09 g, 0.014 mol) was added and the mixture was left stirring at room temperature for 3 days. DMF was evaporated under reduced pressure and the residue dissolved by adding chloroform (100 ml) and water (50 ml). After separating the phases the aqueous layer was extracted with chloroform (3×75 ml) and the combined organic phase was dried (MgSO$_4$). The solvent was removed under reduced pressure and flash chromatography gave 2.98 g (54.9%) of the title product.

$^1$H NMR (60 MHz, CDCl$_3$): δ1.30–1.80 (m, 28H, CH$_2$), 2.35 (m, 4H, CH$_2$CO), 3.65 (m, 6H, 2 X CH$_2$O+2 X OH), 5.75 (s, 2H, —OCH$_2$O—).

e) Bis(chlorocarbonyloxymethyl) terephthalate (i) Bis (ethylthiocarbonyloxymethyl) terephthalate Potassium tert. butoxide (3.24 g, 0.029 mol) was added to a solution of terephtalic acid (2.40 g, 0.014 mol) in DMF (100 ml). O-Chloromethyl S-ethyl carbonothioate$^1$ (4.50 g, 0.028 mol) was added to the resulting suspension. 18-crown-6 (0.23 g, 0.87 mmol) was then added and the reaction mixture was left with stirring at room temperature for 4 days. The reaction mixture was filtered and the solvent was removed under reduced pressure. The residue was purified by flash chromatography (silica/chloroform) to give 3.38 g (62%) of the title product.

$^1$H NMR (60 MHz, CDCl$_3$): δ1.30 (t, 6H, CH$_3$CH$_2$), 2.95 (q, 4H, CH$_3$CH$_2$), 5.80 (s, 4H, OCH$_2$O), 8.20 (s, 4H, Ph).

(ii) Bis(chlorocarbonyloxymethyl) terephthalate

SO$_2$Cl$_2$ (0.73 g, 0.0054 mol) was added to bis (ethylthiocarbonyloxymethyl) terephthalate (1.02 g, 0.0054 mol) from Example 1e(i) above at 0°–5 ° C. with stirring during 15 min. followed by stirring at room temperature for 45 min. Evaporation of EtSCl at room temperature and 0.1 mmHg gave light yellow crystals.

Yield: 0.80 g (90%)

$^1$H NMR (60 MHz, CDCl$_3$): δ5.76 (s, 4H, OCH$_2$O), 8.20 (s, 4H, Ph).

f) Methylene bis (4-hydroxymethylbenzoate)

DBU (9.90 g, 0.065 mol) was added to 4-hydroxymethylbenzoic acid (9.89 g, 0.065 mol) in DMF (325 ml). After 5 min. with stirring, diiodomethane (8.705 g, 0.035 mol) was added and the mixture was left with stirring at room temperature for 3 days. DMF was evaporated under reduced pressure and the residue dissolved by adding chloroform (100 ml) and water (50 ml). After separating the phases the aqueous layer was extracted with chloroform (3×75 ml) and the combined organic phase was dried (MgSO$_4$). The solvent was removed under reduced pressure to give 3.0 g (27%) of the title product.

$^1$H NMR (60 MHz, CDCl$_3$): δ4.7 (s, 4H, HO—CH$_2$—Ph), 6.2 (s, 2H, O—CH$_2$—O), 7.4–8.2 (m, 8H, Ph).

g)-k) General procedure for chloromethyl carbonates

To a solution of chloromethyl chloroformate and the stated alcohol in methylene chloride (200 ml), pyridine was added at 0° C. After 20 min at 0° C. and 21 hours at 25° C. the reaction mixture was washed with aqueous hydrochloric acid (1M, 10 ml), aqueous saturated sodium hydrogen carbonate (10 ml) and water (10 ml). The solvent was removed under reduced pressure after drying (MgSO$_4$), giving crude chloromethyl carbonate.

TABLE 1

| Example 1 | Chloromethyl-chloroformate g, mmol | Alcohol, ROH R, (g, mmol) | Pyridine g, mmol |
|---|---|---|---|
| g | 25.01, 194 | CH$_3$, (5.64, 176) | 15.52, 194 |
| h | 15.81, 124 | CH$_3$CH$_2$, (5.20, 113) | 9.91, 124 |
| i | 14.20, 111 | CH$_3$(CH$_2$)$_3$, (8.10, 109) | 8.90, 113 |
| j | 20.01, 155 | CH$_3$(CH$_2$)$_9$, (22.25, 139) | 12.54, 157 |
| k | 20.02, 155 | PhCH$_2$, (15.23, 141) | 12.54, 157 | g) Methyl chloromethyl carbonate.

The compound was obtained from chloromethyl chloroformate and methanol.

$^1$H NMR (60 MHz, CDCl$_3$): δ3.98 (s, 3H, OCH$_3$), 5.85 (s, H, CH$_2$Cl).

h) Ethyl chloromethyl carbonate

The compound was obtained from chloromethyl chloroformate and ethanol.

$^1$H NMR (60 MHz, CDCl$_3$): δ1.25 (t, 3H, CH$_3$), 4.25 (q, H, CH$_2$), 5.70 (s, 2M, OCH$_2$Cl).

i) Butyl chloromethyl carbonate

The compound was obtained from chloromethyl chloroformate and butanol.

$^1$H NMR (60 MHz, CDCl$_3$): δ0.86 (m, 3H, CH$_3$CH$_2$), 1.40 (m, 4H, CH$_2$CH$_2$), 4.15 (t, 2H, CH$_2$—O), 5.63 (s, 2H, OCH$_2$Cl).

j) Decyl chloromethyl carbonate

The compound was obtained from chloromethyl chloroformate and decyl alcohol.

$^1$H NMR (60 MHz, CDCl$_3$): δ0.90–1.50 (m, 19H, CH$_3$ and CH$_2$), 4.20 (m, 2H, CH$_2$O), 5.75 (s, 2H, OCH$_2$Cl).

k) Benzyl chloromethyl carbonate

The compound was obtained from chloromethyl chloroformate and benzyl alcohol.

$^1$H NMR (60 MHz, CDCl$_3$): δ5.20 (s, 2H, PhCH$_2$O), 5.70 (s, 2H, ClCH$_2$O), 7.32 (s, 5H, Ph).

l)-p) General procedure for methacryloyloxymethyl carbonates

Potassium tert. butoxide was added to a solution of methacrylic acid in DMF (200 ml). Chloromethyl carbonate from Example 1g–k above was added to the resulting suspension. 18-crown-6 was then added and the reaction mixture was left with stirring at room temperature for 24 hours. The reaction mixture was filtered and the solvent was removed under reduced pressure. The residue was dissolved in chloroform (30 ml) and washed with saturated aqueous sodium hydrogen carbonate (10 ml) and water (20 ml). The organic phase was dried (MgSO$_4$) and the solvent removed under reduced pressure.

TABLE 2

| Example | Compound from Ex. 1, (g, mmol) | Potassium methacrylate (g, mmol) | 18-crown-6 (g, mmol) | DMF (ml) |
|---|---|---|---|---|
| 1 | g, (9.67, 78) | 8.71, 78 | 1.01, 38 | 350 |
| m | h, (8.04, 60) | 6.73, 60 | 0.6, 23 | 300 |
| n | i, (30.61, 122) | 13.67, 122 | 2.5, 94 | 600 |
| o | j, (30.61, 122) | 13.67, 122 | 2.5, 94 | 600 |
| p | k, (22.01, 110) | 13.64, 110 | 1.5, 57 | 550 | l) Methyl methacryloyloxymethyl carbonate

The compound was obtained from methyl chloromethyl carbonate and potassium methacrylate.

IR (KBr): 1772 (C=O, str.), 1737 (C=O, str.), 1635 (C=C, str.) cm⁻¹

$^1$H NMR (300 MHz, CDCl$_3$): δ1.91 (s, 3H, CH$_3$C=), 3.79 (s, 3H, CH$_3$O), 5.64 (m, 1H, CH$_2$=), 5.80 (s, 2H, —OCH$_2$O—), 6.16 (m, 1H, CH$_2$=).

$^{13}$C NMR (75 MHz, CDCl$_3$): δ17.95 (CH$_3$C=), 55.13 (CH$_3$O), 82.18 (—OCH$_2$O—), 127.52 (CH$_2$=), 135.02 (C=), 154.44 (C=O), 165.46 (C=O).

m) Ethyl methacryloyloxymethyl carbonate

The compound was obtained from ethyl chloromethyl carbonate and potassium methacrylate.

IR (KBr): 1772 (C=O, str), 1736 (C=O, str.), 1635 (C=C, str) cm⁻¹

$^1$H NMR (300 MHz, CDCl$_3$): δ1.27 (t, 3H, CH$_3$), 1.92 (s, 3H, CH$_3$C=), 4.23 (q, 2H, CH$_2$), 5.66 (m, 1H, CH$_2$=), 5.80 (s, 2H, —OCH$_2$O—), 6.20 (m, 1H, CH$_2$=).

$^{13}$C NMR (75 MHz, CDCl$_3$): δ15.70 (CH$_3$CH$_2$), 19.60 (CH$_3$C=), 65.72 (CH$_2$O), 83.05 (—OH$_2$O—), 127.76 (CH$_2$=), 135.40 (C=), 153.82 (C=O), 165.42 (C=O).

n) Butyl methacryloyloxymethyl carbonate

The compound was obtained from butyl chloromethyl carbonate and potassium methacrylate.

IR (KBr): 1772 (C=O, str), 1736 (C=O, str.), 1635 (C=C, str) cm⁻¹

$^1$H NMR (300 MHz, CDCl$_3$): δ0.99 (t, 3H, CH$_3$CH$_2$), 1.47 (m, 2H, CH$_2$CH$_2$), 1.72 (m, 2H, CH$_2$CH$_2$), 2.01 (s, 3H, CH$_3$C=), 4.25 (t, 2H, CH$_2$—O), 5.74 (m, 1H, CH$_2$=), 5.89 (s, 2H, —OCH$_2$O), 6.27 (m, 1H, CH$_2$=).

$^{13}$C NMR (75 MHz, CDCl$_3$): δ13.47 (CH$_3$CH$_2$), 17.97 (CH$_2$CH$_2$), 18.71 (CH$_3$C=), 30.36 (CH$_2$), 68.46 (CH$_2$O), 82.07 (—OCH$_2$O—), 127.46 (CH$_2$=), 135.05 (C=), 153.89 (C=O), 165.50 (C=O).

o) Decyl methacryloyloxymethyl carbonate

The compound was obtained from decyl chloromethyl carbonate and potassium methacrylate.

IR (KBr): 1772 (C=O, str.), 1763 (C=O, str.), 1635 (C=C, str.) cm⁻¹

$^1$H NMR (300 MHz, CDCl$_3$): δ0.90 (t, 3H, CH$_3$), 1.28 (m, 14H, CH$_2$), 1.72 (m, 2H, CH$_2$), 1.99 (s, 3H, CH$_3$C=), 4.21 (t, 2H, CH$_2$O), 5.70 (m, 1H, CH$_2$=), 5.86 (s, 3H, —OCH$_2$O—), 6.24 (m, 1H, CH$_2$=).

$^{13}$C NMR (75 MHz, CDCl$_3$): δ13.78 (CH$_3$), 17.76 (CH$_3$C=), 22.76–31.55 (CH$_2$), 68.60 (CH$_2$O), 81.90 (—OCH$_2$O—), 127.28 (CH$_2$=), 134.86 (C=), 153.73 (C=O), 165.33 (C=O).

p) Benzyl methacryloyloxymethyl carbonate

The compound was obtained from benzyl chloromethyl carbonate and potassium methacrylate.

IR (KBr): 3077 (Ph), 1772 (C=O, str.), 1763 (C=O, str.), 1635 (C=C, str.) cm⁻¹

$^1$H NMR (300 MHz, CDCl$_3$): δ1.96 (s, 3H, CH$_3$C=), 5.22 (s, 2H, CH$_2$O), 5.70 (m, 1H, CH$_2$=), 5.87 (s, 3H, —OCH$_2$O—), 6.22 (m, 1H, CH$_2$=) 7.39 (s, 5H, Ph).

$^{13}$C NMR (75 MHz, CDCl$_3$): δ17.96 (CH$_3$C=), 69.91 (CH$_2$O), 82.03 (—OCH$_2$O—), 127.41 (CH$_2$=), 128.32 (Ph), 134.78 (C=), 153.58 (C=O), 165.28 (C=O).

q) Ethyl 1-methacryloyloxyethyl carbonate (i) Ethyl chloroethyl carbonate

To a solution of chloroethyl chloroformate (23.16 g, 0.162 mol) and ethanol (7.45 g, 0.162 mol) in methylene chloride (200 ml), pyridine (12.82 g, 0.162 mol) was added at 0° C. After 10 min at 0° C. and 21 hours at 25° C. the reaction mixture was washed with aqueous hydrochloric acid (100 ml), aqueous saturated sodium hydrogen carbonate (100 ml) and water (100 ml). The solvent was removed under reduced pressure after drying (MgSO$_4$), giving 18.5 g (74%) of the intermediate ethyl chloroethyl carbonate as a crude product.

$^1$H NMR (60 MHz, CDCl$_3$): δ1.30 (t, 3H, CH$_3$), 1.85 (d, 3H, CH$_3$CH), 4.25 (q, 2H, CH$_2$), 6.45 (q, 1H, CH).

(ii) Ethyl 1-methacryloyloxyethyl carbonate

Potassium tert. butoxide (3.70 g, 0.033 mol ) was added to a solution of methacrylic acid (2.84 g, 0.033 mol) in DMF (100 ml). Ethyl chloroethyl carbonate (5.08 g, 0.033 mol) from Example 1q(i) above was added to the resulting suspension. 18-crown-6 (0.61 g, 2.3 mmol) was then added and the reaction mixture was left with stirring at room temperature for 3 days. The reaction mixture was filtered and the solvent was removed under reduced pressure. The residue was dissolved in chloroform (100 ml) and washed with saturated aqueous sodium hydrogen carbonate (50 ml) and water (50 ml). The organic phase was dried (MgSO$_4$) and the solvent removed under reduced pressure. Flash chromatography gave 2.50 g (38%) of the title product. (Adjusted for recovered starting material the yield was 75%).

$^1$H NMR (60 MHz, CDCl$_3$): δ1.30 (t, 3H, CH$_3$CH$_2$), 1.60 (d, 3H, CH$_3$CH), 2.00 (s, 3H, CH$_3$C=), 4.20 (q, 2H, CH$_2$), 5.70 (m, 1H, CH$_2$=), 6.25 (q, 1H, —OCH(CH$_3$)O—), 6.90 (m, 1H, CH$_2$=).

r) Methacryloyloxymethyl benzoate

Potassium tert. butoxide (10.0 g, 0.090 mol) was added to a solution of methacrylic acid (7.75 g, 0.090 mol) in DMF (300 ml). Chloromethyl benzoate[2] (15.0 g, 0.088 mol) was added to the resulting suspension. 18-crown-6 (1.8 g, 6.9 mmol) was then added and the reaction mixture was left with stirring at room temperature for 2 days. The reaction mixture was filtered and the solvent was removed under reduced pressure. The residue was dissolved in chloroform (100 ml) and washed with saturated aqueous sodium hydrogen carbonate (50 ml) and water (50 ml). The organic phase was dried (MgSO$_4$) and the solvent removed under reduced pressure. Flash chromatography gave 15.9 g (82%) of the title product.

$^1$H NMR (60 MHz, CDCl$_3$): δ2.00 (s, 3H, CH$_3$C=), 5.65 (m, 1H, CH$_2$=), 6.15 (s, 2H, —OCH$_2$O—), 6.35 (m, 1H, CH$_2$=), 7.50 (m, 3H, Ph), 8.05 (m, 2H, Ph).

s) N-(2-acetoxymethoxycarbonyloxypropyl) methacrylamide (i) N-(2-chloromethoxycarbonyloxypropyl) methacrylamide To a solution of N-(2-hydroxypropyl) methacrylamide[3] (2.86 g, 20 mmol), and pyridine (1.90 g, 24 mmol) in methylene chloride (100 ml), chloromethyl chloroformate (3.87 g, 30 mmol) in methylene chloride (120 ml) was added at 0° C. After 15 min at 0° C. and 24 hours at 25° C. the reaction mixture was washed with water (5×25 ml). The solvent was removed under reduced pressure after drying (MgSO$_4$). Flash chromatography (silicagel, chloroform) gave 3.30 g (70%) of the title product.

$^1$H NMR (60 MHz, CDCl$_3$): δ1.42 (d, 3H, CH$_3$—CH—O), 2.0 (m, 3H, CH$_3$C=), 3.2–4.0 (m, 2H, NH—CH$_2$—CH), 4.8–5.3 (m, 1H, CH$_3$—CH—O), 5.3 (m, 1H, CH$_2$=), 5.70 (m, 1H, CH$_2$=), 5.7 (s, 2H, CH$_2$Cl), 6.1–6.7 (br s, 1H, NH).

(ii) N-(2-acetoxymethoxycarbonyloxypropyl) methacrylamide

21

Method 1

A THF solution (30 ml) of TBA acetate (1.21 g, 4 mmol) prepared by freeze-drying an aqueous solution of equimolar TBA-OH and acetic acid, was added to a stirred solution of N-(2-chloromethoxycarbonyloxypropyl)methacrylamide (0.943, 4 mmol) from Example 1s(i) above in THF (10 ml) at room temperature. Following stirring for 5 days the solvent was removed under reduced pressure. The residue was dissolved in chloroform (50 ml) and washed with water (5×10 ml). The organic phase was dried (MgSO$_4$) and the solvent removed under reduced pressure. Flash chromatography (silicagel, hexane/ethyl acetate (3:4)) gave 0.486 g (47%) of the title product.

$^1$H NMR (60 MHz, CDCl$_3$): δ1.4 (d, 3H, CH$_3$—CH—O), 2.0 (s, 3H, CH$_3$C=), 2.2 (s, 3H, CH$_3$C=O), 3.2–4.0 (m, 2H, NH—CH$_2$—CH), 4.8–5.3 (m, 1H, CH$_3$—C=O), 5.3 (m, 1H, CH$_2$=), 5.70 (m, 1H, CH$_2$=), 5.8 (s, OCH$_2$O), 6.1–6.7 (br s, 1H, NH)

Method 2:

To a solution of N-(2-hydroxypropyl)-methacrylamide$^3$ (0.430 g, 3.0 mmol) and pyridine (0.285 g, 3.6 mmol) in methylene chloride (30 ml), acetoxymethyl chloroformate (0.500 g, 3.3 mmol) in methylene chloride (6 ml) was added at 0° C. After 10 min at 0° C. and 3 days at room temp. the reaction mixture was washed with water (100 ml). The solvent was removed under reduced pressure after drying (MgSO$_4$). Flash chromatography (silicagel, hexane/ethyl acetate (3:4)) gave 0.40 g (51%) of the title product.

NMR data were in good agreement with those above.

t) N-[2-(1-acetoxyethoxycarbonyloxy)propyl] methacrylamide

(i) N-[2-(1-chloroethoxycarbonyloxy)propyl] methacrylamide

To a solution of N-(2-hydroxypropyl)methacrylamide$^3$ (3.15 g, 22 mmol), and pyridine (2.088 g, 26.4 mmol) in methylene chloride (100 ml), 1-chloroethyl chloroformate (4.718 g, 33 mmol) in methylene chloride (20 ml) was added at 0° C. After 10 min at 0° C. and 5.5 hours at 25° C. the reaction mixture was washed with water (5×40 ml). The solvent was removed under reduced pressure after drying (MgSO$_4$) to give 4.84 g (88%) of the title product.

$^1$H NMR (60 MHz, CDCl$_3$): δ1.37 (d, 3H, CH$_2$—CH (CH$_3$)O—), 1.83 (d, 3H, CH$_3$—CH—Cl), 1.97 (m, 3H, CH$_3$C=), 3.3–3.6 (m, 2H, NH—CH$_2$—CH), 4.7–5.3 (m, 1H, CH$_2$—CH(CH$_3$)—O), 5.3 (m, 1H, CH$_2$=), 5.70 (m, 1H, CH$_2$=), 6.0–6.6 (m, 2H, NH+—Cl—CH—CH$_3$).

(ii) N-[2-(1-acetoxyethoxycarbonyloxy)propyl]-methacrylamide

A THF solution (100 ml) of TBA acetate (6.93 g, 23 mmol) prepared by freeze-drying an aqueous solution of equimolar TBA-OH and acetic acid, was added to a stirred solution of N-[2-(1-chloroethoxycarbonyloxy)propyl] methacrylamide (4.736 g, 19 mmol) from Example 1t(i) above in THF (100 ml) at room temperature. Following stirring for 4 days the solvent was removed under reduced pressure. The residue was dissolved in chloroform (100 ml) and washed with water ( 5×20 ml ). The organic phase was dried (MgSO$_4$ ) and the solvent removed under reduced pressure. Flash chromatography (silicagel, hexane/ethyl acetate (3:4)) gave 1.29 g (25%) of the title product.

$^1$H NMR (60 MHz, CDCl$_3$): δ1.3 (d, 3H, CH$_2$—CH(CH$_3$) O—), 1.5 (d, 3H, O—CH(CH$_3$)O), 2.0 (m, 3H, CH$_3$C=), 2.1 (s, 3H, CH$_3$C=O), 3.3–3.6 (m, 2H, NH—CH$_2$—CH), 4.7–5.3 (m, 1H, CH$_2$—CH(CH$_3$)—O), 5.4 (m, 1H, CH$_2$=), 5.7 (m, 1H, CH$_2$=), 6.1–6.6 (br s, 1H, NH), 6.6–6.9 (m, 1H, O—CH(CH$_3$)O)

22 u) Methyl 1-methacryloyloxyethyl carbonate

(i) Methyl 1-chloroethyl carbonate

To a solution of 1-chloroethyl chloroformate (35.74 g, 0.25 mol) and methanol (8.00 g, 0.25 mol) in methylene chloride (300 ml), pyridine (19.78 g, 0.25 mol) was added at 0° C. After 10 min at 0° C. and 2 days at 25° C. the reaction mixture was washed with aqueous hydrochloric acid (100 ml), aqueous saturated sodium hydrogen carbonate (100 ml) and water (100 ml). The solvent was removed under reduced pressure after drying (MgSO$_4$), giving 25.5 g (74%) of the intermediate methyl 1-chloroethyl carbonate as a crude product.

$^1$H NMR (60 MHz, CDCl$_3$): δ1.85 (d, 3H, CH$_3$CH), 3.80 (s,3H, CH$_3$O), 6.50 (q, 1H, CH).

(ii) Methyl 1-methacryloyloxyethyl carbonate

Potassium tert. butoxide (3.70 g, 0.033 mol ) was added to a solution of methacrylic acid (2.84 g, 0.033 mol) in DMF (100 ml). Methyl 1-chloroethyl carbonate (4.55 g, 0.033 mol) from Example 1u(i) above was added to the resulting suspension. 18-crown-6 (0.61 g, 2.3 mmol) was then added and the reaction mixture was left with stirring at room temperature for 3 days. The reaction mixture was filtered and the solvent was removed under reduced pressure. The residue was dissolved in chloroform (100 ml) and washed with saturated aqueous sodium hydrogen carbonate (50 ml) and water (50 ml). The organic phase was dried (MgSO$_4$) and the solvent removed under reduced pressure. Flash chromatography gave 4.46 g (72%) of the title product.

$^1$H NMR (60 MHz, CDCl$_3$): δ1.65 (d, 3H, CH$_3$CH), 2.00 (s, 3H, CH$_3$C=), 3.90 (s, 3H, CH$_3$O), 5.65 (m, 1H, CH$_2$=), 6.25 (m, 1H, CH$_2$=), 6.90 (q, 1H, CHCH$_3$).

v) Ethylene di(chloromethyl carbonate)

Chloromethyl chloroformate (19.12 g, 148.5 mmol) was added to an ice-cooled (0° C.) solution of ethylene glycol (2.8 ml, 50 mmol) in CH$_2$Cl$_2$(200 ml). Pyridine (8.70 g, 110 mmol) was then added and the reaction mixture was left with stirring for 15 min. at 0° C. and 6 hours at room temperature. The reaction mixture was washed with HCl (1M, 100 ml), NaHCO$_3$ (aq, saturated, 100 ml) and water (100 ml) and dried (MgSO$_4$). The solvent was evaporated and gave 11.88 g (96.2%) of the title product.

$^1$H NMR (60 MHz, CDCl$_3$): δ4.48 (m, 4H, OCH$_2$CH$_2$O), 5.75 (s, 4H, OCH$_2$Cl).

w) Acetoxymethyl chloroformate

(i) O-Acetoxymethyl S-ethyl carbonothioate

O-Chloromethyl S-ethyl carbonothioate$^1$ (4.50 g, 0.028 mol) in DMF (20 ml) was added to a solution of potassium acetate (2.74 g, 0.028 mol) in THF (100 ml). 18-crown-6 (0.22. g, 0.84 mmol) was then added and the reaction mixture was left with stirring at room temperature for 3 days. The reaction mixture was filtered and the solvent was removed under reduced pressure. The residue was purified by flash chromatography (silicagel, chloroform) to give 4.23 g (85%) of the title product.

$^1$H NMR (60 MHz, CDCl$_3$): δ1.30 (t, 3H, CH$_3$CH$_2$), 2.20 (s, 3H, CH$_3$C=O), 2.95 (q, 2H, CH$_2$CH$_3$), 5.80 (s, 2H, OCH$_2$O).

(ii) Acetoxymethyl chloroformate

SO$_2$Cl$_2$ (2.43 g, 0.018 mol) was added to O-Acetoxymethyl S-ethyl carbonothioate (Example 1w (i), 3.15 g, 0.018 mol) at 0°–5 ° C. with stirring during 15 min. followed by stirring at room temperature for 45 min. Evaporation of EtSCl at room temperature and 11 mmHg gave a colourless liquid. Yield: 2.44 g (89%).

¹H NMR (60 MHz, CDCl₃): δ2.20 (s, 3H, CH₃C=O), 5.76 (s, 2H, OCH₂O).

x) Hexamethylene di(chloromethyl carbonate)

Chloromethyl chloroformate (19.12 g, 148.5 mmol) was added to an ice-cooled (0° C.) solution of 1,6-hexanediol (5.90 g, 50 mmol) in CH₂Cl₂ (200 ml). Pyridine (8.70 g, 110 mmol) was then added and the reaction mixture was left with stirring for 15 min. at 0° C. and 5 hours at room temperature. The reaction mixture was washed with HCl (1M, 100 ml), NaHCO₃ (aq, saturated, 100 ml), water (100 ml) and dried (MgSO₄). The solvent was evaporated and gave 13.25 g (95%) of the title product.

¹H NMR (60 MHz, CDCl₃): δ1.20–2.00 (m, 8H, (CH₂)₄), 4.22 (t, 4H, 2 X (CH₂O), 5.73 (s, 4H, 2 X OCH₂Cl).

y) Methacryloyloxymethyl acetate

Potassium tert. butoxide (5.0 g, 0.045 mol) was added to a solution of methacrylic acid (3.87 g, 0.045 mol) in DMF (150 ml). Chloromethyl acetate³ (4.86 g, 0.045 mol) was added to the resulting suspension. 18-crown-6 (0.9 g, 3.45 mmol) was then added and the reaction mixture was left with stirring at room temperature for 4 days. The reaction mixture was filtered and the solvent was removed under reduced pressure. The residue was dissolved in chloroform (100 ml) and washed with saturated aqueous sodium hydrogen carbonate (50 ml) and water (50 ml). The organic phase was dried (MgSO₄) and the solvent removed under reduced pressure. Flash chromatography gave 5.19 g (75%) of the title product.

¹H NMR (60 MHz, CDCl₃): δ2.00 (s, 3H, CH₃C=), 2.18 (s, 3H, CH₃C=O), 5.70 (m, 1H, CH₂=), 5.85 (s, 2H, —OCH₂O—), 6.25 (m, 1H, CH₂=)

z) Butyl acryloyloxymethyl carbonate

Potassium tert. butoxide (5.84 g, 0.052 mol ) was added to a solution of acrylic acid (4.47 g, 0.045 mol) in DMF (220 ml). Butyl chloromethyl carbonate (Example 1i, 6.5 g, 0.052 mol) in DMF (150 ml) was added to the resulting suspension. 18-crown-6 (0.6 g) was then added and the reaction mixture was left with stirring at room temperature for 2 days. The reaction mixture was filtered and the solvent was removed under reduced pressure. The residue was dissolved in chloroform (100 ml) and washed with saturated aqueous sodium hydrogen carbonate (50 ml) and water (50 ml). The organic phase was dried (MgSO₄) and the solvent removed under reduced pressure. Flash chromatography gave 4.57 g of the title product.

¹H NMR (60 MHz, CDCl₃): δ0.80 (t, 3H, CH₃CH₂), 1.28 (m, 2H, CH₂), 1.60 (m, 2H, CH₂), 4.15 (t, CH₂O), 5.78 (s, 2H, OCH₂O), 5.88 (dd, 1H, CH₂=), 6.1 (dd, 1H, CH₂=), 6.45 (dd, 1H, CH₂=CH—).

aa) 3,6,9-Trioxaundecanedioic acid dichloride 3,6,9-Trioxaundecanedioic acid (2,0 mmol) was refluxed in thionyl chloride (1 ml) for 6 hours before excess thionyl chloride was evaporated under reduced pressure. The crude product was used in the subsequent step without purification.

¹H NMR (CDCl₃): δ3.64–3.68 (m, 4H), 3.76–3.82 (m, 4H), 4.49–4.51 (m, 4H).

¹³C NMR (CDCl₃): δ70.70, 71.29, 76.65, 172.03.

ab) 1-(7-Benzyloxycarbonylheptanoyloxy)ethyl decyl carbonate (i) 1-Benzylnonanedioic acid A solution of nonanedioic acid (25.0 g, 0.13 mol) in benzene (550 ml) was added to p-toluenesulphonic acid (0.71 g, 3.72 mmol) and heated to 80° C. Benzyl alcohol (14.3 g, 0.13 mol) in benzene (50 ml) was added dropwise. The reaction mixture was refluxed overnight. Water was removed from the reaction mixture and collected by a Dean Stark trap. After 24 hours no benzyl alcohol was detected by TLC. The reaction mixture was cooled to room temperature and then in an ice bath. The precipitated unreacted nonanedioic acid was removed by filtration. The filtrate was concentrated to dryness. The residue was purified by column chromatography using dichloromethane/methanol (10:1) as eluent. Yield: 28%.

¹H NMR (300 MHz, CDCl₃): δ7.35–7.31 (m, Ar); 5.10 (s, ArCH₂); 2.33 (t, CH₂CO); 1.62 (m, CH₂CH₂CO); 1.29 [m, (CH₂)₃].

(ii) Cesium 1-benzylnonanedioate

1-Benzylnonanedioic acid (Example 1ac(i), 6.3 g, 21.6 mmol) was suspended in distilled water (100 ml) and heated to 50° C. Cesium carbonate (3.5 g, 10.8 mmol) in water (20 ml) was added dropwise to pH 7. Water was removed by lyophilization for 2 days. Yield: 95%.

(iii) 1-Chloroethyl decyl carbonate

To a stirred solution of decanol (6.0 g, 7.23 mmol) in dichloromethane (150 ml) was added dry pyridine (3.66 ml, 45.6 mmol). The solution was cooled in an ice bath. To this was added 1-chloroethyl chloroformate (6.5 g, 45.6 mmol) dropwise. The reaction mixture was allowed to proceed overnight, diluted with dichloromethane and washed with 0.5N HCl solution, twice with a saturated sodium bicarbonate solution and finally with distilled water. The solvent was dried over magnesium sulphate, filtered through silica and concentrated to dryness. Yield: 93%.

¹H NMR (300 MHz, CDCl₃): δ6.43 (q, CHCl); 4.19 (t, CH₂O); 1.83 (d, CH₃CH); 1.69 (CH₂CH₂O); 1.40–1.22 [m, (CH₂)₈]; 0.88 (t, CH₃CH₂).

(iv) 1-(7-Benzyloxycarbonylheptanoyloxy)ethyl decyl carbonate

Cesium 1-benzylnonanedioate (Example 1ac(ii), 5.0 g, 12.2 mmol) was dissolved in DMF (150 ml). To this was added 1-chloroethyl decyl carbonate (Example 1ac(iii), 3.25 g, 12.2 mmol), followed by potassium iodide (125 mg, 0.75 mmol). The reaction was allowed to proceed at 50° C. for 3 days. The solvent was removed under reduced pressure. The residue was suspended in dichloromethane and washed 3 times with a saturated sodium bicarbonate solution and finally twice with water. After drying over magnesium sulphate the solution was evaporated to dryness. The product was purified by column chromatography using petroleum ether/ethyl acetate (12:1) as eluent. Yield: 65%.

¹H NMR (300 MHz, CDCl₃): δ7.35–7.31 (m, Ar); 6.78 (q, OCHCH₃O); 5.10 (s, ARCH₂); 4.19 (t, CH₂O); 2.33 (t, CH₂CO).

(v) 1-(7-Carboxyheptanoyloxy) ethyl decyl carbonate

To a solution of 1-(7-benzyloxycarbonylheptanoyloxy) ethyl decyl carbonate (Example 1ac(iv), 4.0 g, 7.9 mmol) in acetic acid (15 ml) was added a catalytic amount of palladium on charcoal (150 mg). The mixture was hydrogenated with H₂ at ambient temperature for 5 hours. Acetic acid was removed under reduced pressure. The residue was purified by column chromatography using n-heptane/ethyl acetate (4:1) as eluent. Yield: 52%.

¹H NMR (300 MHz, CDCl₃): δ6.76 (q, OCHCH₃₀); 4.19 (t, CH₂O); 2.32 (t, CH₂CO).

¹³C NMR (300 MHz, DMSO-d₆) δ174.67 (COOH); 171.30 (CH₂COO); 152.68 (OCOO); 91.09 (OCHCH₃).

ac) Nonylcarbonyloxymethyl chloroformate (i) Potassium decanoate

A solution of KOH (2.6 g, 46.4 mmol) in water (50 ml) was added dropwise to a suspension of decanoic acid (8.0 g, 46.4 mmol) in water (300 ml) at 60 °C. until pH 7. Water was removed by lyophilization. Yield: 9.28 g (95%).

(ii) O-Nonylcarbonyloxymethyl S-ethyl carbonothioate

O-Chloromethyl S-ethyl carbonothioate[1] (4.79 g, 0.031 mol) in DMA (20 ml) was added to a suspension of potassium decanoate (Example 1ad(i), 6.5 g, 0.031 mol) in DMA (500 ml). 18-Crown-6 (0.25 g, 0.93 mmol) was then added, and the reaction mixture was left with stirring at ambient temperature for 22 hours. The reaction mixture was filtered and the solvent was removed under reduced pressure. The residue was purified by flash chromatography (silica gel, hexane/ethyl acetate (30:1)). Yield: 5.96 g (67%).

$^1$H NMR (300 MHz, CDCl$_3$): δ0.88 (t, 3H, CH$_3$(CH$_2$)$_8$, 1.27 (m, 12H, (CH$_2$)$_6$), 1.33 (t, 3H, CH$_3$CH$_2$S), 1.63 (m, 2H, CH$_2$CH$_2$=O), 2.37 (t, 2H, CH$_2$C=O), 2.89 (q, 2H, CH$_2$S), 5.81 (s, 2H, OCH$_2$O).

$^{13}$C NMR (300 MHZ, CDCl$_3$): δ14.1, 14.8, 22.7, 24.6, 25.4, 29.0, 29.2, 29.3, 29.4, 31.9, 33.9, 80.2 (OCH$_2$O), 170.7 (C=O), 172.2 (C=O).

(iii) Nonylcarbonyloxymethyl chloroformate

SO$_2$Cl$_2$ (1.17 g, 8.65 mmol) was added to O-nonylcarbonyloxymethyl S-ethyl carbonothioate (Example 1ad(ii), 2.10 g, 7.22 mmol) in CH$_2$Cl$_2$ (5 ml) at 0° C. with stirring during 15 min. followed by stirring at ambient temperature for 17 hours. Evaporation of EtSCl at 30° C. and 20 mmHg gave a yellow liquid. Yield: 1.62 g (85%).

$^1$H NMR (300 MHZ, CDCl$_3$): δ0.88 (t, 3H, CH$_3$), 1.27 (m, 12H, (CH$_2$)$_6$), 1.66 (m, 2H, CH$_2$CH$_2$C=O), 2.41 (t, 2H, CH$_2$C=O), 5.82 (s, 2H, OCH$_2$O).

$^{13}$C NMR (300 MHz, CDCl$_3$): δ14.1, 22.7, 24.5, 29.0, 29.19, 29.24, 29.4, 31.9, 33.8, 83.3 (OCH$_2$O), 150.1 (ClC=O), 171.7 (C=O).

ad) 1-Acetoxy-1-phenylmethyl vinyl carbonate (i) 1-Chloro-1-phenylmethyl vinyl carbonate Vinyl chloroformate (3.0 g, 0.028 mol) and benzaldehyde (4.14 g, 0.039 mol) were dissolved in 1,2-dichloroethane (30 ml) and pyridine (0.1 g, 1.28 mol) was added dropwise to the stirred solution. The solution was stirred for 1 day at 80° C., washed with water (25 ml), and the aqueous phase was back extracted with methylene chloride (25 ml). The combined organic phases were dried (MgSO$_4$) and concentrated to give 3.0 g (50%) of the title product.

$^1$H NMR (60 MHz, CDCl$_3$): δ4.55 (dd, 1H, CH$_2$=), 4.95 (dd, 1H, CH$_2$=), 7.05 (dd, 1H, CH$_2$=CH—), 7.25 (s, 1H, CH—Ph), 7.40 (m, 5H, Ph).

(ii) 1-Acetoxy-1-phenylmethyl vinyl carbonate

Silver acetate (2.0 g, 0.012 mol) was added to a solution of 1-chloro-1-phenylmethyl vinyl carbonate (2.50 g, 0.012 mol) in DMF (60 ml). The reaction mixture was left with stirring at room temperature for 12 hours. The reaction mixture was filtered and the solvent was removed under reduced pressure. The residue was purified by flash chromatography (silicagel, methylene chloride) to give 0.56 (20%) of the title product.

$^1$H NMR (60 MHz, CDCl$_3$): δ2.24 (s, 3H, CH$_3$C=O), 4.60 (dd, 1H, CH$_2$=), 4.95 (dd, 1H, CH$_2$=), 7.00 (dd, 1H, CH=), 7.50 (m, 5H, Ph), 8.00 (s, 1H, —CH—Ph).

ae) Benzoyloxymethyl chloroformate (i) O-Benzoyloxymethyl S-ethyl carbonothioate Q-Chloromethyl S-ethyl carbonothioate[1] (5.73 g, 0.037 mol) in DMF (20 ml) was added to a solution of potassium benzoate (5.94 g, 0.037 mol), and 18-crown-6 (0.485 g, 1.85 mmol) in DMF (130 ml) was then added and the reaction mixture was left with stirring at room temperature for 24 hours. The solvent was removed under reduced pressure. The residue was dissolved in chloroform (150 ml) and washed with water (5×20 ml) and dried (MgSO$_4$). The solvent was removed under reduced pressure, purified by flash chromatography (silicagel, chloroform) to give 7.16 g (81%) of the title product.

$^1$H NMR (60 MHz, CDCl$_3$): δ1.3 (t, 3H, CH$_3$), 2.9 (q, 2H, CH$_2$CH$_3$), 6.1 (s, 2H, OCH$_2$O), 7.3–7.7 (m, 3H, Ph), 8.0–8.2 (m, 2H, Ph).

(ii) Benzoyloxymethyl chloroformate

SO$_2$Cl$_2$ (4.03 g, 0.030 mol) was added to O-benzoyloxymethyl-S-ethyl carbonothioate (7.16 g, 0.030 mol) at 0°–5° C. with stirring during 15 min. followed by stirring at room temperature for 2 hours. Evaporation of EtSCl at room temperature and 11 mmHg gave a yellow liquid. Yield: 5.30 g (83%).

$^1$H NMR (60 MHz, CDCl$_3$): δ6.1 (s, 2H, OCH$_2$O), 7.3–7.7 (m, 3H, Ph), 8.0–8.2 (m, 2H, Ph).

af) Ethylidene bis(16-hydroxyhexadecanoate)

DBU (2.74g, 0.018 mol) was added to 16-hydroxyhexadecanoic acid (4.90 g, 0.018 mol) in DMF (150ml). After 5 minutes with stirring, ethylidene iodide (2.54 g, 0.009 mol) was added and the mixture was left with stirring at 40° C. for 3 days. The reaction mixture was cooled to 20° C. and when precipitation was complete (2 hours) the precipitated monomer was isolated by filtration. The monomer was treated with activated carbon and recrystallised twice from dichloromethane to give 1.03 g (20%) of the title product. Differential scanning calorimetry (DSC) indicated that onset melting temperature was 88.93° C. $^1$H NMR(200 MHz, CDCl$_3$): δ1.25(s, 44H, CH$_2$), 1.45(d, 3H, CH$_3$CH), 1.56 (m, 8H, CH$_2$), 2.30 (t, 4H, CH$_2$CO), 3.63 (t, 4H,2 X CH$_2$O), 6.86 (q, 1H, CHCH$_3$). $^{13}$C NMR(50 MHz, CDCl$_3$): δ20.86, 25.91, 26.98, 30.22, 30.44, 30.67, 30.84, 34.00, 35.30, 64.00, 89.00, 171.77 (C=O).

ag) Ethylidene bis[16-(5-chlorocarbonylpentanoyloxy) hexadecanoate]

In a three-necked round bottomed flask equipped with a reflux condenser, a glass gas inlet tube and a pressure equalizing dropping funnel was placed freshly distilled adipoyl chloride (2.60 ml, 17.50 mmol) dissolved in absolute chloroform (15 ml). The temperature was raised to ca. 50° C. and under a gentle stream of nitrogen through the solution, a solution of ethylidene bis(16-hydroxyhexadecanoate) (1.0g, 1.75 mmol) in absolute chloroform (30 ml) was added dropwise and left at this temperature a further 3 hours after addition. The mixture was then cooled to room temperature and quickly transferred into a 50 ml round bottomed flask equipped for distillation under reduced pressure. Chloroform was first distilled off at normal pressure, then oil-pump vacuum was established and excess adipoyl chloride distilled off at ca. 75° C., 5 mbar pressure, leaving the residual title compound (1.56 g).

ah) 16-Hexadecanoyloxyhexadecanoic acid

16-Hydroxyhexadecanoic acid (5.43 g, 19.9 mmol) was dissolved in tetrahydrofuran (190 ml) and pyridine (2.36 g, 29.9 mmol) was added. palmitoyl chloride (5.48 g, 19.9 mmol) was dissolved in tetrahydrofuran (10 ml) and added dropwise at room temperature. After stirring at room temperature for 16 hours, the mixture was filtered and the filtrate evaporated under reduced pressure. The residue was dissolved in chloroform, washed with water (3×50 ml), and the organc phase was dried (MgSO$_4$). After evaporating under reduced pressure, the residue was purified on a silica column, eluted with chloroform with increasing methanol concentration (from 1% to 2% methanol in chloroform) to give 8.41 g (83%) of the title compound. $^1$H NMR (300 MHz, CDCl$_3$): δ0.85 (t, 3H, CH$_3$), 1.20–1.35 (s, 46H, —CH$_2$—), 1.55–1.70 (m, 6H, —CH$_2$—), 2.25 (t, 2H, —CH$_2$—C(O)—O), 2.45 (t, 2H, —CH$_2$—COOH), 4.05 (t, 2H, —O—CH$_2$). $^{13}$C NMR (75 MHz, CDCl$_3$): δ14.01, 22.57, 24.10, 24.91, 25.82, 28.53, 28.75, 28.94, 29.08, 29.15, 29.25, 29.36, 29.54, 31.81, 34.29, 35.16, 64.27, 76.48, 76.90, 77.10, 77.32, 169.50, 173.91.

ai) 16-Hexadecanoyloxyhexadecanoyl chloride

16-Hexadecanoyloxyhexadecanoic acid (7.73 g, 15.13 mmol) prepared as in (ah) above was dissolved in tetrahydrofuran (140 ml) and oxalyl chloride (4.80 g, 37.83 mmol) was added dropwise. The mixture was stirred at room temperature for 3 days and then the solvent and unreacted oxalyl chloride were evaporated under reduced pressure to give 8.0 g (100%) of the title compound.

aj) 1-[16-(16-Hexadecanoyloxyhexadecanoyloxy) hexadecanoyloxy]ethyl 16-hydroxyhexadecanoate Ethylidene bis (16-hydroxyhexadecanoate) (4.38 g, 7.67 mmol) was dissolved in THF (80 ml) and pyridine (0.61 g, 7.71 mmol) was added. 16-hexadecanoyloxyhexadecanoyl chloride (4.18 g, 7.90 mmol) was dissolved in THF (20 ml) and added dropwise. After 3 days at room temperature the mixture was filtered and the filtrate was left at –20° C. for 2 hours. The precipitated product was filtered and purified by flash chromatography (silicagel, chloroform) to give 2.4 g (29%) of the title compound. $^1$H NMR (300 MHz, CDCl$_3$): δ0.85 (t, 3H, CH$_3$), 1.2–1.4 (s, 90H, 1.45 (d, —O—CH (CH$_3$)—O—), 1.5–1.7 (m, 14H, —CH$_2$—), 2.25 (m, 8H, —CH$_2$—C(O)—O—), 3.60 (t, 2H, —CH$_2$—OH), 4.05 (t, 4H, —C(O)—O—CH$_2$—), 6.85 (q, 1H, —O—CH(CH$_3$)—O—). $^{13}$C NMR (75 MHz, CDCl$_3$): δ13.7, 19.1, 22.2, 24.2, 24.6, 25.2, 25.5, 28.2, 28.5, 28.7, 28.8, 29.0, 29.2, 31.5, 32.3, 33.7, 34.0, 62.5, 64.0, 88.0, 171.5, 173.5.

ak) Preparation of Methoxy-endcapped PEGS

Preparation of a Tyical Polymer (MeO-PEG 2900)

An initiator solution was prepared by careful addition of potassium metal (0.400 g, 10.23 mmol) to methanol (1.300 g, 40.57 mmol) in an inert atmosphere. This initiator solution (0.220 g, 1.32 mmol potassium methoxide) was injected into an ampoule containing ethylene oxide (10.000 g, 227.00 mmol). The sealed ampoule was allowed to stand at room temperature overnight. The temperature was then raised to 60° C. and reaction allowed for 72 hours. After removal of unreacted monomer, the contents of the ampoule were dissolved in dichloromethane and the solution neutralised with dilute aqueous hydrochloric acid. The polymer solution was washed three times with distilled water, rotary evaporated and then vacuum dried. Assignments for MeO-PEG polymers. $^1$H-NMR: δ2.7 (OH), 3.2 (OCH$_3$), 3.5 (—CH$_2$— main chain), 3.4 (—CH$_2$OCH$_3$). $^{13}$NMR: δ58.5 (—OCH$_3$), 61.2 (—CH$_2$OH), 70.5 (—CH$_2$—main chain), 71.3 (—CH$_2$OCH$_3$), 72.2 (—CH$_2$CH$_2$OH). The GPC was recorded in THF and the molecular weight calibration was via PEG standards. GPC data for a typical sample: Mp: 2679, Mn: 2012, Mw: 2283. Polydispersity: 1.135.

al) General procedure for methoxy PEG chloroformate

PEG 2000 monomethyl ether (6.00g, 3.00 mmol) was dissolved in toluene (50 ml) and dried by refluxing in a Dean Stark apparatus. Pyridine (0.24 g, 3.00 mmol) was added at room temperature. Trichloromethyl chloroformate ("diphosgene") (0.60 g, 3.00 mmol) was dissolved in toluene (10 ml) and added dropwise. The mixture was stirred at room temperature for 12 hours and filtered. The solvent was evaporated under reduced pressure to give the title compound in quantitative yield.

EXAMPLE 2

Preparation of polymers and emulsifiers a) Emulsion copolymerization of methylene dimethacrylate and styrene 50ml of a 1% wt/vol solution of sodium dodecyl sulphate in water was pre-heated to 60° C. under a nitrogen atmosphere. 0.20 g (1.09 mmol) of methylene dimethacrylate from Example 1a above and 9.80 g (0.094 mol) styrene monomer were added under vigorous stirring. The polymerisation was initiated with a metabisulphite/persulphate redox system comprising 1.6 mg (7.2 mmol) potassium metabisulphite and 0.08 mg (0.3 mmol) potassium persulphate. The polymerisation was permitted to proceed for 8 hours before cooling to room temperature. The resultant emulsion had a solids content of 11.2% which corresponded to a degree of conversion of 68%. The recovered polymer was not soluble in THF, a good solvent for polystyrene, indicating that the polymer was crosslinked.

b) Polymer from methylene bis(16-hydroxyhexadecanoate) and adipoyl chloride

A solution of adipoyl chloride (0.657 g, 3.59 mmol) in xylene/trichloroethylene (80:20 by weight, 5 ml) was added dropwise to a solution of methylene bis(16-hydroxyhexadecanoate) (2.000 g, 3.59 mmol) from Example 1b (iv) above in xylene/trichloroethylene (80:20 by volume, 160 ml) at 60° C. After 44 hours at 60° C. under reduced pressure, the reaction mixture was cooled to 20° C., and the solvent evaporated under reduced pressure to give 0.227 g of white solid.

IR (neat), cm$^{-1}$: 2915 (s), 1759, 1732 (s), 1466, 1417 (w), 1380, 1263, 1175 (w), 1105 (w), 991 (w), 798 (w), 726.

$^1$H NMR (300 MHz, CDCl$_3$): δ1.58 (m, 44H, CH$_2$), 1.63 (m, 12H, CH$_2$), 2.29 (m, 8H, CH$_2$CO), 4.04 (m, 4H, 2 X CH$_2$O), 5.73 (m, 2H, —OCH$_2$O—).

Size Exclusion Chromatography (SEC): Mw=11100, Mn=6500, Mp=14100, Mw/Mn=1.7 c) Polymer from methylene bis(12-hydroxydodecanoate) and adipoyl chloride

A solution of adipoyl chloride (1.22 g, 6.7 mmol) in xylene/trichloroethylene (80:20 by weight, 5 ml) was added dropwise to a solution of methylene bis(12-hydroxydodecanoate) (3.00 9, 6.7 mmol) from Example 1c above in xylene/trichloroethylene (80:20 by volume, 100 ml) at 60° C. After 4 days at 60° C. under reduced pressure, the reaction mixture was cooled to 20° C., and the solvent evaporated under reduced pressure to give a yellow solid compound. The compound was purified by flash chromatography (silica/step gradient from chloroform to ethyl acetate).

Size Exclusion Chromatography (SEC): Mw=18276, Mn=12840, Mw/Mn=1.423 d) Polymer from methylene bis(10-hydroxydecanoate) and succinyl chloride

Succinyl chloride (0.200 g, 1.29 mmol) was added to a solution of methylene bis(10-hydroxydecanoate) (0.500 g, 1.29 mmol) from Example 1d above in toluene (60 ml) at 70° C. After 100 hours at 70° C. under reduced pressure, the reaction mixture was cooled to 20° C. and solvent evaporated under reduced pressure to give 0.436 g of a yellow solid.

IR (neat): 2933 (s), 1787, 1738 (s), 1650, 1465 (w), 1413 (w), 1357 (w), 1262 (w), 1164, 1099 (w), 1049 (w), 988, 906, 802 cm$^{-1}$.

$^1$H NMR (300 MHz, CDCl$_3$): δ1.25 (m, 20H, CH$_2$), 1.57 (m, 8H, CH$_2$), 2.32 (m, 4H, CH$_2$CO), 2.61 (m, 4H, CH$_2$CO), 4.04 (m, 4H, 2 X CH$_2$O), 5.70 (s, 2H, —OCH$_2$O—).

Size Exclusion Chromatography (SEC): Mw=1870, Mn=1580, Mp=1310, Mw/Mn=1.18 e) Oligomer from methylene bis(10-hydroxydecanoate) and succinic acid,

Succinic acid (0.152 t, 1.29 mmol) was added to a solution of methylene bis(10-hydroxydecanoate) (0.500 g, 1.29 mmol) from Example 1d above and p-toluene sulphonic acid (0.007 g, 0.004 mmol) in toluene (12 ml) at 130° C. After 84 hours at 140° C. with continuous removal of formed water by distillation, the reaction mixture was cooled to 20° C. Solvent was evaporated under reduced pressure giving 0.425 g of a yellow solid.

IR (neat): 2933 (s), 1739 (s), 1650, 1467 (w), 1415, 1360 (w), 1261, 1168, 1100, 995, 803, 724 cm$^{-1}$.

$^1$H NMR (300 MHz, CDCl$_3$): δ1.27 (m, 20H, CH$_2$), 1.59 (m, 8H, CH$_2$), 2.33 (m, 4H, CH$_2$CO), 2.64 (m, 4H, CH$_2$CO), 4.05 (m, 4H, 2 X CH$_2$O), 5.72 (s, 2H, —OCH$_2$O—), 10.00 (bs, 2H).

Size Exclusion Chromatography (SEC): Indicated no polymer formation (only oligomers)

f) Polymer from methylene bis(10-hydroxydecanoate) and adipoyl chloride,

A solution of adipoyl chloride (0.943 g, 5.15 mmol) in xylene/trichloroethylene (80:20 by weight, 7 ml) was added dropwise to a solution of methylene bis(10-hydroxydecanoate) (2.000 g, 5.15 mmol) from Example 1d above in xylene/trichloroethylene (80:20 by volume, 120 ml) at 60° C. After 48 hours at 60° C. under reduced pressure, the reaction mixture was cooled to 20° C., and the solvent evaporated under reduced pressure to give a white solid. Flash chromatography (silica, ethyl acetate) gave 0.44 g of a polymer fraction.

$^1$1H NMR (300 MHz, CDCl$_3$): δ1.32 (m, 20H, CH$_2$), 1.57 (m, 12H, CH$_2$), 2.34 (m, 8H, CH$_2$CO), 4.03 (m, 4H, 2 X CH$_2$O), 5.71 (s, 2H, —OCH$_2$O—).

Size Exclusion Chromatography (SEC): Mw=20964, Mn=12382, Mp=22843, Mw/Mn=1.693 g) Polymer from bis(chlorocarbonyloxymethyl) terephthalate and 1,6-diaminohexane 1,6-diaminohexane (0.23 9, 0.002 mol) and triethylamine (0.40 g, 0.004 mol) in THF (5 ml) were added to a solution of bis(chlorocarbonyloxymethyl) terephthalate (0.70 g, 0.002 mol) from Example 1e(ii) above in THF (20 ml). The reaction mixture was left with stirring for 6 days at room temperature. The reaction mixture was filtered and the solvent was removed under reduced pressure and gave a polymer which was insoluble in chloroform.

$^1$H NMR (60 MHz, CDCl$_3$): δ1.20 (m, 8H, 4 x CH$_2$), 2.85–3.20 (m, 6H, 2 x NH and 2 x CH$_2$N), 5.85 (s, 2H, OCH$_2$O), 8.00 (s, 4H, Ar).

h) Polymer from methylene bis(4-hydroxymethylbenzoate) and adipoyl chloride

A solution of adipoyl chloride (1.26 g, 6.89 mmol) in 1,1,2,2-tetrachloroethane/trichloroethytene (80:20 by weight, 5 ml) was added dropwise to a solution of methylene bis(4-hydroxymethyl benzoate) (2.18 g, 6.89 mmol) from Example 1f above in 1,1,2,2-tetrachloroethane/trichloroethylene (80:20 by weight, 90 ml) at 60° C. After 4 days at 60° C. under reduced pressure, the reaction mixture was cooled to 20° C., and the solvent evaporated under reduced pressure to give 2.82 g of a brown viscous oil. Precipitation in methanol gave 0.80 g of a yellow compound. Size Exclusion Chromatography (SEC): Mw=3793, Mn=2715, Mp=2845, Mw/Mn=1.724.

$^1$H NMR (200 MHz, CD$_3$COCD$_3$): δ1.65 (s br, 4H, CH$_2$), 2.40 (s br, 4H, CH$_2$CO), 5.18 (s, 4H, O—CH$_2$—Ph), 6.25 (s, 2H, OCH$_2$O), 7.4–7.6 (m, 4H, Ph), 7.9–8.1 (m, 4H, Ph).

i)-m) General procedure for polymerization of methacryloyloxymethyl carbonates

A solution of methacryloyloxymethyl carbonate (1.0 g) from Example 11-p above in DMF (8.0 g) was heated to 60° C. and AIBN (0.005 g, 0.03 mmol) was added. After 24 hours the reaction mixture was cooled and the polymer solution added dropwise to a stirred excess of methanol (non-solvent). The polymer was filtered and washed with methanol and water, and dried under reduced pressure.

i) Polymer from methyl methacryloyloxymethyl carbonate

IR (KBr): 1763 (C═O, str.) cm$^{-1}$ $^1$H NMR (300 MHz, CDCl$_3$): δ1.00 (m, 2H, CH$_2$), 1.90 (m, 3H), 3.85 (s, 3H, CH$_{3O}$), 5.70 (s, 2H, OCH$_2$O).

$^{13}$C NMR (75 MHz, CDCl$_3$): δ46.35 (C—CH$_3$), 56.55 (CH$_3$O), 83.59 (—OCH$_2$O—), 154.41 (C═O), 175.50 (C═O).

Differential scanning calorimetry (DSC) indicated that Tg=59.8° C. and onset decomposition temperature was 242.2° C. Thermal mechanical analysis indicated a glass transition temperature of 59.9° C.

Size Exclusion Chromatography (SEC): Mw=100000, Mn=59000, Mw/Mn=1.7.

j) Polymer from ethyl methacryloyloxymethyl carbonate
IR (KBr): 1763 (C═O, str.) cm$^{-1}$ $^1$H NMR (300 MHz, CDCl$_3$): δ1.00 (m, 2H, CH$_2$), 1.32 (t, 3H, CH$_3$), 1.90 (m, 3H, CH$_3$), 4.25 (m, 2H, CH$_2$O), 5.70 (s, 2H, OCH$_2$O).

$^{13}$C NMR (75 MHz, CDCl$_3$): δ15.77 (—OCH$_2$O—), 46.35 (C—CH$_3$), 65.90 (CH$_2$O), 83.50 (—OCH$_2$O—), 153.69 (C═O), 175.80 (C═O).

Differential scanning calorimetry (DSC) indicated that Tg=35.9° C. and onset decomposition temperature was 260.9° C. Thermal mechanical analysis indicated a glass transition temperature of 31.2° C.

Size Exclusion Chromatography (SEC): Mw=34000, Mn=20000, Mw/Mn=1.7.

k) Polymer from butyl methacryloyloxymethyl carbonate
IR (KBr): 1763 (C═O) cm$^{-1}$ $^1$H NMR (300 MHz, CDCl$_3$): δ0.90 (t, 3H, CH$_3$), 1.00 (m, 2H, CH$_2$), 1.39 (m, 2H, CH$_2$), 1.70 (m, 2H, CH$_2$), 1.90 (m, 3H, CH$_3$), 4.20 (t, 2H, CH$_2$O), 5.68 (s, 2H, OCH$_2$O).

$^{13}$C NMR (75 MHz, CDCl$_3$): δ13.54 (CH$_3$CH$_2$), 18.73 (CH$_2$), 30.39 (CH$_2$), 46.26 (C—CH$_3$), 69.72 (CH$_2$O), 83.67 (—OCH$_2$O—153.86 (C═O), 175.80 (C═O).

Differential scanning calorimetry (DSC) indicated that onset decomposition temperature was 239.9° C. (Tg was not observed). Thermal mechanical analysis indicated a glass transition temperature of 24.7° C. Size Exclusion Chromatography (SEC): Mw=60000, Mn=29000, Mw/Mn=2.1.

l) Polymer from decyl methacryloyloxymethyl carbonate
IR(KBr): 1763 (C═O, str.) cm$^{-1}$ $^1$H NMR (300 MHz, CDCl$_3$): δ0.90 (t, 3H, CH$_3$), 0.90 (m, 3H, CH$_2$), 1.30 (m, 14H, CH$_2$), 1.70 (m, 2H, CH$_2$), 1.90 (m, 2H), 4.19 (t, 2H, CH$_2$O), 5.66 (s, 2H, OCH$_2$O).

¹³C NMR (75 MHz, CDCl₃): δ13.78 (CH₃), 22.34–31.57 (CH₂), 46.26 (C—CH₃), 68.70 (CH₂O), 83.67 (—OCH₂O—), 153.55 (C=O), 175.80 (C=O).

Differential scanning calorimetry (DSC) indicated onset decomposition temperature was 232.9° C. (Tg was not observed). Thermal mechanical analysis indicated a glass transition temperature of −3.3° C.

Size Exclusion Chromatography (SEC): Mw=160000, Mn=90000, Mw/Mn=1.7.

m) Polymer from benzyl methacryloyloxymethyl carbonate

IR (KBr): 3077 (Ph), 1763 (C=O, str.) cm⁻¹

¹H NMR (300 MHz, CDCl₃): δ0.95 (m, 3H, CH₃), 1.90 (m, 2H), 5.25 (s, 2H, CH₂O), 5.75 (s, 2H, OCH₂O), 6.70 (s, 5H, Ph).

¹³C NMR (75 MHz, CDCl₃): δ46.26 (—C—CH₃), 68.03 (—OCH₂Ph), 82.02 (—OCH₂O—), 129.45 (Ph), 153.67 (C=O), 175.80 (C=O).

Differential scanning calorimetry (DSC) indicated that Tg=31.6° C. and onset decomposition temperature was 197.1° C. Thermal mechanical analysis indicated a glass transition temperature of 32.8° C.

Size Exclusion Chromatography (SEC): Mw=92000, Mn=44000, Mw/Mn=2.1.

n) Free radical solution polymerisation of benzyl methacryloyloxymethyl carbonate giving low molecular weight polymer A solution of benzyl methacryloyloxymethyl carbonate (0.5 g, 2.0 mmol) from Example 1p above in DMF (7.5 g) was heated to 60° C. and allyl mercaptan (0.0015 g, 0.02 mmol) together with AIBN (0.0025 g, 0.015 mmol) was added. After 24 hours the reaction mixture was cooled and the polymer solution added dropwise to a stirred excess of methanol (non-solvent). The polymer was filtered and washed with methanol and water and dried under reduced pressure.

Size Exclusion Chromatography (SEC): Mw=22000, Mn=14000.

o) Free radical polymerisation of methyl 1-methacryloyloxyethyl carbonate

AIBN (0.005 g, 0.03 mmol) was added to a solution of methyl 1-methacryloyloxyethyl carbonate (1.0 g, 5.0 mmol) from Example 1u(ii) above in dry THF (8 g) at 60° C. under a dry nitrogen atmosphere. After 24 hours the reaction mixture was cooled to 20° C., and the solvent removed under reduced pressure. The resulting polymer was dissolved in CH₂Cl₂ and reprecipitated in methanol. Methanol was separated from the polymer by filtration, resulting in a white powder.

¹H NMR (200 MHz, CDCl₃): δ0.90 (m, 3H, CH₃), 1.45 (s, 3H, CH₃CH), 1.87 (m, 2H, CH₂), 3.80 (s, 3H, CH₃O), 6.65 (bs, 1H, CHCH₃).

Size Exclusion Chromatography (SEC): Mw=16033, Mn=6641, Mp=16192, Mw/Mn=2.41. Differential scanning calorimetry (DSC) indicated that Tg=57.65 ° C.

p) Free radical polymerisation of ethyl 1-methacryloyloxyethyl carbonate.

AIBN (0.033 g, 0.02 mmol) was added to a solution of ethyl 1-methacryloyloxyethyl carbonate (0.504 g, 2.49 mmol) from Example 1q(ii) above in dry THF (8 ml) at 50° C. under a dry nitrogen atmosphere. After 7 hours the reaction mixture was cooled to 20° C., and polymer precipitated in methanol (50 ml) and the solution filtered. The resulting polymer was dissolved in THF, reprecipitated in methanol (70 ml) and filtered, resulting in 0.138 g of a white powder.

¹H NMR (300 MHz, CDCl₃): δ0.90 (m, 3H, CH₃), 1.25 (s, 3H, CH₃), 1.45 (s, 3H, CH₃), 1.87 (m, 2H, CH₂), 4.15 (bs, 2H, CH₂O), 6.62 (bs, 1H, —CHCH₃).

Size Exclusion Chromatography (SEC): Mw=26500, Mn=18600, Mp=22000, Mw/Mn=1.43 q) Polymer from ethyl methacryloyloxymethyl carbonate emulsion polymerisation

A solution of sodium dodecyl sulphate (0.056 g, 0.19 mmol) in water (20.5 ml) was heated to 60° C. under nitrogen atmosphere, before ethyl methacryloyloxymethyl carbonate (5.266 g, 28.00 mmol) from Example 1m above was added. The polymerisation was initiated with a potassium metabisulphite (53.4 mg, 0.24mmol)/potassium persulphate (4.38 mg, 0.02 mmol) redox system. After 16 hours at 60° C., potassium persulphate (4.38 mg, 0.02 mmol) was added, and the polymerisation is permitted to proceed for another 3 hours at 60° C. and under nitrogen atmosphere before cooling to 20° C.

r) Polymer from methacryloyloxymethyl benzoate

AIBN (0.005 g, 0.03 mmol) was added to a solution of methacryloyloxymethyl benzoate (1.00 g, 4.55 mmol) from Example 1r above in dry THF (8 g) at 60° C. under a dry nitrogen atmosphere. After 24 hours the reaction mixture was cooled to 20° C., and the solvent removed under reduced pressure. The resulting polymer was dissolved in methylene chloride and reprecipitated in methanol. Methanol was separated from the polymer by filtration, resulting in a white powder.

¹H NMR (200 MHz, CDCl₃): δ0.85 (m, 3H, CH₃), 1.87 (m, 2H, CH₂), 5.70 (m, 2H, —OCH₂O—), 7.45 (m, 3H, Ph), 8.05 (m, 2H, Ph).

Size Exclusion Chromatography (SEC): Mw=30281, Mn=11580, Mp=32286, Mw/Mn=2.615.

Differential scanning calorimetry (DSC) indicated that Tg=60.98° C.

s) Free radical polymerisation of N-(2-acetoxymethoxycarbonyloxypropyl)methacrylamide, AIBN (0.0138 g, 0.084 mmol) was added to a solution of N-(2-acetoxymethoxy-carbonyloxypropyl)methacrylamide (0.519 g, 2 mmol) from Example 1s(ii) above in dry THF (8 ml) at 50° C. under a dry nitrogen atmosphere. After 3 days the solvent was removed under reduced pressure to give 0.439 of a white powder.

¹H NMR (200 MHz, CDCl₃): δ0.8–1.2 (m, 3H, CH₃), 1.2–1.4 (m, 3H, CH₂—CH(CH₃)O), 1.6–2.0 (m, 2H, CH₂), 2.1 (s, 3H, CH₃CO), 2.9–3.9 (m, 2H, NH—CH₂), 4.7–5.0 (m, 1H, CH₂CH(CH₃)—O), 5.8 (S, 2H, O—CH₂—O), 6.2–7.0 (m, 1H, NH).

Size Exclusion Chromatography (SEC): Mw=5411, Mn=2857, Mw/Mn=1.894.

Differential scanning calorimetry (DSC) indicated that Tg=52.91° C.

t) Free radical polymerisation of N-[2-(1-acetoxyethoxycarbonyloxy)propyl]methacrylamide AIBN (0.0031 g, 0.189 mmol) was added to a solution of N-[2-(1-acetoyloxyethoxycarbonyloxy)propyl]-methacrylamide (1.23 g, 4.5 mmol) from Example 1t(ii) above in dry THF (18 ml) at 50° C. under a dry nitrogen atmosphere. After 3 days the solvent was removed under reduced pressure. Flash chromatography (step gradient, hexane/ethyl acetate (3:4) to methanol) gave 0.96 g of a white powder.

¹H NMR (200 MHz, CDCl₃): δ0.8–1.2 (m, 3H, CH₃), 1.2–1.4 (m, 3H, CH₂—CH (CH₃)O), 1.5 (d, 3H, O—CH (CH$_3$)O), 1.6–2.0 (m, 2H, CH$_2$), 2.0–2.2 (s, 3H, CH$_3$CO), 2.9–3.9 (m, 2H, NH—CH$_2$), 4.7–5.0 (m, 1H, CH$_2$CH(CH$_3$)—O), 6.2–7.0 (m, 2H, NH+O—CH (CH$_3$)—O).

Size Exclusion Chromatography (SEC): Mw=1991, Mn=1268, Mp=2105, Mw/Mn=1.548.

Differential scanning calorimetry (DSC) indicated that Tg=51.53° C.

u) Oligomer from ethylene di (chloromethyl carbonate) and di-potassium terephthalate Potassium tert. butoxide (1.62 g, 0.014 mol) was added to a solution of terephthalic acid (1.20 g, 0.0072 mol) in DMF (40 ml). Ethylene di (chloromethyl carbonate) (1.78 g, 0.0072 mol) from Example 1v above was added to the resulting suspension. 18-crown-6 (0.056 g, 0.21 mmol) was then added and the reaction mixture was left with stirring at room temperature for 2 days and at 60° C. for 11 days. The reaction mixture was filtered and the solvent was removed under reduced pressure. The residue was dissolved in ethyl acetate (50 ml) and washed with saturated aqueous sodium hydrogen carbonate (30 ml) and water (30 ml). The organic phase was dried (MgSO$_4$) and the solvent removed under reduced pressure to give the title product.

$^1$H NMR (60 MHz, CDCl$_3$): δ4.48 (m, 4H, OCH$_2$CH$_2$O), 6.02 (s, 4H, OCH$_2$O), 8.12 (s, 4H, Ar).

Size Exclusion Chromatography (SEC): Mw=1938, Mn=1511, Mp=2137, Mw/Mn=1.283.

v) Free radical emulsion homopolymerisation of benzyl methacryloyloxymethyl carbonate A solution of sodium dodecyl sulphate (1.6×10$^{-2}$ g, 5.5×10$^{-2}$ mmol) in deoxygenated water (6.0 ml) was added to a 50 ml two necked round bottom flask fitted with magnetic stirring bar and condenser. To the solution, potassium metabisulphite (0.015 g, 6.7×10$^{-2}$ mmol) dissolved in de-oxygenated water (1.0 ml), and benzyl methacryloyloxymethyl carbonate (2.0 g, 8.0 mmol) from Example 1p above were added. The reaction mixture was heated to a temperature of 60° C. To the heated reaction mixture potassium persulphate (1.25×10$^{-3}$ g, 4.6×10$^{-3}$ mmol) was added and the reaction allowed to proceed. After approximately 5 hours the polymerisation was stopped and the polymer emulsion was added dropwise to a large excess of methanol (non-solvent). The polymer was then filtered and washed with methanol and water. This procedure was repeated a total of three times in order to purify the polymer. The polymer was then collected and dried under vacuum to remove any solvent impurities. Some of the stable emulsion was not extracted as above but saved for particle size analysis by light microscopy. The size of the emulsion particles was estimated by optical microscopy and found to be just under 1 μm in diameter.

w)-z) Free radical solution copolymerisation of ethyl methacryloyloxymethyl carbonate and methacrylic acid The monomer feed mixture consisting of ethyl methacryloy-loxymethyl carbonate from Example 1m above and methacrylic acid in DMF (8.0 g) was heated to 60 ° C. and AIBN (0.005 g, 0.03 mol) added. After 24 hours the polymer solution was added dropwise to a stirred excess of chloroform (non-solvent), filtered and washed with more chloroform and dried under reduced pressure.

TABLE 3

| Example 2 | Methacrylic acid (g, mmol) | Ethyl methacryloyloxy methyl carbonate (g, mmol) | Molar ratio methacrylic acid: 1m |
|---|---|---|---|
| w | 0.73, 8.48 | 0.25, 1.33 | 86:14 |
| x | 0.73, 8.48 | 0.17, 0.90 | 90:10 |
| y | 0.73, 8.48 | 0.14, 0.74 | 92:8 |
| z | 0.92, 10.7 | 0.08, 0.43 | 96:4 |

$^1$H NMR (200 MHz, CDCl$_3$): δ10 (s, 6H, 2xCH$_3$), 1.27 (t, 3H, CH$_2$CH$_2$), 1.90 (s, 4H, 2xCH$_2$), 3.52 (bs, 1H, OH ), 4.2 (m,2H, CH$_3$CH$_2$), 5.72 (s, —OCH$_2$O—)

TABLE 4

The solubility of each of the copolymers in hot and cold water.

| Example 2 | Solubility (cold water) | Solubility (hot water) |
|---|---|---|
| w | None | None |
| x | None | None |
| y | None | Some |
| z | Complete * | Complete |

N.B. * Complete solubilisation only after a relatively long period of time undergoing dissolution.

aa) Oligomer from hexamethylene di(chloromethyl carbonate) and di-potassium terephthalate.

Potassium tert. butoxide (7.87 g, 0.068 mol) was added to a solution of terephthalic acid (5.66 g, 0.034 mol) in DMF (200 ml). Hexamethylene di(chloromethyl carbonate) (Example 1x, 9.50 g, 0.034 mol) was added to the resulting suspension. 18-crown-6 (0.24 g, 0.82 mmol) was then added and the reaction mixture was left with stirring at room temperature for 5 hours and at 60° C. for 14 days. The reaction mixture was filtered and the solvent was removed under reduced pressure. The residue was dissolved in chloroform (100 ml) and washed with saturated aqueous sodium hydrogen carbonate (50 ml) and water (50 ml). The organic phase was dried (MgSO$_4$) and the solvent removed under reduced pressure to give a yellow product.

$^1$HNMR (60 MHz, CDCl$_3$): δ1.25–1.90 (m, 8H, 4xCH$_2$), 4.20 (t, 4H, —OCH$_2$CH$_2$), 6.00 (s, 4H, OCH$_2$O), 8.10 (s, 4H, Ar). Size Exclusion Chromatography (SEC): Mw=2987, Mn=1754, Mp=3014, Mw/Mn=1.703.

Differential scanning calorimetry (DSC) indicated that Tg is <20° C.

ab) Polymer from methacryloyloxymethyl acetate

AIBN (0.005 g, 0.03 mmol) was added to a solution of methacryloyloxymethyl acetate (Example 1y, 1.00 g, 4.55 mmol) in dry THF (8 g) at 60° C. under a dry nitrogen atmosphere. After 24 hours the reaction mixture was cooled to 20° C., and the solvent removed under reduced pressure. The resulting polymer was dissolved in CH$_2$Cl$_2$ and reprecipitated in methanol. Methanol was separated from the polymer by filtration, resulting in a white powder.

Differential scanning calorimetry (DSC) indicated that Tg=54.99 ° C.

Size Exclusion Chromatography (SEC): Mw=184678, Mn=2446, Mp=54732, Mw/Mn=7.56 ac) Oligomer from methylene bis(10-hydroxydecanoate) and malonyl chloride

Malonyl chloride (0.254 g, 1.80 mmol) was added to a solution of methylene bis(10-hydroxydecanoate) (Example 1d, 0.700 g, 1.80 mmol) in xylene/trichloroethylene (80:20 by volume, 50 ml) at 60° C. After 77 hours at 60° C. under reduced pressure, the reaction mixture was cooled to 20° C., and the solvent evaporated to give 0.665 g of a brown, viscous liquid.

Size Exclusion Chromatography (SEC): Mw=2700, Mn=2100, Mp=1600, Mw/Mn=1.28 ad) Polymer from ethyl 1-methacryloyloxyethyl carbonate, emulsion polymerisation A mixture of sodium dodecylsulphate (6.5 mg, 0.023 mmol) in water (2.40 ml) and potassium metabisulphite (6.3 mg, 0.028 mmol) in water (0.82 ml) was heated to 60° C. under nitrogen atmosphere, before ethyl 1-methacryloyloxyethyl carbonate (Example 1q(ii), 0.617 g, 3.10 mmol) was added. The polymerisation was initiated by adding potassium persulphate (0.54 mg, 0.002 mmol) in water (0.25 ml). The polymerisation was permitted to proceed for 20 hours at 60° C. under nitrogen atmosphere, before cooling to 20° C.

ae) Polymer from methylene bis(12-hydroxydodecanoate) and triphosgene

A solution of methylene bis(12-hydroxydodecanoate) (Example 1c, 2.0 mmol) and triphosgene (0.67 mmol) in xylene/trichloroethylene 95:5 (2 ml) was heated at 60 ° C. for 36 hours at 50 mmHg and then evaporated to give a polymeric material.

af) Polymer from methylene bis(12-hydroxydodecanoate) and 3,6,9-trioxaundecanedioic acid dichloride A solution of methylene bis(12-hydroxydodecanoate) (Example 1c, 2.0 mmol) and 3,6,9-trioxaundecanedioic acid dichloride (Example 1ab, 2.0 mmol) in xylene/trichloroethylene 95:5 (2 ml) was heated at 60 ° C. for 36 hours at 50 mmHg and then evaporated to give a polymeric material.

aq) Dextran 10-1-(7-carboxyheptanoyloxy)ethyl decyl carbonate

To a solution of dextran 10 (0.65 g) in dry DMSO (40 ml) was added 1-(7-carboxyheptanoyloxy)ethyl decyl carbonate (Example 1ab, 1.5 g, 36 mmol), N-ethyl-N'-(3-dimethylaminopropyl)-carbodiimide (0.83 g, 4.3 mmol) and 4-pyrrolidinopyridine (42 mg, 0.28 mmol) dissolved in dry DMSO (30 ml). After stirring at ambient temperature for 2 days the reaction mixture was diluted with water (250 ml) and dialyzed against water for 30 hours. Lyophilization of the solution yielded 1.3 g of a light yellow coloured powder. In the $^{13}$CNMR spectrum, a new carbonyl signal appeared at 171.28 ppm. This was within the expected region for the ester carbonyl signal from the product. The remaining signals were in accordance with the structure of the product.

ah) Polymer from Pluronic F68 and benzoyloxymethyl chloroformate

Pluronic F68 (9.889 g, 1.191 mmol) was dissolved in toluene (dry, 30 ml). After heating to 45° C., triethylamine (0.70 ml) was added under constant stirring. Benzyloxymethyl chloroformate (Example 1 ae(ii), 1.072 g, 5.00 mmol) dissolved in toluene (4 ml) was added dropwise, followed by further triethylamine (0.25 ml) with toluene (dry, 2.5 ml). The reaction mixture was held at 45° C. for 8 hours, then at 55° C. for 16 hours, then cooled and filtered. The solvent was removed under reduced pressure, and the recovered compound was dissolved in toluene and reprecipitated from n-heptane (500 ml) with stirring, giving a white powder (8.45 g). IR (KBr): 1722 (C=O) cm$^{-1}$.

ai) Free radical polymerisation of 1-Acetoxy-1-phenylmethyl vinyl carbonate

AIBN (0.005 g, 0.03 mol) is added to a solution of 1-acetoxy-1-phenylmethyl vinyl carbonate (Example 1 ad(ii), 1.0 g) in dry THF (8 ml) at 60° C. under a dry nitrogen atmosphere. After 12 hours the solvent is removed under reduced pressure. The resulting polymer is dissolved in CH$_2$Cl$_2$ and reprecipitated in a suitable solvent. The solvent is separated from the solvent by filtration, resulting in a white powder.

aj) Free radical solution co-polymerisation of N-(2-hydroxypropyl)methacrylamide with N-(2-acetoxymethoxycarbonyloxypropyl)methacrylamide N-(2-hydroxypropyl)methacrylamide$^3$ (0.430 g, 3.0 mmol) and N-(2-acetoxymethoxy-carbonyloxypropyl) methacrylamide (Example 1s, 0.778 g, 3.0 mmol) were dissolved in tetrahydrofuran (10 ml) and heated to 55° C. AIBN (0.0207 g, 0.126 mmol) was added, and the mixture was stirred at 55° C. for 3 days to give a clear jelly. This was dissolved in tetrahydrofuran and the solvent evaporated under reduced pressure to give a white powder 1.33 g.

Size Exclusion Chromatography (SEC) indicated formation of polymer.

ak) Polymer from ethylidene bis(16-hydroxyhexadecanoate) and adipoyl chloride

A solution of adipoyl chloride (0.48 g, 2.6 mmol) in xylene/trichloroethylene (80:20 v/v, 5 ml) was added to a solution of ethylidene bis(16-hydroxyhexadecanoate) (1.48 g, 2.6 mmol) from Example 1(af) above in xylene/trichloroethylene (80:20 v/v, 100 ml) at 60° C. After 2 days at 60° C. under reduced pressure (147 mbar), the reaction mixture was cooled to 20° C. The solvent was evaporated under reduced pressure, the resulting polymer was dissolved in chloroform, reprecipitated in hexane and filtered, giving 1.05 g (60%) of the title compound as a white powder. Size Exclusion Chromatography (SEC): Mw=39068, Mh=9442, Mp=48536, Mw/Mn=4.138(using polystyrene as standards).

Differential scanning calorimetry (DSC) indicated that onset melting temperature was 48.61° C. $^1$HNMR (200 MHz, CDCl$_3$): δ1.28 (s, 44H, CH$_2$), 1.45 (d, 3H, CH$_3$CH), 1.62 (m, 12H, CH$_2$), 2.32 (m, 8H, CH$_2$CO), 4.02 (t, 4H, 2 X CH$_2$O), 6.88 (q, 1H, CHCH$_3$).

$^{13}$CNMR (50 MHz, CDCl$_3$): δ20.85, 25.64, 25.68, 25.89, 27.16, 29.84, 30.15, 30.21, 30.44, 30.81, 35.08, 35.12, 35.27, 65.45, 88.98, 171.77 (C=O),173.41(C—O).

al) Random chain-extended polymer of PEG 1500, adipoyl chloride and ethylidene bis(16-hydroxhoxadecanoate) (0.37:1.85:1.75), multiblock To a suspension of ethylidene bis(16-hydroxyhexadecanoate) (1.0g, 1.75 mmol) in dimethoxyethane (10 ml) at room temperature was added freshly distilled adipoyl chloride (270 µl, 1.85 mmol). The temperature of the mixture was gradually raised to 60° C., and a colourless solution obtained. After 5 hours at this temperature PEG 1500 (0.55 g, 0.37 mmol) was added and heating continued for a further 17 hours before the mixture was cooled to room temperature, the solvent evaporated and the solid residue stirred in petroleum ether (bp 40°–60° C.) for 15 minutes and filtered to give the title compound (1.30 g) as a white solid.

am) Extended polymer from PEG 1500 and ethylidene bis[16-(5-chlorocarbonylpentanoyloxy)-hexadecanoate](A-B-A)

Ethylidene bis[16-(5-chlorocarbonylpentanoyloxy) hexadecanoate]prepared as in Example 1(ag) (0.88 g, 1.02 mmol) was dissolved in toluene (15 ml) in a 100 ml 3-necked round bottomed flask equipped with a glass gas inlet tube and a reflux condenser. PEG 1500 (3.06 g, 2.04 mmol) was added and the mixture heated at 60° C. for 22 hours, cooled to room temperature and the solvent removed under reduced pressure to give the title compound (4.12 g) as a white wax.

an) Extended polymer from PEG 1500 and ethylidene bis [16-(5-chlorocarbonylpentanoyloxy)hexadecanoate] multiblock)

The reaction was performed as in Example 2(am), but with ethylidene bis[16-(5-chlorocarbonylpentanoyloxy) hexadecanoate (1.02 g, 1.18 mmol) in toluene (20 ml) and PEG 1500 (1.77 g, 1.18 mmol) to give the title compound (2.29 g) as a white wax.

ao-ar) Extended polymer of PEG, adipic acid and ethylidene bis(16-hydroxyhexadecanoate) (random multiblock)

A solution of PEG 2000 (A), (4.14 g, 2.07 mmol) in 1,1,2-trichloroethylene (26 ml) was added via a syringe to a round bottomed flask containing ethylidene bis(16-hydroxyhexadecanoate) (B) (118 mg, 0.207 mmol), under nitrogen atmosphere. The resulting mixture was heated to 60° C., and when a clear solution had been obtained, adipoyl chloride (C) (417 mg, 2.277 mmol) was added via a syringe. The pressure was reduced to 250 mbar and the solution was stirred at 60° C. over a period of 92 hours. Remaining hydrogen chloride, evolved in the reaction, and the solvent were removed on a rotatory evaporator at reduced pressure and 60° C. for 3 hours, and subsequently under vacuum (<0.1mm Hg) at 60° C. for 24 hours. Finally, the polymer was precipitated from an acetone solution by adding petroleum ether, and cooling in an ice bath for 2 hours. Filtration yielded 3.5 g of the polymer as a white waxy solid.

In total four different block copolymers differing in the molecular weight of the starting PEGs were prepared by this method; the conditions specific for each polymerisation are given in Table 5 below. $^{13}$C NMR- and $^1$H NMR-spectra of the polymers was in agreement with the expected products.

TABLE 5

| Entry | Mw for starting PEG | Molar ratio A:B:C[1] | Solvent | Reaction time (hours) |
| --- | --- | --- | --- | --- |
| ao | 400 | 10:1:11 | Diglyme-xylene | 21 |
| do | 600 | 10:1:11 | Diglyme | 24 |
| aq | 1500 | 10:1:11 | DME | 21 |
| ar | 2000 | 10:1:11 | Trichloroethylene | 92 |

[1]The letters refers to the reactants as specifed in the text above.

as) PEG 2300 methyl ether 16-hexadecanoyloxyhexadecanoate

PEG 2300 methyl ether (10.000g, 4.35 mmol) was dissolved in tetrahydrofuran (90 ml) and pyridine (0.413 g, 5.22 mmol) was added. 16-hexadecanoyloxyhexadecanoyl chloride (2.301 g, 4.35 mmol) was dissolved in tetrahydrofuran (10 ml) and added dropwise. After stirring for 3 days at room temperature, the mixture was filtered and the solvent was evaporated under reduced pressure. The residue (12.08 g) was purified on a silica column, eluted with chloroform with increasing methanol concentration (from 1% to 3% methanol in chloroform) to give 5.20g (43%) of the title compound. $^1$H NMR (300 MHz, CDCl$_3$): δ0.80–0.87 (m, CH$_3$), 1.21 (s, br), CH$_2$), 1.53–1.62 (m, CH$_2$), 2.20–2.35 (m, CH$_2$CO), 3.34 (s, CH$_{3O}$), 3.61 (s, OCH$_2$CH$_2$O), 4.02 (t, COOCH$_2$CH$_2$O), 4.19 (t, COOCH$_2$CH$_2$O). $^{13}$C NMR (75 MHz, CDCl$_3$): δ13.95, 22.49, 24.71, 24.83, 25.74, 28.45, 28.95, 29.07, 29.16, 29.28, 29.34, 29.40, 29.46, 31.72, 34.05, 34.21, 58.85, 63.15, 64.19, 69.01, 70.37, 71.73, 173.64, 173.82.

at) PEG 5000 methyl ether 16-hexadecanoyloxyhexadecanoate)

PEG 5000 methyl ether (7.500 g, 1.50 mmol) was dissolved in toluene (90 ml) and dried by refluxing in a Dean Stark apparatus. Pyridine (0.143 g, 1.80 mmol) was added followed by addition (dropwise) of 16-hexadecanoytoxyhexadecanoyl chloride (1.191 g, 2.25 mmol) dissolved in toluene (10 ml). The mixture was heated to reflux and after stirring under reflux for 3 days the mixture was cooled to room temperature and precipitated into hexane. After filtering, the precipitate was washed with hexane and dried (MgSO$_4$). After evaporation under reduced pressure, the residue was purified on a silica column, eluted with chloroform with increasing methanol concentration (from 1% to 3% methanol in chloroform) to give 5.93 g (72%) of the title compound. mH NMR (300 MHz, CDCl$_3$): δ0.82–0.86 (m, CH$_3$), 1.22 (s, (br), CH$_2$), 1.53–1.62 (m, CH$_2$), 2.20–2.35 (m, CH$_2$CO), 3.34 (s, CH$_3$O), 3.61 (s, OCH$_2$CH$_2$O), 4.01 (t, COOCH$_2$CH$_2$O), 4.18 (t, COOCH$_2$O). $^{13}$C NMR (75 MHz, CDCl$_3$): δ13.66, 22.21, 24.43, 24.54, 25.46, 28.17, 28.67, 28.79, 28.87, 28.99, 29.06, 29.11, 29.17, 31.44, 33.73, 33.93, 58.57, 62.87, 63.90, 68.72, 69.62, 69.86, 70.09, 71.45, 76.85, 173.35, 173.53.

au) PEG 10000 methyl ether 16-hexadecanoyloxydexadecanoate

PEG 10000 methyl ether (7.500 g, 0.75 mmol) was dissolved in toluene (140 ml) and pyridine (0.107 g, 1.35 mmol) was added. The solution was heated to 60° C. and 16-hexadecanoyloxyhexadecanoyl chloride (0.595 g, 1.12 mmol) dissolved in toluene (10 ml) was added dropwise. The mixture was heated to reflux and after stirring under reflux for 3 days the mixture was cooled to room temperature and precipitated into hexane. After filtering, the precipitate was washed with hexane and dried. Flash chromatography on a silica column, eluted with 5% methanol in chloroform, gave 5.39 g (68%) of the title compound. $^1$H NMR (300 MHz, CDCl$_3$): δ0.84 (t, CH$_3$), 1.21 (s, (br), CH$_2$), 1.55–1.60 (m, CH$_2$), 2.20–2.35 (m, CH$_2$CO), 3.34 (s, CH$_{3O}$), 3.61(s, OCH$_2$CH$_2$O), 4.01 (t, COOCH$_2$CH$_2$O), 4.18 (t, COOCH$_2$CH$_2$O). $^{13}$C NMR (75 MHz, CDCl$_3$): δ13.94, 22.48, 24.70, 24.82, 25.73, 28.94, 29.05, 29.14, 29.26, 29.33, 29.39, 29.45, 31.71, 34.00, 58.84, 63.14, 68.99, 69.36, 69.86, 69.97, 70.01, 70.36, 70.74, 70.82, 70.86, 71.72, 77.10, 173.62, 173.80.

av) 16-[ω-Methoxy-PEG 2000-carbonyloxy] hexadecanoic acid 1-[16-(16-hexadecanoyloxyhexadecanoyloxy)hexadecanoyloxy]ethyl ester Methoxy PEG 2000 chloroformate (1.90g, 0.95 mmol) was dissolved in toluene (90 ml), and pyridine (0.09 g, 1.13 mmol) was added. 1[[16-(16-hexadecanoyloxyhexadecanoyloxy)hexadecanoyloxy]ethyl 16-hydroxyhexadecanoate (1.00 g, 0.95 mmol) was dissolved in toluene (10 ml) and added dropwise. The mixture was heated to reflux and after stirring under reflux for 10 hours, the mixture was cooled to room temperature and filtered. The solvent was evaporated under reduced pressure. The residue was purified on a silica column using chloroform containing 2% methanol, to give 1.00 g (35%) of the title compound. $^1$H-NMR (300 MHz, CDCl$_3$): δ0.85 (t, CH$_3$), 1.20–1.33 (m, CH$_2$), 1.45 (d, —O—CH(CH$_3$)—O), 1.5–1.7 (m, CH$_2$), 2.0 (H$_2$O), 2.2–2.3 (m, —CH$_2$—C(O)—O), 3.35 (s, CH$_3$—O—), 3.5–3.7 (s, —OCH$_2$CH$_2$O—), 4.03 (t, —C(O)—O—CH$_2$—), 4.10 (t, —CH$_2$—O—C(O)—O—), 4.26 (m, —O—C(O)—O—CH$_2$—CH$_2$—O—), 6.8–6.9 (q, —O—CH(CH$_3$)—O). $^{13}$C-NMR (75 MHz, CDCl$_3$): δ13.7, 19.2, 22.1, 24.2, 24.6, 25.2, 25.5, 28.2–29.2, 31.5, 33.9, 34.0, 58.7, 64.0, 66.3, 67.9, 68.5, 70.0, 71.5, 87.9, 171.5, 173.7.

aw) 16-[ω-Methoxy PEG 5000 carbonyloxy] hexadecanoic acid 1-[16-(16-hexadecanoyloxyhexadecanoyloxy)hexadecanoyloxy]ethyl ester Methoxy PEG 5000 chloroformate (8.50 g, 1.70 mmol) was dissolved in toluene (90 ml) and pyridine (0.146 g, 1.85 mmol) was added. 1-[16-(16-Hexadecanoyloxyhexadecanoyloxy)ethyl 16-hydroxyhexadecanoate (1.79 g, 1.70 mml) was dissolved in toluene (10 ml) and added dropwise. The mixture was heated to reflux and after stirring under reflux for 3 days the mixture was cooled to room temperature and filtered. The solvent was evaporated under reduced pressure and the residue was purified on a silica column, eluted with chloroform with increasing methanol concentration (from 3% to 5% methanol in chloroform) to give 3.90g (38%) of the title compound. $^1$H-NMR (300 MHz, CDCl$_3$): δ0.85 (t, CH$_3$), 1.20–1.33 (m, CH$_2$), 1.45 (d, —O—CH(CH$_3$)—O), 1.5–1.7 (m, CH$_2$), 1.8 (H$_2$O), 2.2–2.3 (m, —CH$_2$—C(O)—O), 3.35 (s, CH$_3$—O—) 3.5–3.7 (s, —OCH$_2$CH$_2$O—), 4.03 (t, —C(O)—O—CH$_2$—), 4.10 (t, —CH$_2$—O—C(O)—O—), 4.26 (m, —O—C(O)—O—CH$_2$—CH$_2$—O—), 6.8–6.9 (q, —O—CH (CH$_3$)—O).

ax) 16-[ω-Methoxy PEG 10000 carbonyloxy] hexadecanoic acid 1-[16-(16-hexadecanoyloxyhexadecanoyloxy) hexadecanoyloxy]ethyl ester Methoxy PEG 10000 chloroformate (7.50 g, 0.75 mmol) was dissolved in toluene (90 ml), and pyridine (0.063 g, 0.80 mmol) was added. 1-[16-(16-Hexadecanoyloxyhexadecanoyloxy]ethyl 16-hydroxyhexadecanoate (0.79 g, 0.75 mmol) was dissolved in toluene (10 ml) and added dropwise. The mixture was heated to reflux and after stirring under reflux for 3 days the mixture was cooled to room temperature and filtered. The solvent was evaporated off under reduced pressure. The residue was purified on a silica column, eluted with chloroform with increasing methanol concentration(from 3% to 5% methanol in chloroform) to give 1.60g (19%) of the title compound. $^1$H-NMR (300 MHz, CDCl$_3$): δ0.85 (t, CH$_3$), 1.20–1.33 (m, CH$_2$), 1.45 (d, —O—CH(CH$_3$)—O), 1.5–1.7 (m, CH$_2$), 2.2–2.3 (m, —CH$_2$—C(O)—O), 3.35 (s, CH$_3$—O—), 3.5–3.7 (s, —OCH$_2$CH$_2$O—), 4.03 (t, —C(O)—O—CH$_2$), 4.10 (t, —CH$_2$—O—C(O)—O—), 4.26 (m, —O—C(O)—O—CH$_2$—CH$_2$—O—), 6.8–6.9 (q, —O—CH(CH$_3$)—O).

EXAMPLE 3

Preparation of polymer particles a) Particles from polymer made of methylene dimethacrylate and styrene A sample (13 ml) of the polymer emulsion from Example 2a above was mixed with heptane (13 ml) at room temperature. After 40 minutes the sample was lyophilised to yield the product as a white powder.

b) Particles from polymer made from methylene bis(16-hydroxyhexadecanoate) and adipoyl chloride 6.204 g of a 4.1% wt/wt solution of polymer from Example 2b above in a mixture of xylene/trichloroethylene (90:10) was added to 25 ml of a 0.5% wt/vol solution of Pluronic® F68 in water. The mixture was vigorously shaken (by hand) for one minute and freeze dried for 16 hours. Light microscopy indicated formation of microparticles.

c) Particles from polymer made from methylene bis(16-hydroxyhexadecanoate) and adipoyl chloride 6.204 g of a 4.1% wt/wt solution of polymer from Example 2b above in a mixture of xylene/trichloroethylene (90:10) was added to 25 ml of a 0.5% wt/vol solution of Pluronic® F68 in water. The mixture was mixed with an Ultra Turax T25 mixer at speed 20500 rpm for 40 seconds and freeze dried for 16 hours. Light microscopy indicated formation of microparticles.

d) Particles from polymer made from methylene bis(16-hydroxyhexadecanoate) and adipoyl chloride 12.408 g of a 4.1% wt/wt solution of polymer from Example 2b above in a mixture of xylene/trichloroethylene (90:10) was added to 50 ml of a 0.5% wt/vol solution of Pluronic® F68 in water. The mixture was mixed with an Ultra Turax T25 mixer at speed 24000 rpm for 40 seconds and freeze dried for 16 hours. Light microscopy indicated formation of microparticles.

e) Particles from polymer made from methylene bis(12-hydroxydodecanoate) and adipoyl chloride The polymer from methylene bis(12-hydroxydodecanoate) from Example 2c above and adipoyl chloride (0.40 g) in a mixture of xylene/trichloroethylene ((10:1), 4 ml) was added to 20 ml of a 0.5% wt/vol solution of Pluronic® F68 in water. The mixture was mixed with an Ultra Turax T25 mixer at speed 20500 rpm for 30 seconds and freeze dried (0.5 mmHg) for 16 hours. Light microscopy indicated formation of microparticles.

f) Particles from oligomer made from ethylene di(chloromethyl carbonate) and di-potassium terephthalate A solution of oligomer from ethylene di(chloromethyl carbonate) and di-potassium terephthalate from Example 2u above in chloroform (22.5 ml of a 4% wt/vol solution made by dissolving the polymer under careful heating) was added to 30 ml of a 0.5% wt/vol solution of Pluronic® F68 in water. The mixture was mixed with an Ultra Turax T25 mixer at speed 24000 rpm for 40 seconds and freeze dried for 16 hours. Light microscopy indicated formation of micro-particles.

g) Particles from polymer made from ethyl methacryloyloxymethyl carbonate

A solution of polymer made from ethyl methacryloyloxymethyl carbonate from Example 2j above in chloroform (9 ml of a 10% wt/vol solution) was added to 30 ml of a 0.5% wt/vol solution of Pluronic® F68 in water. The mixture was mixed with an Ultra Turax T25 mixer at speed 24000 rpm for 40 seconds and freeze dried for 16 hours. Light microscopy indicated formation of microparticles.

h) Particles from polymer made from methyl 1-methacryloyloxyethyl carbonate

The polymer from methyl 1-methacryloyloxyethyl carbonate (0.462 g) from Example 2o above in toluene (5 ml) was added to 20 ml of a 1.0% wt/vol solution of Pluronic® F68 in water. The mixture was mixed with an Ultra Turax T25 mixer at speed 20500 rpm for 30 seconds and freeze dried (0.05 mmHg) for 16 hours. Light microscopy indicated formation of microparticles.

i) Particles from polymer made from methacryloyloxymethyl benzoate

The polymer from methacryloyloxymethyl benzoate (0.45 g) from Example 2r above in a mixture of toluene/trichloroethylene ((10:1), 2 ml) was added to 20 ml of a 1.0% wt/vol solution of Pluronic® F68 in water. The mixture was mixed with an Ultra Turax T25 mixer at speed 20500 rpm for 30 seconds and freeze dried (0.05 mmHg) for 4 hours. Light microscopy indicated formation of microparticles.

j) Particles from polymer made from ethyl methacryloyloxymethyl carbonate

The polymer emulsion was prepared according to Example 2q above. 14.783 g of the emulsion was added to 47.305 g of toluene. The mixture was vigorously stirred for 20 hours and freeze dried in 16 hours giving 1.813 g of a white powder. Light microscopy and scanning electron microscopy indicated formation of microparticles.

k) Particles from polymer made from ethyl methacryloyloxymethyl carbonate

The polymer emulsion was prepared according to Example 2q above. 12.7612 g of the emulsion was added to 40.836 g of chloroform. The mixture was vigorously stirred for 20 hours and freeze dried for 16 hours giving 1.496 g of a white powder. Light microscopy and scanning electron microscopy indicated formation of microparticles.

l) Particles from oligomer made from ethylene di(chloromethyl carbonate) and di-potassium terephthalate Oligomer from ethylene di(chloromethyl carbonate) and di-potassium terephthalate (1.0 g) from Example 2u above was dissolved in 19.0 g of liquid naphthalene at 100° C. The naphthalene solution was emulsified at 90° C. into 200 ml of a water solution of polyvinyl alcohol (8.0 g, Mw=13000–23000) containing Pluronic® F68 (0.2 g). The emulsifying head was an Ultra Turax T25. Then the emulsion was diluted under agitation with 500 ml of the same aqueous phase at 15° C. and mixed for 8 minutes. The naphthalene droplets solidified into beads which were filtered through a 50 μm filter to separate particles greater than 50 μm. The suspension was centrifuged under 1000 xg and the beads were washed with water and recentrifuged. This step was repeated twice. The beads were resuspended in 100 ml of water with 0.8 g lactose and the suspension was frozen into a block at –40° C. The block was thereafter freeze dried for 16 hours. Light microscopy indicated formation of microparticles.

m) Particles from polymer made from methylene bis(16-hydroxyhexadecanoate) and adipoyl chloride 3 ml of a 3.37% wt/vol solution of the polymer (Example 2b) in a mixture of xylene/trichloroethylene (90:10) was added to 10 ml of a 0.5 wt % solution of Tween® 80 in water. The mixture was mixed with an Ultra Turax® T25 mixer at speed 20500 rpm for 1 minute and 30 seconds, and freeze dried for 18 hours, giving a white powder. Light microscopy indicated formation of microparticles.

n) Particles from polymer made from methylene bis(16-hydroxyhexadecanoate) and adipoyl chloride 3 ml of a 3.37% wt/vol solution of the polymer (Example 2b) in a mixture of xylene/trichloroethylene (90:10) was added to 10 ml of a 0.5 wt % solution of Brij® 99 in water. The mixture was mixed with an Ultra Turax® T25 mixer at speed 20500 rpm for 1 minute and 30 seconds, and freeze dried for 17 hours, giving a white powder. Light microscopy indicated formation of microparticles.

o) Particles from polymer made from methylene bis(16-hydroxyhexadecanoate) and adipoyl chloride.

5.5 ml of a 1.84% wt/vol solution of the polymer (Example 2b) in a mixture of xylene/trichloroethylene (90:10) was added to 10 ml of a 0.5 wt % solution of Cremophor® RH40 in water. The mixture was mixed with an Ultra Turax® T25 mixer at speed 20500 rpm for 1 minute and 30 seconds, and freeze dried for 16 hours, giving a white powder. Light microscopy indicated formation of microparticles.

p) Particles from polymer made from methylene bis(16-hydroxyhexadecanoate) and adipoyl chloride 5.5 ml of a 1.84% wt/vol solution of the polymer (Example 2b) in a mixture of xylene/trichlororethylene (90:10) was added to 10 ml of a 0.5 wt % solution of Kollidon® 30 in water. The mixture was mixed with an Ultra Turax® T25 mixer at speed 20500 rpm for 1 minute and 30 seconds, and freeze dried for 16 hours, giving a white powder. Light microscopy indicated formation of microparticles.

q) Particles from polymer made from methylene bis(10-hydroxydecanoate) and adipoyl chloride 4 ml of a 2.52% wt/vol solution of the polymer (Example 2f) in a mixture of xylene/trichloroethylene (90:10) was added to 10 ml of a 0.5 wt % solution of Pluronic® F68 in water. The mixture was mixed with an Ultra Turax® T25 mixer at speed 20500 rpm for 1 minute and 30 seconds, and freeze dried for 15 hours, giving a white powder. Light microscopy indicated formation of microparticles.

r) Particles from oligomer from hexamethylene di(chloromethyl carbonate) and di-potassium terephthalate 22.5 ml of a 4% wt/vol solution of the polymer (Example 2aa) in chloroform was added to 30 ml of a 0.5 wt % solution of Pluronic®F68 in water. The mixture was mixed with an Ultra Turax® T25 mixer at speed 24000 rpm for 40 seconds, and freeze dried for 16 hours, giving a yellow, rubbery solid. Light microscopy indicated formation of microparticles.

s) Particles from polymer made from N-[2-(1-acetoxyethoxycarbonyloxy)propyl]methacrylamide 8 ml of a 2.55% wt/vol solution of the polymer (Example 2t) in xylene/trichloroethylene (90:10) was added to 20 ml of a 0.5 wt % solution of Pluronic® F68 in water. The mixture was mixed with an Ultra Turax® T25 mixer at speed 20500 rpm for 1 minute and 30 seconds, and freeze dried for 16 hours, giving a white powder. Light microscopy indicated formation of microparticles.

t) Particles from polymer made from methacryloyloxymethyl acetate 8 ml of a 2.48% wt/vol solution of the polymer (Example 2ab) in xylene/trichloroethylene (90:10) was added to 20 ml of a 0.5 wt % solution of Pluronic® F68 in water. The mixture was mixed with an Ultra Turax® T25 mixer at speed 20500 rpm for 1 minute and 30 seconds, and freeze dried for 16 hours, giving a white powder. Light microscopy indicated formation of microparticles.

u) Particles from polymer made from N-(2-aetoyloxymethoxycarbonyloxypropyl) methacrylamide 4 ml of a 2.54% wt/vol solution of the polymer (Example 2s) in chloroform was added to 10 ml of a 0.5 wt % solution of Pluronic® F68 in water. The mixture was mixed with an Ultra Turax® T25 mixer at speed 24000 rpm for 50 seconds, and freeze dried for 16 hours, giving a white powder. Light microscopy indicated formation of microparticles.

v) Particles from polymer made from ethyl 1-methacryloyloxyethyl carbonate

The polymer emulsion was prepared according to emulsion polymerisation of polymer from ethyl 1-methacryloyloxyethyl carbonate (Example 2ad). 2.00 g of the emulsion was added to 7.41 g of toluene. The mixture was vigorously stirred for 20 hours and freeze dried in 16 hours giving 0.250 g of a white powder. Light microscopy indicated formation of microparticles.

w) Particles from polymer made from ethyl 1-methacryloyloxyethyl carbonate

The polymer emulsion was prepared according to emulsion polymerisation of polymer from ethyl 1-methacryloyloxyethyl carbonate (Example 2ad). 2.00 g of the emulsion was added to 6.40 g of chloroform. The mixture was vigorously stirred for 20 hours and freeze dried in 16 hours giving 0.250 g of a white powder. Light microscopy indicated formation of microparticles.

x) Particles from polymer made from butyl methacryloyloxymethyl carbonate,

The polymer from butyl methacryloyloxymethyl carbonate (Example 2k, 0.45 g ) was dissolved in toluene (9 ml). Water (30 ml) containing 0.3g Pluronic® F68 was added and an emulsion was made using an Ystral® homogenizer at 2000 rpm for 30 seconds. The emulsion was freeze dried for 19 hours and light microscopy indicated formation of microparticles.

y) HSA-coated particles from the polymer made from methacryloyloxymethyl benzoate The polymer made from methacryloyloxy methyl benzoate (Example 2r, 0.9 g) was dissolved in toluene (9 ml). An aqueous solution of 5% human serum albumin (HSA—30 ml) was added and the mixture homogenized using an Ystral® homogenizer at 20000 rpm for 30 s. The resulting emulsion was freeze dried for 16 hours. Light microscopy indicated formation of microparticles.

z) Polyoxyethylene—coated particles from the polymer made from methacryloxyoxy methyl benzoate A di-block copolymer consisting of one block polymethyl methacrylate ( Mw=1000 ) and one block polyoxyethylene (POE, Mw=2000 ) (0.4 g) was dissolved in toluene (9 ml). The polymer made from methacryloyloxymethyl benzoate (Example 2r, 0.9 g) was then dissolved in the toluene solution. 30 ml water was added and the mixture was homogenized using an Ystral® homogenizer at 20000 rpm for 30 seconds. The resulting emulsion was freeze dried for 16 hours yielding POE-coated microparticles.

aa) Particles from polymer made from methyl methacryloyloxymethyl carbonate

The polymer made from methyl methacryloyloxymethyl carbonate (Example 2o, 0.9 g) was dissolved in toluene (9 ml). A mixture of sodium dodecylsulphate (0.3 g) and Pluronic® F68 (0.025 g) in water (35 ml) was added and the solution was homogenized using an Ystral® homogenizer at 20000 rpm for 30 seconds. The emulsion was freeze dried for 16 hours and light microscopy indicated formation of microparticles.

ab) Particles from polymer made from methylene bis (12-hydroxydodecanoate) and 3,6,9-trioxaunedecanedioic acid The polymer made from methylene bis (12-hydroxydodecanoate) and 3,6,9-trioxaunedecanedioic acid dichloride (Example 2af , 0.9 g) was dissolved in toluene (9ml). Water (30 ml) containing Pluronic® F68 (0.3 g) was added and the mixture homogenized for 30 seconds using an Ystral® homogenizer at 20000 rpm. The emulsion was freeze dried for 48 hours. Light microscopy indicated formation of microparticles.

ac) Particles from spray drying of polymer from methacryloyloxymethyl benzoate 0.72 g of the polymer from Example 2r above was dissolved in 60 g dichtoromethane. The solution was spray dried in a Büchi 190 mini spray dryer. The inlet temperature was set to 54° C., and the outlet temperature was measured as 40° C. Light microscopy indicated formation of microparticles.

ad) Pluronic® F68 coated particles obtained from spray drying of polymer made from methylene bis(16-hydroxyhexadecanoate) and adipoyl chloride 1.71 g of a mixture of the polymer from Example 2b above and Pluronic® F68 (50:50) was dissolved in 100 ml dichloromethane. The solution was spray dried in a Büchi 190 mini spray drier. The inlet temperature was set to 50° C., and the outlet temperature was measured as 42° C. Light microscopy indicated formation of microparticles.

ae) Coating of particles made of polymer from methylene bis(16-hydroxyhexadecanoate) and adipoyl chloride Particles prepared according to Example 3c above were redispersed in several aqueous solutions of different coating materials and at different concentrations, as shown in Table 6. Light microscopy indicated an improved dispersion with reduced tendency of aggregation.

TABLE 6

| Coating material | Concentration [% (wt/wt)] |
| --- | --- |
| Tween ® 60 | 0.1, 0.5 |
| Sodium Hexadecanoate | 0.1, 0.5 |
| Cetyl trimethyl ammonium chloride | 0.1, 0.5 |
| Kollidon ® 30 (Polyvinyl pyrrolidone) | 0.2, 1.0 |
| Cremophor ® RH40 | 0.2, 1.0 |
| Pluronic ® F68 | 1.0 | af) Pluronic® F68 coated particles from polymer from methyl methacryloyloxymethyl carbonate The polymer from methyl methacryloyloxymethyl carbonate (Example 2i, 0.9 g) is dissolved in toluene (9 ml). Water (30 ml) containing cetyl trimethyl ammonium chloride (0.4 g) is added, and the mixture homogenized using an Ystral®homogenizer. The emulsion is freeze dried for 24 hours. The obtained particles are washed several times with distilled water in order to remove the surfactant. After the last washing, the particles are freeze dried for 24 hours.

ag) Particles from polymer made from ethylidene bis(16-hydroxyhexadecanoate) and adipoyl chloride 10 ml of a 5% w/v solution of the polymer (Example 2ak) in toluene was added to 30ml of a 5 wt % solution of Human Serum Albumin in water. The mixture was mixed with an Ultra Turax® T25 mixer at 20,000 rpm for 1 minute, frozen on a dry ice/methanol bath and lyophilized for 18 hours, giving a slightly yellow powder. Light microscopy indicated formation of microparticles.

ah) Particles from polymer made from ethylidene bis(16-hydroxyhexadecanoate) and adipoyl chloride 10 ml of a 10% w/v solution of the polymer (Example 2ak) in p-xylene was added to 30ml of a 5 wt % solution of Human Serum Albumin in water. The mixture was mixed with an Ultra Turax® mixer at 20.000 rpm for 1 minute and 30 seconds, frozen on a dry ice/methanol bath and lyophilized for 18 hours, giving a white powder. Light microscopy indicated formation of microparticles.

ai) Particles from polymer made from ethylidene bis(16-hydroxyhexadecanoate) and adipoyl chloride 10 ml of a 5% w/v solution of the polymer (Example 2ak) in p-xylene was added to 30ml of a 5 wt % solution of modified starch (Lyckeby, Sweden, PU-24,000) in water. The mixture was mixed with an Ultra Turax® T25 mixer at 20,000 rpm for 1 minute and 30 seconds, frozen on a dry ice/methanol bath and lyophilized for 18 hours, giving a white powder. Light microscopy indicated formation of microparticles.

Particles from polymer made from ethylidene bis(16-hydroxyhexadecanoate) and adipoyl chloride 10 ml of a 5% w/v solution of the polymer (Example 2ak) in p-xylene was added to 30ml of a 0.8 wt % solution of poly(vinyl alcohol) in water. The mixture was mixed with an Ultra Turax® T25 mixer at 20,000 rpm for 1 minute, frozen on a dry ice/methanol bath and lyophilized for 18 hours, giving a white powder. Light microscopy indicated formation of microparticles.

ak) Particles from polymer made from ethylidene bis(16-hydroxyhexadecanoate) and adipoyl chloride 10 ml of a 5% w/v solution of the polymer (Example 2ak) in p-xylene was added to 30ml of a 1 wt % solution of gelatin in water. The mixture was mixed with an Ultra Turax® T25 mixer at 20,000 rpm for 1 minute, frozen on a dry ice/methanol bath and lyophilized for 18 hours, giving a white powder. Light microscopy indicated formation of microparticles.

al) Particles from polymer made from ethylidene bis(16-hydroxyhexadecanoate) and adipoyl chloride 5 ml of a 5% w/v solution of the polymer (Example 2ak) in (−)-camphene maintained at 60° C. was added to 15 ml of a 5 wt % solution of human serum albumin in water at the same temperature. The mixture was mixed hot with an Ultra Turax® T25 mixer at 20,000 rpm for 1 minute, frozen on a dry ice/methanol bath and freeze dried for 48 hours, giving a white powder. Light microscopy indicated formation of microparticles.

am-at) Particles from polymer made from ethylidene bis(16-hydroxyhexadecanoate) and adipoyl chloride, stabilized in dispersion with block copolymer General description 10 ml of a 5% w/v solution of the polymer (Example 2 ak) in (−)-camphene maintained at 60° C. was mixed with 30 ml of an aqueous solution of block copolymer from Example 2 above (see Table 7) at the same temperature and with concentrations as given in Table 7. The mixture was mixed with a rotor-stator mixer (Ultra Turax® T25) at slow speed for several minutes, frozen on a dry ice/methanol bath, and lyophilized for 48 hours, giving a white powder.

TABLE 7

| Example 3 | Block copolymer from Example 2 | Conc. [% w/w] |
|---|---|---|
| am | an | 1 |
| an | an | 2 |
| ao | ar | 1 |
| ap | ar | 2 |
| aq | at | 1 |
| ar | au | 1 |
| as | av | 2 |
| at | ax | 2 |

EXAMPLE 4

Acoustic characterizations, General procedure

The dry powders of polymer particles prepared according to Example 3 above were redispersed in an aqueous solvent by shaking on a laboratory shaker for 12–16 hours. Examination by light microscopy indicated formation of particle dispersions. The particles floated readily, as expected for gas containing particles.

The acoustic effect of the suspensions above was obtained by measuring the ultrasonic transmission through suspensions of different concentrations (mg/ml) in an aqueous carrier liquid, using a 3.5 MHz broadband transducer in a pulse-reflection technique. Pure carrier liquid was used as reference, and measurements were performed along a dilution line where the starting suspension was successively diluted with the carrier liquid. Measurements were done until the signal was reduced to approximately 3–5 db/cm. The obtained acoustic effects were at a level such that the products can be expected to be useful as ultrasound contrast agents. According to theoretical considerations, solid (as opposite to gas containing) particles of the same size and at the same dilutions should give an acoustic attenuation of less than 0.1 db/cm.

a) Characterization of particles from polymer made from copolymerization of methylene dimethacrylate and styrene The particles were from a polymer made from copolymerization of methylene dimethacrylate and styrene. The product showed a strong effect on the acoustic transmission, decreasing with increasing dilution volume, as can be seen in FIG. 1 in the accompanying drawing.

b-i) Characterization of various polymer particles

The results are summarized in Table 8 and FIG. 2–9 in the accompanying drawings.

Table 8

Acoustic measurements of particles from Example 3 above. The acoustic measurements are given in column 3 as the concentration where the contrast effect was measured as 8 db/cm, i.e half value of saturated signal. At higher concentrations, the signal intensity increased until saturation was observed.

| Example 4 | Particles, Example 3, aq. medium. | Particle conc. [mg/ml] at 8 db/cm | Figure no. in acc. drawings. |
|---|---|---|---|
| b | b, 0.9% (wt/wt) NaCl (aq) | 0.9 | 2 |
| c | c, 0.9% (wt/wt) NaCl (aq) | 0.2 | 3 |
| d | d, 0.9% (wt/wt) NaCl (aq) | 0.5 | 4 |
| e | h, Water | 1.0 | 5 |
| f | i, Water | 0.9 | 6 |
| g | y, Water | 0.1 | 7 |
| h | z, Water | 0.5 | 8 |
| i | ac, HSA/Water | 2.5 | 9 |
| j | ag, water | 1.0 | — |
| k | ah, water | 0.12 | — |
| l | al, water | 0.03 | — |
| m | aj, water | 0.16 | — |
| n | ak, water | 0.35 | — |
| o | al, water | 0.15 | — |
| p | am, water | 0.04 | — |
| q | an, water | 0.02 | — |
| r | ao, water | 0.02 | — |
| s | ap, water | 0.02 | — |
| t | aq, water | 0.03 | — |
| u | ar, water | 0.01 | — |
| v | as, water | 0.09 | — |
| w | at, water | 0.08 | — |

EXAMPLE 5

In-vivo characterization General procedure 1

Dry powder of polymer particles described in Example 3 were redispersed in a sterile 0.9% (wt/wt) NaCl (aq) solution by shaking on a laboratory shaker for 12–16 hours. The dispersions were injected in chinchilla rabbits, and measured by using a doppler technique where an ultrasound probe was placed directly on a carotid artery and the inferior caval vein. The particle dispersions were injected in an ear vein. Signal height and duration were recorded. The obtained signal heights were significant, indicating a strong in vivo ultrasound contrast effect for the dispersions. The long duration of the signal reveals that the in vivo stability is good.

Table 9

In vivo characterization of polymer particles. The doses are in µg particles per kg body weight. The signal intensity is measured in doppler units [DU].

| Example 5 | Particles Example 3 | Conc. [mg/ml] | Dose [µg/kg] | Artery Peak [DU] | Artery Duration [s] | Vein Peak [DU] | Vein Duration [s] |
|---|---|---|---|---|---|---|---|
| a | b | 4.8 | 320 | 0.5 | | | |
| b (i) | c | 4.6 | 307 | 1.9 | 6 | 0.8 | |
| b (ii) | c | 4.6 | 767 | 5.6 | 39 | 2.8 | |
| c | d | 3.7 | 247 | 0.6 | | | |
| d (i) | i | 2.1 | 139 | 1.7 | 5 | | |
| d (ii) | i | 2.1 | 347 | 3.2 | 13 | 1.2 | 70 |
| d (iii) | i | 2.1 | 693 | 3.1 | 10 | 2.1 | 120 |
| e (i) | h | 2.0 | 136 | 0.5 | | | |
| e (ii) | h | 2.0 | 340 | 1.0 | 5 | | |
| e (iii) | h | 2.0 | 680 | 1.4 | 5 | 0.7 | |
| f (i) | y | 2.1 | 140 | 2.8 | 8 | 0.5 | |
| f (ii) | y | 2.1 | 350 | 3.7 | 11 | 0.8 | 44 |
| f (iii) | y | 2.1 | 700 | 5.3 | 33 | 0.8 | 74 |
| g (i) | z | 2.0 | 133 | 1.6 | 7 | 0 | |
| g (ii) | z | 2.0 | 333 | 3.6 | 32 | 0.7 | 74 |
| g (iii) | z | 2.0 | 666 | 5.3 | 79 | 1.6 | 99 |

General procedure 2:

Dry powders of polymer particles described in Examples 3 ag, 3 ah, 3 ai, 3 aj, 3 ak and 3 al were redispersed in sterile 0.9% (w/w) NaCl(aq) solution by shaking on a laboratory shaker for 12-16 hours. The dispersions were injected in leg veins of dogs, and short axis transthoracic echocardiac images were obtained using a Vingmed Sound CFM750 ultrasonic scanner at 5 MHz. The image sequences were stored on video. The particle dispersions all caused very sharp contrast enhancement in both ventricles, and also caused significant myocardial contrast enhancement (MCE), visible on live video sequences. MCE was demonstrated in the anterior and posterior walls. The duration of contrast effect reveals that the particle dispersions circulated in vivo for several minutes after injection. The presence of myocardial contrast and the long duration of contrast indicates that the in vivo stability is very good.

EXAMPLE 6

Biodegradation Studies a) Enzyme-catalyzed hydrolysis of polymer from methacryloyloxymethyl benzoate 50 mg samples of the polymer (Example 2r), as finely divided powder, and 20 ml 0.9% aqueous NaCl were added to each of three reaction vials. To one of the vials was 30 also added 0.1 ml esterase from porcine liver in 3.2M $(NH_4)_2SO_4$ (Sigma E-3128, 250U). To another of the vials was added 0.1 ml 3.2M $(NH_4)_2SO_4$. Using a pH-stat (Radiometer), the pH within each of the vials was kept constant at 8.0 by adding 0.1M NaOH. By recording the consumption of NaOH, the rates of hydrolysis were calculated. Over 45 hours at 37° C., the hydrolysis of the polymer with esterase was found to be 11 times faster than the control with $(NH_4)_2SO_4$ without esterase. In the control containing polymer in 0.9% NaCl no hydrolysis was found (see FIG. 10).

TABLE 10

Figure 10:
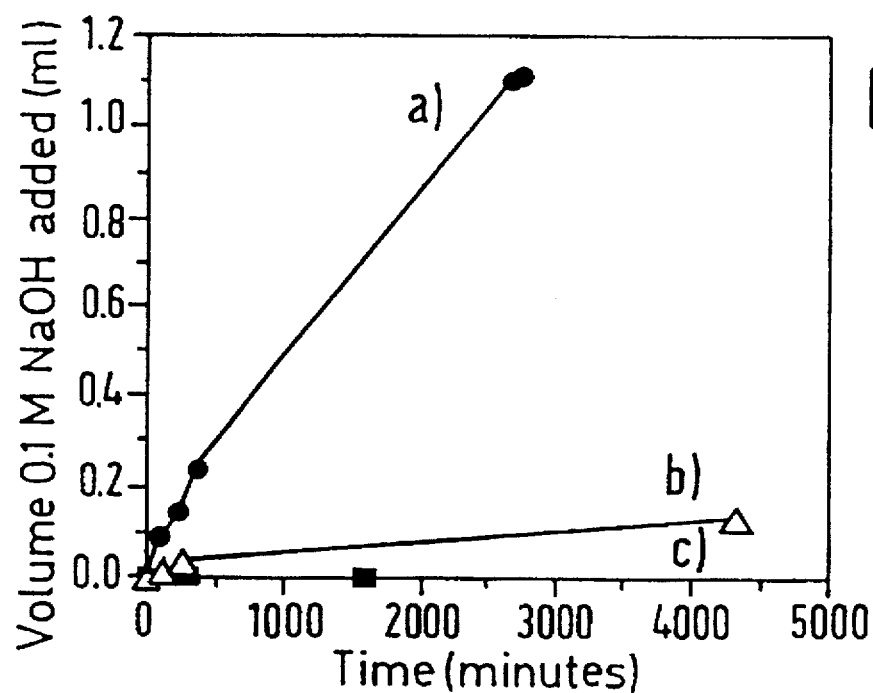
FIG. 10 is a graph showing the rate of hydrolysis of polymers according to Example 2(r) in sulphate containing esterase and ammonium sulphate (line a), saline containing ammonium sulphate (line b), and saline alone (line c)

Consumption of 0.1M NaOH in vial containing polymer and esterase with 0.1 ml 3.2M $(NH_4)_2SO_4$ in 20 ml 0.9% NaCl-solution (see plot (a) of FIG. 10):

| Time (min) | pH | Volume 0.1M NaOH added (ml) |
|---|---|---|
| 0 | 8.00 | 0.000 |
| 100 | 8.00 | 0.080 |
| 220 | 8.00 | 0.142 |
| 355 | 8.00 | 0.239 |
| 2670 | 8.00 | 1.101 |
| 2710 | 8.00 | 1.105 |

TABLE 11

Consumption of 0.1M NaOH in control containing 0.1 ml 3.2M $(NH_4)_2SO_4$ in 20 ml 0.9% NaCl-solution (see plot (b) of FIG. 10):

| Time (min) | pH | Volume 0.1M NaOH added (ml) |
|---|---|---|
| 0 | 8.00 | 0.000 |
| 120 | 8.00 | 0.012 |
| 240 | 8.00 | 0.030 |
| 4316 | 8.00 | 0.130 |

TABLE 12

Consumption of 0.1M NaOH in control containing polymer in 20 ml 0.9% NaCl-solution (see plot (c) of FIG. 10):

| Time (min) | pH | Volume 0.1M NaOH added (ml) |
|---|---|---|
| 0 | 8.4 | 0 |
| 115 | 8.0 | 0.002 |
| 250 | 8.0 | 0.002 |
| 300 | 8.0 | 0.002 |
| 1600 | 8.0 | 0.002 | b) Enzyme-catalyzed hydrolysis of polymer from methylene bis(16-hydroxyhexadecanoate) and adipoyl chloride 50 mg samples of the polymer (Example 2b), as finely divided powder, and 20 ml 0.9% aqueous NaCl were added to each of three reaction vials. To one of the vials was also added 0.1 ml esterase from porcine liver in 3.2M $(NH_4)_2SO_4$ (Sigma E-3128, 250U). To another of the vials was added 0.1 ml 3.2M $(NH_4)_2SO_4$. Using a pH-stat (Radiometer), the pH within each of the vials was kept constant at 8.0 by adding 0.1M NaOH. By recording the consumption of NaOH, the rates of hydrolysis were calculated. Over 44 hours at 37° C., the hydrolysis of the polymer with esterase was found to be 10 times faster than the control with $(NH_4)_2SO_4$ without esterase. In the control containing polymer in 0.9% NaCl no hydrolysis was found (see FIG. 11).

TABLE 13

Figure 11:
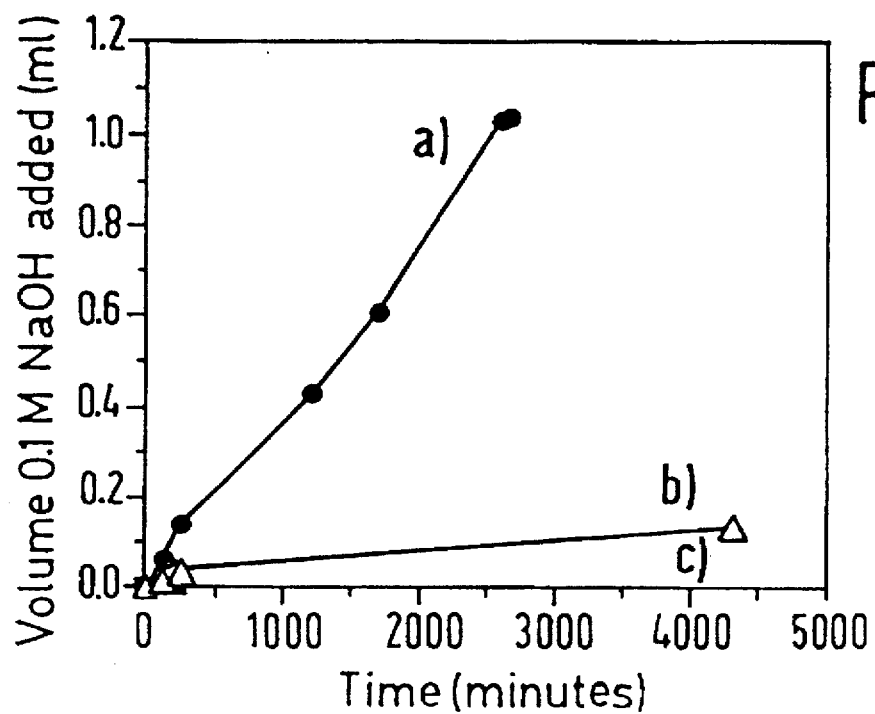
FIG. 11 is a graph showing the rate of hydrolysis of polymers according to Example 2(b) in saline containing esterase and ammonium sulphate (line a), saline containing ammonium sulphate (line b), and saline alone (line c).

Consumption of 0.1M NaOH in vial containing polymer and esterase with 0.1 ml 3.2M $(NH_4)_2SO_4$ in 20 ml 0.9% NaCl-solution (see plot (a) of FIG. 11):

| Time (min) | pH | Volume 0.1M NaOH added (ml) |
|---|---|---|
| 0 | 8.00 | 0.000 |
| 135 | 8.00 | 0.058 |
| 255 | 8.00 | 0.134 |
| 1240 | 8.00 | 0.431 |

TABLE 13-continued

Consumption of 0.1M NaOH in vial containing polymer and esterase with 0.1 ml 3.2M $(NH_4)_2SO_4$ in 20 ml 0.9% NaCl-solution (see plot (a) of FIG. 11):

| Time (min) | pH | Volume 0.1M NaOH added (ml) |
|---|---|---|
| 1705 | 8.00 | 0.602 |
| 2635 | 8.00 | 1.026 |
| 2665 | 8.00 | 1.034 |

TABLE 14

Consumption of 0.1M NaOH in control containing 0.1 ml 3.2M $(NH_4)_2SO_4$ in 20 ml 0.9% NaCl-solution (see plot (b) of FIG. 11):

| Time (min) | pH | Volume 0.1M NaOH added (ml) |
|---|---|---|
| 0 | 8.00 | 0.000 |
| 120 | 8.00 | 0.012 |
| 240 | 8.00 | 0.030 |
| 4316 | 8.00 | 0.130 |

TABLE 15

Consumption of 0.1M NaOH in control containing polymer in 20 ml 0.9% NaCl-solution (see plot (c) of FIG. 11):

| Time (min) | pH | Volume 0.1M NaOH added (ml) |
|---|---|---|
| 0 | 8.4 | 0.002 |
| 50 | 7.9 | 0.002 |
| 145 | 7.9 | 0.002 |
| 235 | 7.9 | 0.002 |

REFERENCES:
1. Folkmann M., Lund F. J., *Synthesis* 1990, 1159
2. Benneche T., Strande P., Wiggen U., *Acta Chem. Scand.* 43, 1988, 74
3. Stroholm J., Kopecek J., *Angew. Macromol. Chemie* 70, 1978, 109

We claim:

1. A method of generating enhanced images of a human or non-human animal body which comprises:
   (1) administering to said body a contrast agent comprising gas-containing or gas-generating polymer microparticles and/or microballoons, characterized in that the polymer is a biodegradable polymer containing units of formula (II)

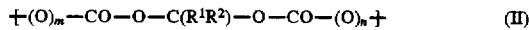

wherein $R^1$ and $R^2$ each represent a hydrogen atom or a carbon-attached monovalent organic group or $R^1$ and $R^2$ together form a carbon-attached divalent organic group, and m and n, which may be the same or different, are each zero or 1; and
   (2) generating an ultrasound or MR image of at least a part of said body.

2. A method as claimed in claim 1 wherein the polymer contains units of formula (III):

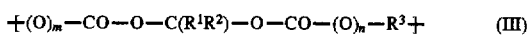

wherein m, n, $R^1$ and $R^2$ are as defined in claim 1 and $R^3$ is a divalent organic group.

3. A method as claimed in claim 2 wherein $R^3$ is a polymeric group.

4. A method as claimed in claim 2 wherein the polymer is a block or graft copolymer.

5. A method as claimed in claim 2 in which $R^3$ is selected from the group consisting of an alkylene or alkenylene group having up to 20 carbon atoms; a cycloalkylene group having up to 10 carbon atoms; an aralkylene group having up to 20 carbon atoms; an arylene group having up to 20 carbon atoms; a heterocyclic group having up to 20 carbon atoms and one or more heteroatoms selected from the group consisting of O, N and S; and any of the preceding groups carrying one or more functional substituents and/or interrupted in the carbon chain and/or terminated by one or more heteroatoms.

6. A method as claimed in claim 5 wherein $R^3$ is a carbon-attached divalent organic group.

7. A method as claimed in claim 6 wherein m and n are zero and $R^3$ represents a group of formula

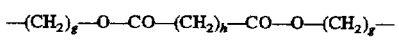

where g represents an integer in the range 8–20 and h represents an integer in the range 1–8.

8. A method as claimed in claim 7 wherein $R^3$ represents the group

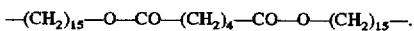

9. A method as claimed in claim 8 wherein $R^1$ represents a methyl group and $R^2$ represents a hydrogen atom.

10. A method as claimed in claim 9 wherein the contrast agent further comprises human serum albumin.

11. A method as claimed in claim 1 wherein units of formula (11) crosslink polymer chains.

12. A method as claimed in claim 1 wherein the polymer is water-insoluble and contains units of formula (VI)

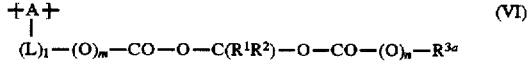

wherein m, n, $R^1$, and $R^2$ are as defined in claim 1; A represents a repeating unit of a non-polypeptide polymer backbone chain; L represents a linking group; I is zero or 1; and $R^{3a}$ represents a lipophilic organic group; whereby the said lipophilic group is biodegradatively clearable to yield a water-soluble polymer.

13. A method as claimed in claim 12 wherein $R^{3a}$ is selected from the group consisting of aliphatic groups having up to 10 carbon atoms, cycloalkyl groups having up to 10 carbon atoms, araliphatic groups having up to 20 carbon atoms, aryl groups having up to 20 carbon atoms, heterocyclic groups having up to 20 carbon atoms and one or more heteroatoms selected from the group consisting of O, N and S, and any of the preceding groups carrying one or more functional substituents.

14. A method as claimed in claim 12 wherein L is a $C_{1-3}$ alkylene group optionally linked to A by and/or interrupted by one or more oxy, carbonyl, oxycarbonyl, imino or iminocarbonyl groups.

15. A method as claimed in claim 12 wherein the polymer is a polysaccharide.

16. A method as claimed in claim 12 wherein the repeating units A and any comonomer units contain 1–6 carbon atoms optionally interrupted by one or more heteroatoms selected from the group consisting of O, N and S and/or substituted by one or more substituents comprising such heteroatoms.

17. A method as claimed in claim 16 wherein A represents ethylene or propylene.

18. A method as claimed in claim 1 wherein $R^1$ and $R^2$, when other than hydrogen, are selected from the group consisting of aliphatic groups having up to 10 carbon atoms, cycloalkyl groups having up to 10 carbon atoms, araliphatic groups having up to 20 carbon atoms, aryl groups having up to 20 carbon atoms, heterocyclic groups having up to 20 carbon atoms and one or more heteroatoms selected from the group consisting of O, N and S, and any of the preceding groups carrying one or more functional substituents.

19. A method as claimed in claim 1 wherein $R^1$ represents a methyl group and $R^3$ represents a hydrogen atom.

20. A method as claimed in claim 1 wherein the contrast agent further comprises one or more compounds selected from the group consisting of gelatin, polyvinyl alcohol, lipophilised starch, gum arabic, poly(oxyethylene)-poly (oxypropylene)-poly(oxyethylene) block copolymers, and human serum albumin.

21. A method as claimed in claim 1 wherein the contrast agent further comprises a block copolymer surfactant containing biodegradable linkages of formula (II) as defined in claim 1.

22. A method as claimed in claim 21 wherein the block copolymer surfactant contains biodegradable linkages of formula (II) wherein m and n are zero and $R^1$ and $R^2$ are selected from the group consisting of hydrogen atoms and methyl groups.

23. A method as claimed in claim 22 wherein the block copolymer surfactant comprises at least one hydrophilic block comprising polyethylene glycol units and at least one hydrophobic part comprising units of formula

where g is an integer in the range 9–19 and $R^a$ and $R^b$ each represent a valence bond or a linking group.

24. A process for the preparation of a contrast agent, which contrast agent comprises gas-containing or gas-generating polymer microparticles and/or microballoons, characterized in that the polymer is a biodegradable polymer containing units of formula (II)

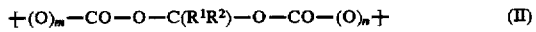

wherein $R^1$ and $R^2$ each represent a hydrogen atom or a carbon-attached monovalent organic group or $R^1$ and $R^2$ together form a carbon-attached divalent organic group, and m and n, which may be the same or different, are each zero or 1;

wherein the process comprises incorporating a gas or gas-generating agent into a biodegradable polymer containing units of formula (II) so as to form polymer microparticles and/or microballoons.

25. The process of claim 24 which comprises dissolving the polymer in a water-immiscible solvent, emulsifying the said solution in an aqueous phase and lyophilizing said emulsion.

26. The process of claim 25 wherein the solvent is selected from the group consisting of heptane, toluene, xylene, camphene, limonene and naphthalene.

27. The process of claim 25 wherein the solution is emulsified in the presence of a compound selected from the group consisting of gelatin, polyvinyl alcohol, lipophilised starch, gum arabic, poly(oxyethylene)-poly(oxypropylene)-poly(oxyethylene) block copolymers, human serum albumin and block copolymer surfactants containing biodegradable linkages of formula (II).

28. The process of claim 25 wherein the solvent is (−)-camphene and the solution is emulsified in aqueous human serum albumin.

29. A process as claimed in claim 24 wherein the polymer contains units of formula (III):

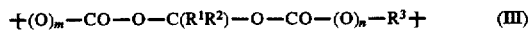

wherein m, n, $R^1$ and $R^2$ are as defined in claim 29 and $R^3$ is a divalent organic group.

30. A process as claimed in claim 29 in which $R^3$ is selected from the group consisting of an alkylene or alkenylene group having up to 20 carbon atoms; a cycloalkylene group having up to 10 carbon atoms; an aralkylene group having up to 20 carbon atoms; an arylene group having up to 20 carbon atoms; a heterocyclic group having up to 20 carbon atoms and one or more heteroatoms selected from the group consisting of O, N and S; and any of the preceding groups carrying one or more functional substituents and/or interrupted in the carbon chain and/or terminated by one or more heteroatoms.

31. A process as claimed in claim 30 wherein $R^3$ is a carbon-attached divalent organic group.

32. A process as claimed in claim 31 wherein m and n are zero and $R^3$ represents a group of formula

where g represents an integer in the range 8–20 and h represents an integer in the range 1–8.

33. A process as claimed in claim 32 wherein $R^3$ represents the group

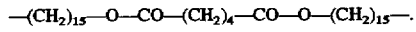

34. A process as claimed in claim 33 wherein $R^1$ represents a methyl group and $R^2$ represents a hydrogen atom.

35. A process as claimed in claim 34 wherein the contrast agent further comprises human serum albumin.

36. A process as claimed in claim 29 wherein $R^3$ is a polymeric group.

37. A process as claimed in claim 29 wherein the polymer is a block or graft copolymer.

38. A process as claimed in claim 24 wherein units of formula (II) crosslink polymer chains.

39. A process as claimed in claim 24 wherein the polymer is water-insoluble and contains units of formula (VI)

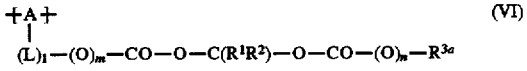

wherein m, n, $R^1$, and $R^2$ are as defined in claim 24, A represents a repeating unit of a non-polypeptide polymer backbone chain; L represents a linking group; I is zero or 1; and $R^{3a}$ represents a lipophilic organic group; whereby the said lipophilic group is biodegradatively cleavable to yield a water-soluble polymer.

40. A process as claimed in claim 39 wherein the repeating units A and any comonomer units contain 1–6 carbon atoms optionally interrupted by one or more heteroatoms selected from the group consisting of O, N and S and/or substituted by one or more substituents comprising such heteroatoms.

41. A process as claimed in claim 40 wherein A represents ethylene or propylene.

42. A process as claimed in claim 39 wherein L is a $C_{1-3}$ alkylene group optionally linked to A by and/or interrupted by one or more oxy, carbonyl, oxycarbonyl, imino or iminocarbonyl groups.

43. A process as claimed in claim 39 wherein the polymer is a polysaccharide.

44. A process as claimed in claim 39 wherein $R^{3a}$ is selected from the group consisting of aliphatic groups having up to 10 carbon atoms, cycloalkyl groups having up to 10 carbon atoms, araliphatic groups having up to 20 carbon atoms, aryl groups having up to 20 carbon atoms, heterocyclic groups having up to 20 carbon atoms and one or more heteroatoms selected from the group consisting of O, N and S, and any of the preceding groups carrying one or more functional substituents.

45. A process as claimed in claim 24 wherein $R^1$ and $R^2$, when other than hydrogen, are selected from the group consisting of aliphatic groups having up to 10 carbon atoms, cycloalkyl groups having up to 10 carbon atoms, araliphatic groups having up to 20 carbon atoms, aryl groups having up to 20 carbon atoms, heterocyclic groups having up to 20 carbon atoms and one or more heteroatoms selected from the group consisting of O, N and S, and any of the preceding groups carrying one or more functional substituents.

46. A process as claimed in claim 24 wherein $R^1$ represents a methyl group and $R^3$ represents a hydrogen atom.

47. A process as claimed in claim 24 wherein the contrast agent further comprises one or more compounds selected from the group consisting of gelatin, polyvinyl alcohol, lipophilised starch, gum arabic, poly(oxyethylene)-poly(oxpropylene)-poly(oxyethylene) block copolymers, and human serum albumin.

48. A process as claimed in claim 24 wherein the contrast agent further comprises a block copolymer surfactant containing biodegradable linkages of formula (II) as defined in claim 24.

49. A process as claimed in claim 48 wherein the block copolymer surfactant contains biodegradable linkages of formula (II) wherein m and n are zero and $R^1$ and $R^2$ are selected from the group consisting of hydrogen atoms and methyl groups.

50. A process as claimed in claim 49 wherein the block copolymer surfactant comprises at least one hydrophilic block comprising polyethylene glycol units and at least one hydrophobic part comprising units of formula

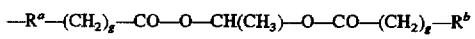

where g is an integer in the range 9–19 and $R^a$ and $R^b$ each represent a valence bond or a linking group.

* * * * *